(12) United States Patent
Henschke et al.

(10) Patent No.: US 8,735,611 B2
(45) Date of Patent: May 27, 2014

(54) CRYSTALLINE FORMS OF CABAZITAXEL

(71) Applicant: ScinoPharm Taiwan, Ltd., Tainan (TW)

(72) Inventors: Julian Paul Henschke, Summertown (AU); TsungYu Hsiao, Kaohsiung (TW); MengFen Ho, Tainan (TW); YuanChang Huang, Kaohsiung (TW)

(73) Assignee: ScinoPharm Taiwan, Ltd., Tainan (TW)

( * ) Notice: Subject to any disclaimer, the term of this patent is extended or adjusted under 35 U.S.C. 154(b) by 0 days.

(21) Appl. No.: 13/965,015

(22) Filed: Aug. 12, 2013

(65) Prior Publication Data

US 2014/0045926 A1 Feb. 13, 2014

Related U.S. Application Data

(62) Division of application No. 13/605,908, filed on Sep. 6, 2012, now Pat. No. 8,575,373.

(60) Provisional application No. 61/606,288, filed on Mar. 2, 2012, provisional application No. 61/533,111, filed on Sep. 9, 2011.

(51) Int. Cl.
*C07D 305/00* (2006.01)

(52) U.S. Cl.
USPC .......................................................... 549/510

(58) Field of Classification Search
None
See application file for complete search history.

(56) References Cited

U.S. PATENT DOCUMENTS

| 5,847,170 A | 12/1998 | Bouchard et al. |
| 5,962,705 A | 10/1999 | Didier et al. |
| 7,241,907 B2 * | 7/2007 | Didier et al. ................... 549/510 |
| 2005/0065138 A1 | 3/2005 | Didier et al. |
| 2011/0144362 A1 * | 6/2011 | Billot et al. ................... 549/541 |
| 2014/0011865 A1 * | 1/2014 | Simo et al. .................... 514/449 |

FOREIGN PATENT DOCUMENTS

| WO | 96/30355 A1 | 10/1996 |
| WO | 2009/115655 A2 | 9/2009 |
| WO | 2012/142117 A1 | 10/2012 |

OTHER PUBLICATIONS

Morissette et al. in Drug Delivery Reviews, 56 (2004) 275-300.*
International Search Report and Written Opinion, Mail Date Mar. 28, 2013, PCT Application No. PCT/IB2012/002134, 11 pages.
Morisette et al. "High-throughput crystallization: polymorphs, salts, co-crystals and solvates of pharmaceutical solids", *Advanced Drug Delivery*, vol. 56, pp. 275-300.

* cited by examiner

*Primary Examiner* — Dennis Heyer
*Assistant Examiner* — Daniel M Podgorski
(74) *Attorney, Agent, or Firm* — Kilpatrick Townsend & Stockton LLP

(57) ABSTRACT

The present invention provides crystalline forms, including an anhydrate form, of cabazitaxel and processes for the preparation of these forms, designated as Forms C1, C2, C3, C4, C5, C6, C7, C8, C8b, C9 and C9p.

8 Claims, 49 Drawing Sheets

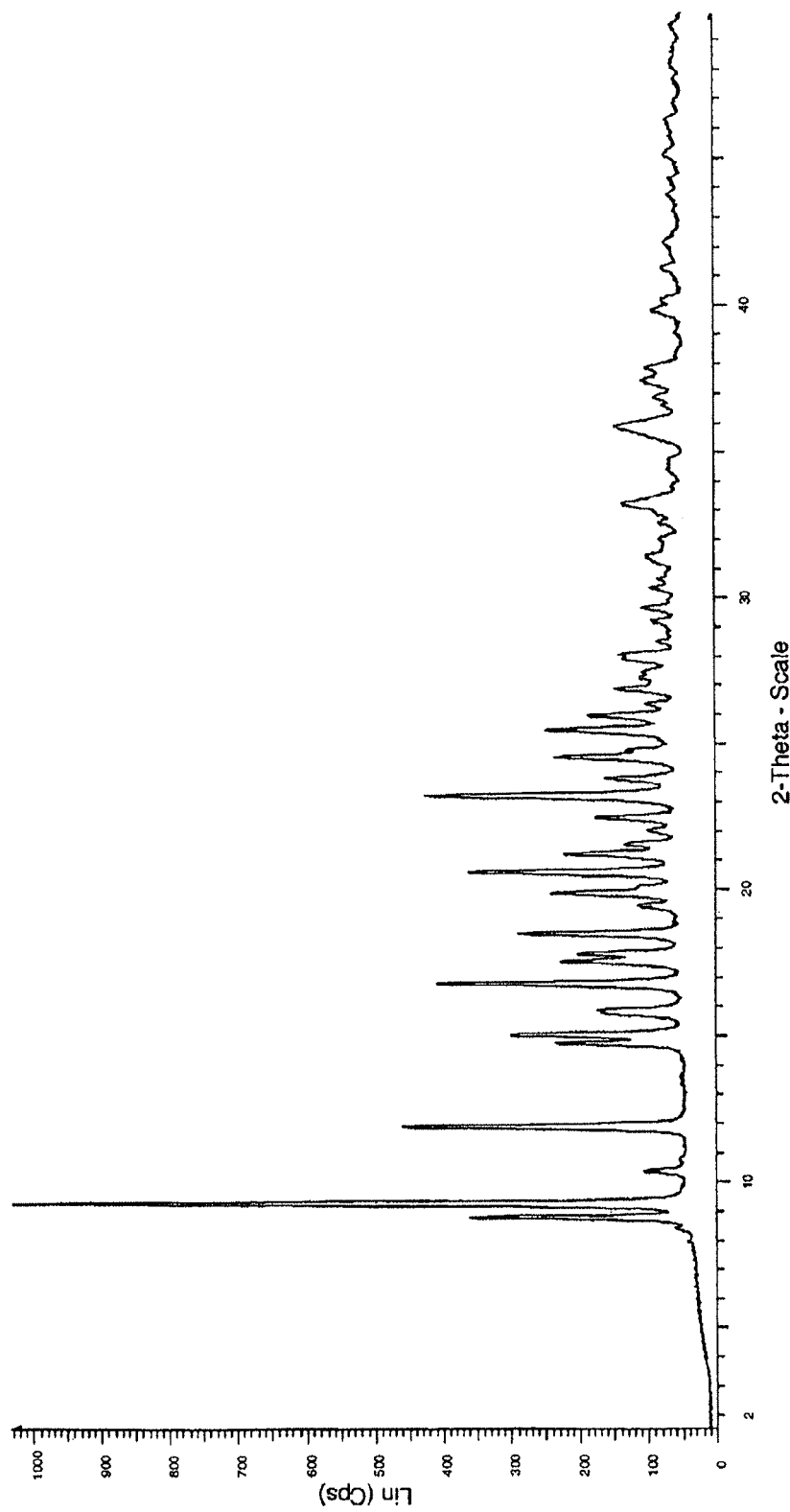
Figure 1. XRPD pattern of an acetone solvate of cabazitaxel

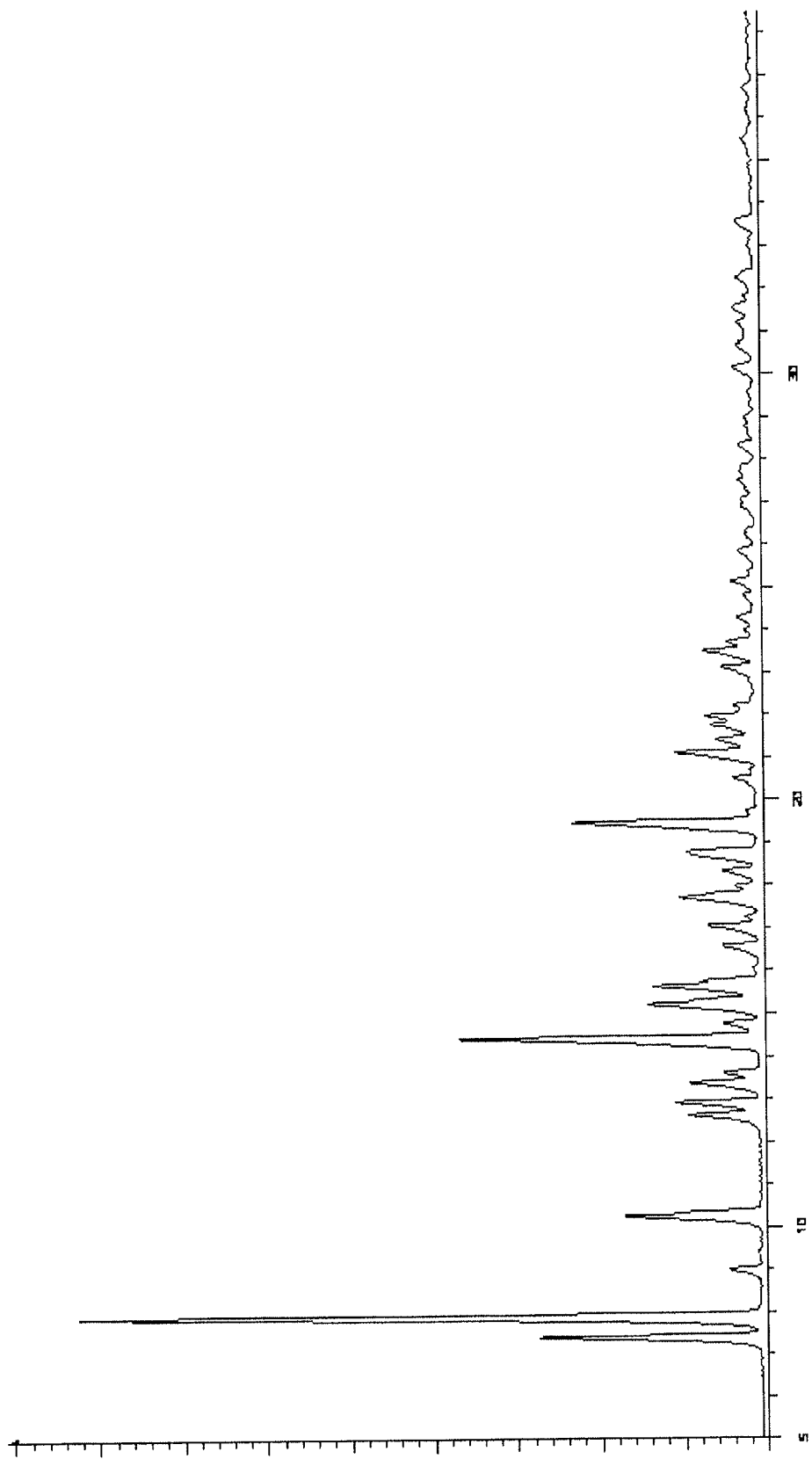
Figure 2a. XRPD pattern of cabazitaxel Form C1.

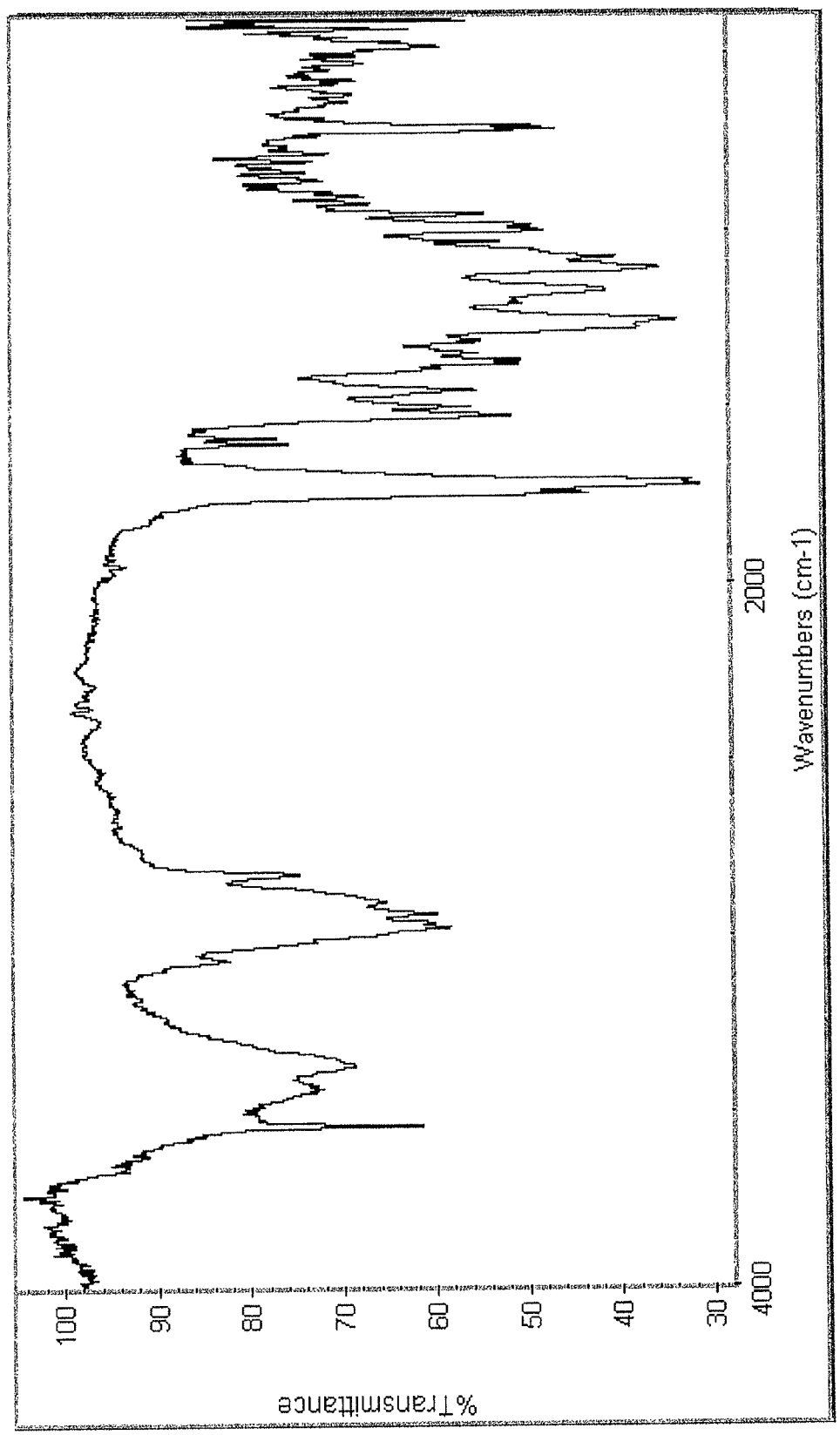
Figure 2b. IR spectrum of cabazitaxel Form C1.

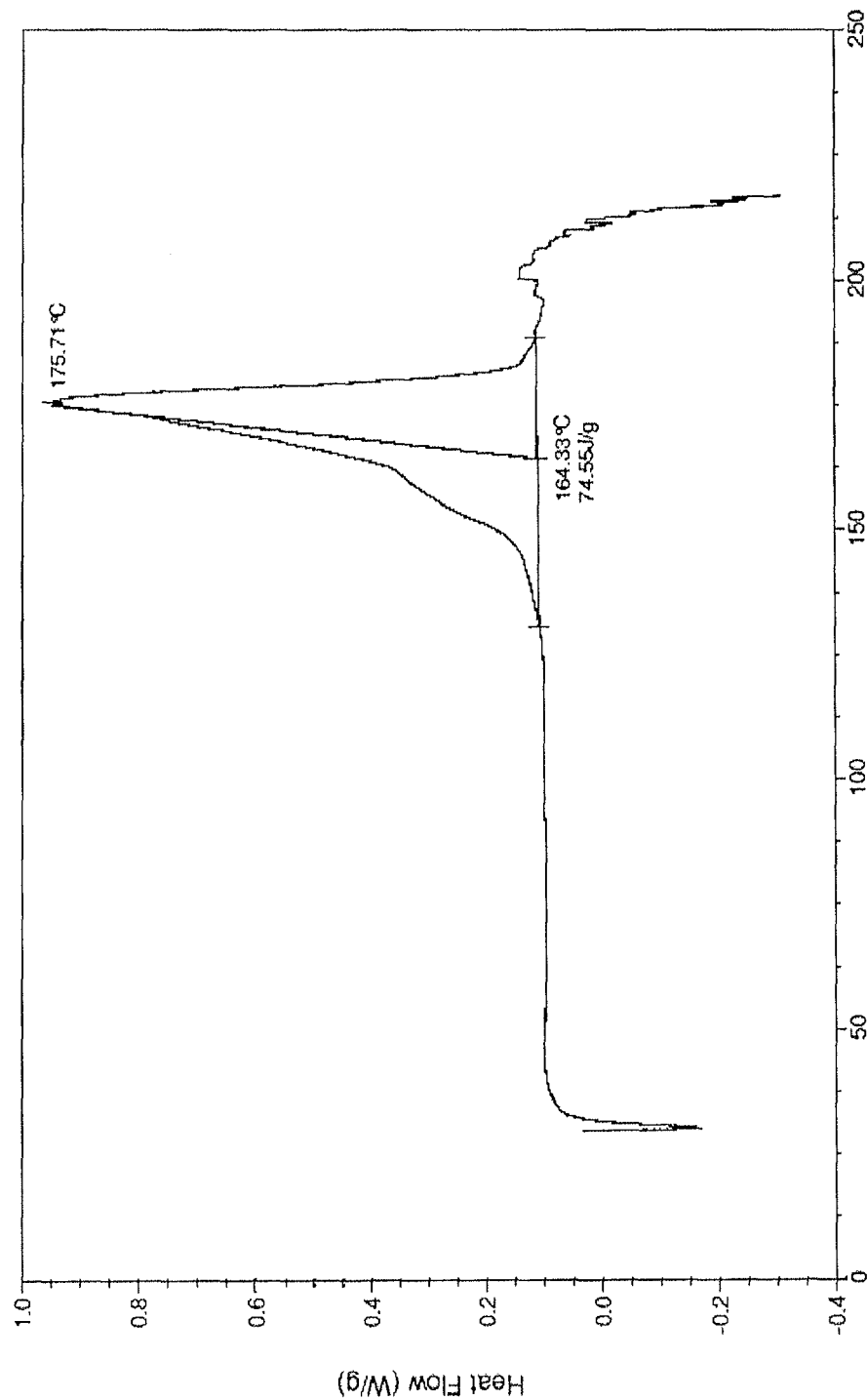
Figure 2c. DSC trace of cabazitaxel Form C1.

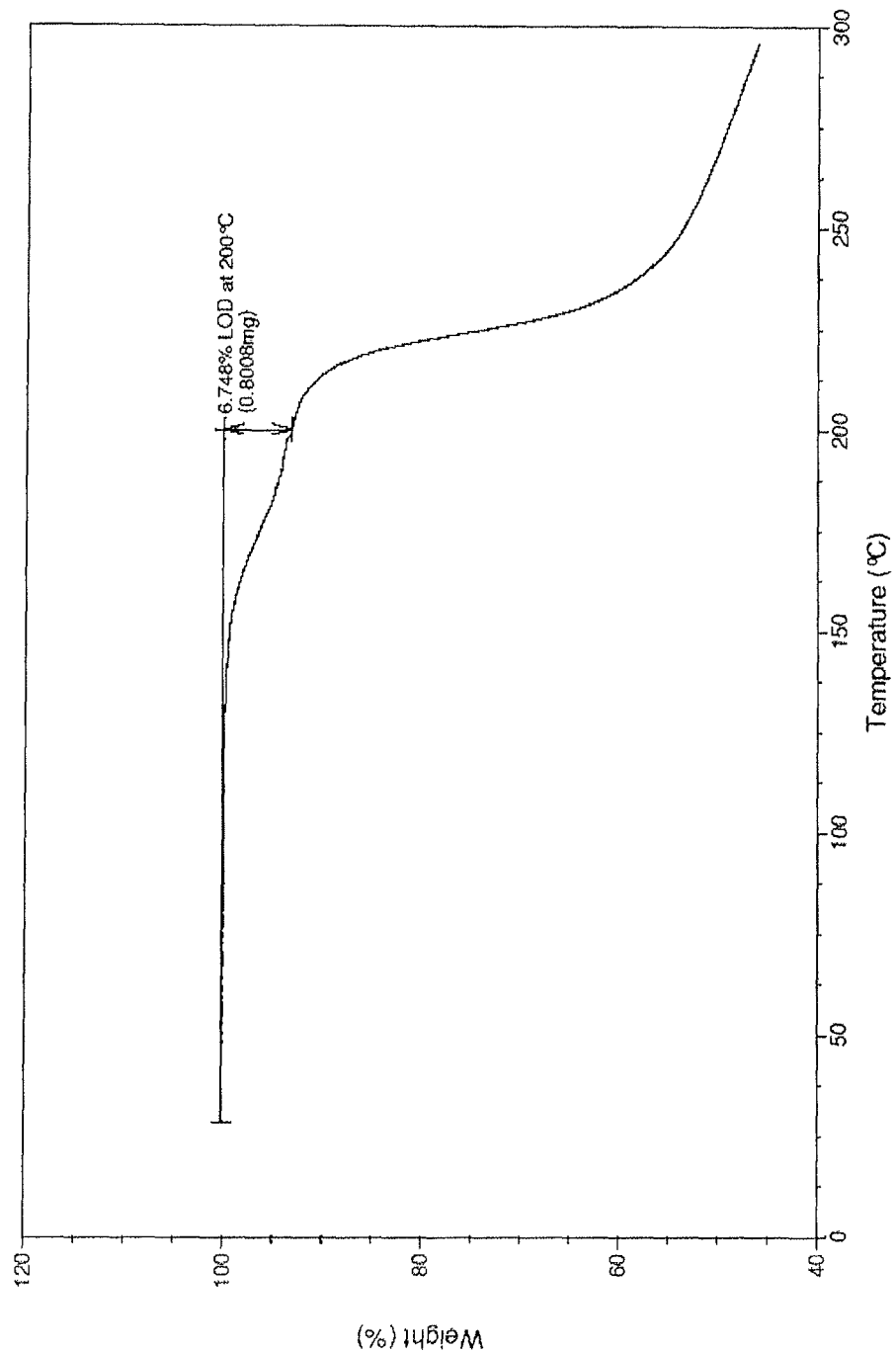
Figure 2d. TGA trace of cabazitaxel Form C1.

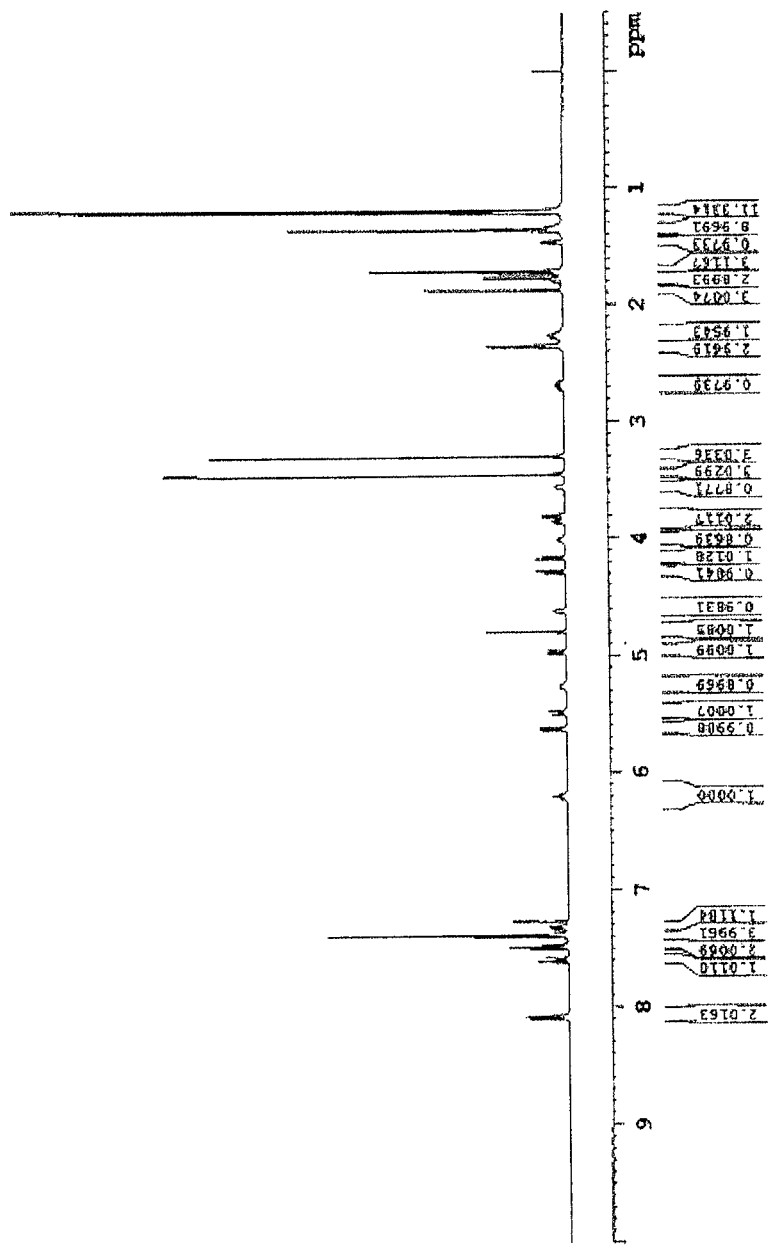
Figure 2e. ¹H NMR spectrum of cabazitaxel Form C1.

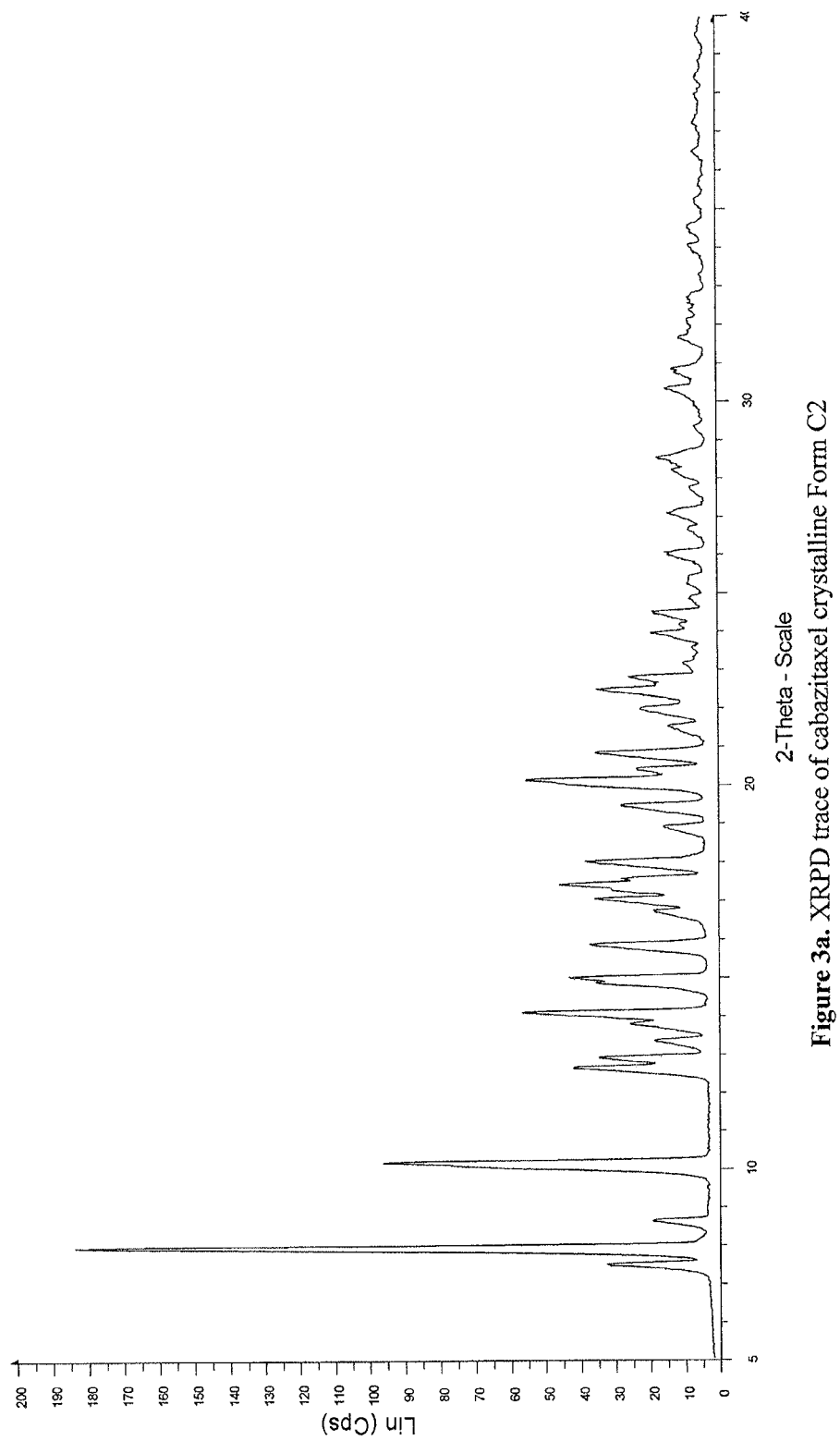
Figure 3a. XRPD trace of cabazitaxel crystalline Form C2

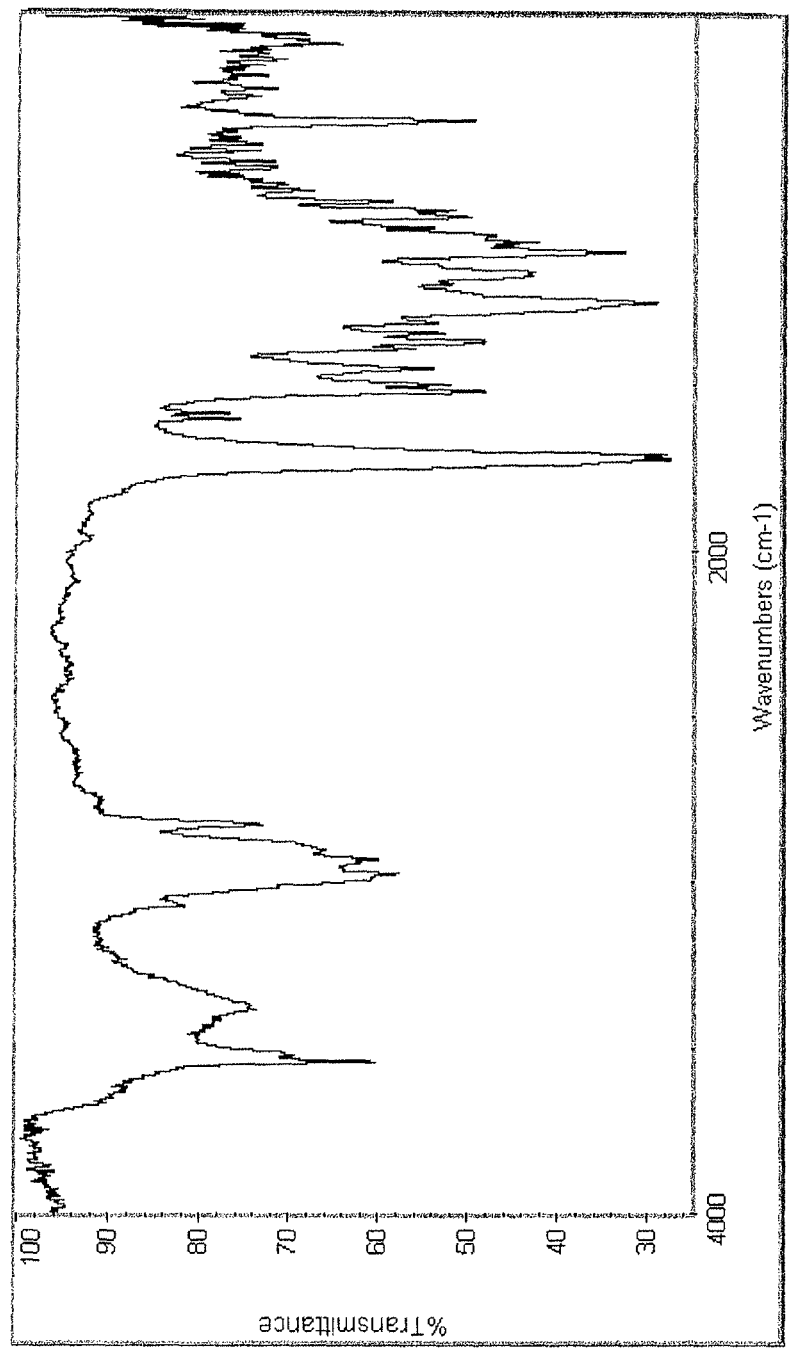
Figure 3b. IR a spectrum of cabazitaxel crystalline Form C2

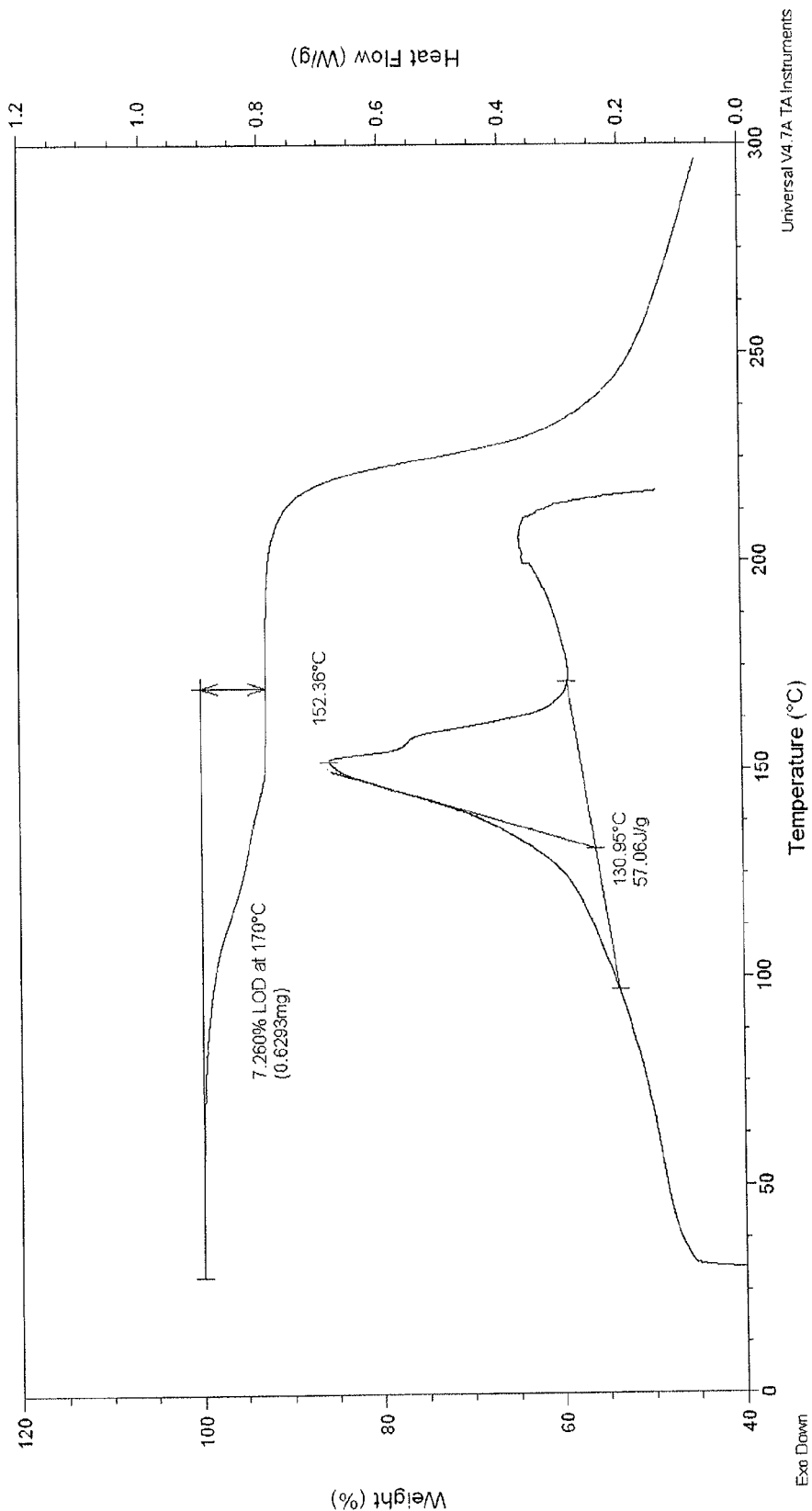
Figure 3c. DSC/TGA traces of cabazitaxel crystalline Form C2

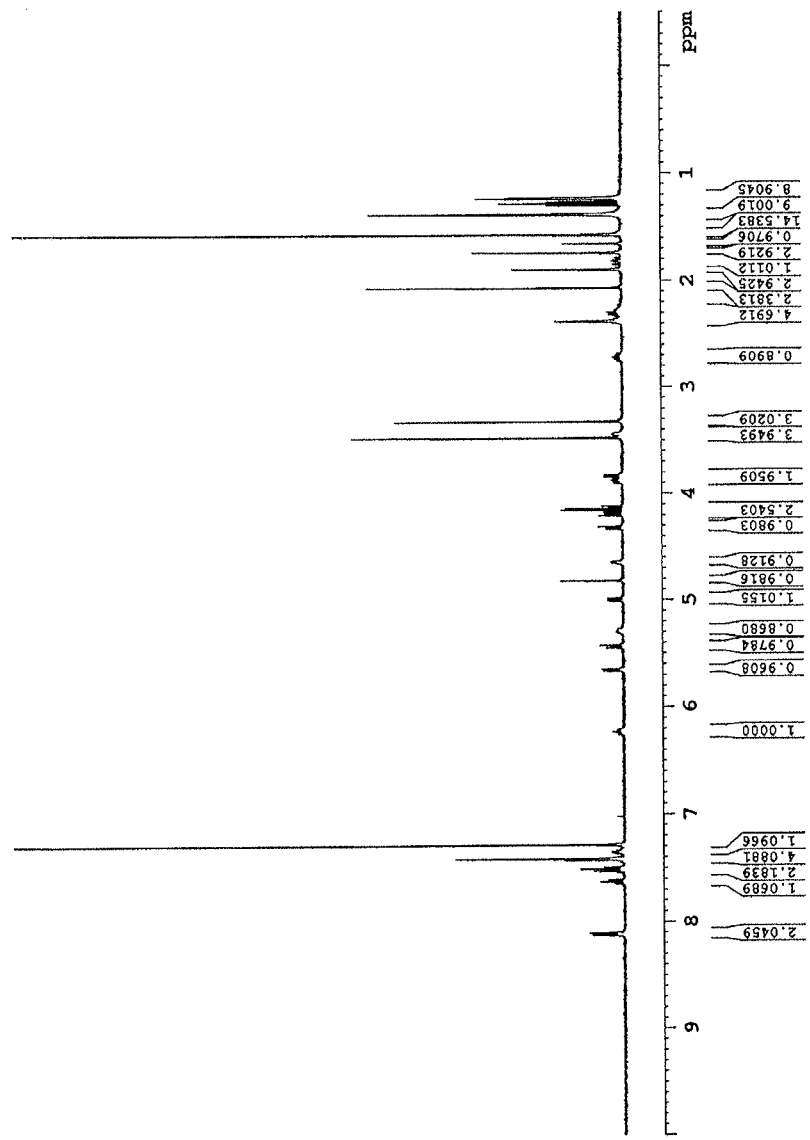
Figure 3d. ¹H NMR spectrum of cabazitaxel crystalline Form C2

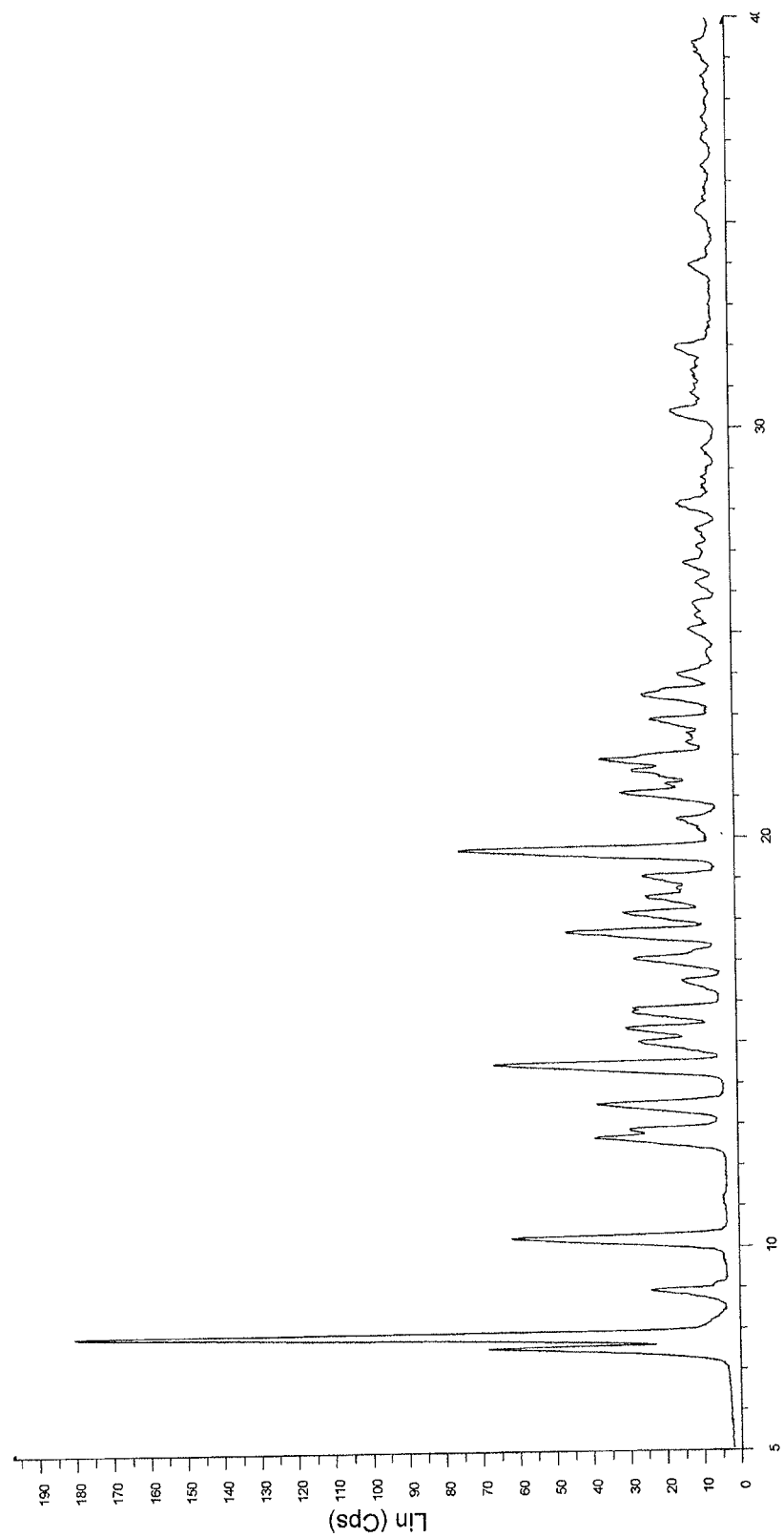
Figure 4a. XRPD pattern of cabazitaxel crystalline Form C3

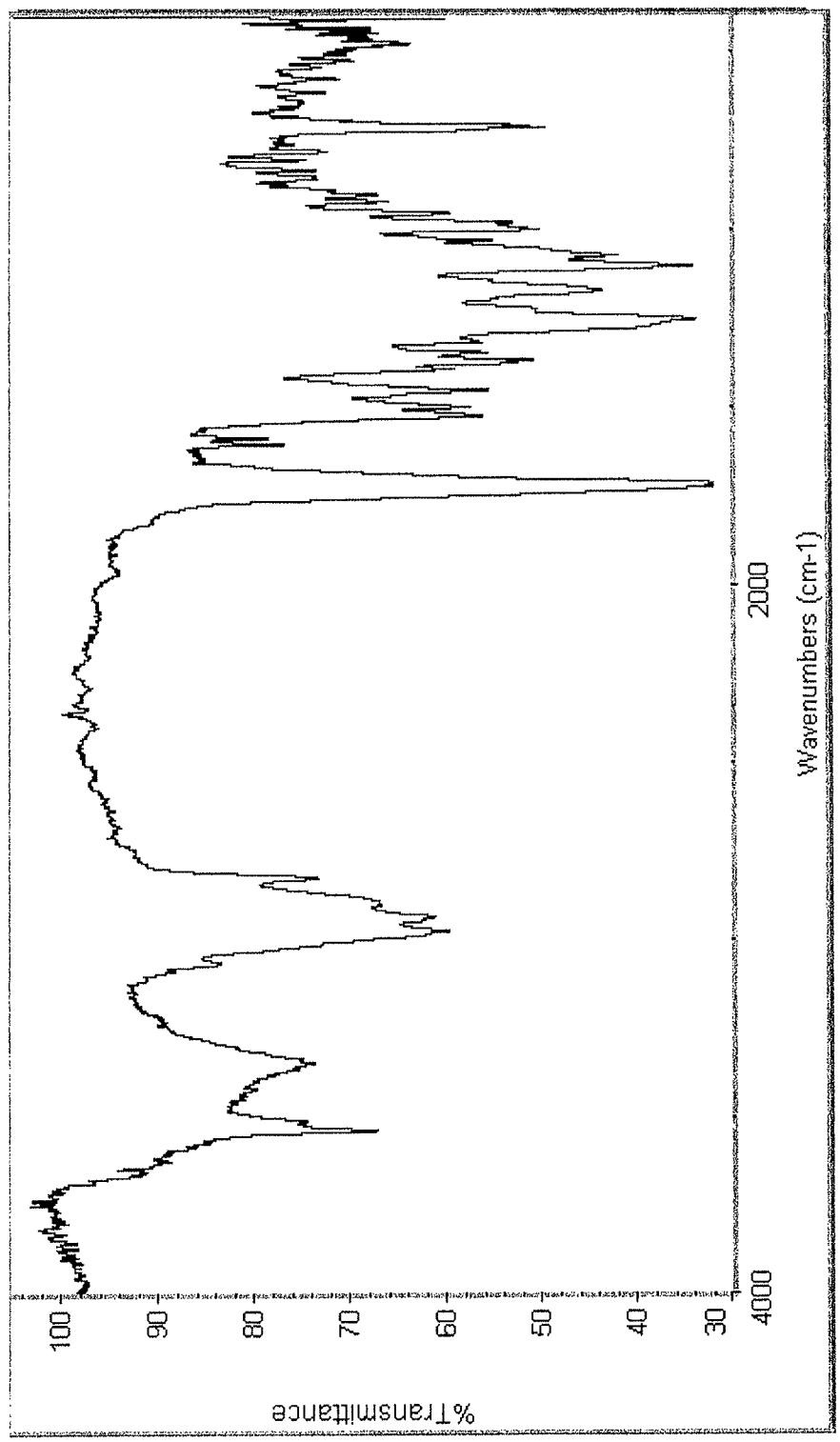
Figure 4b. IR spectrum of cabazitaxel crystalline Form C3

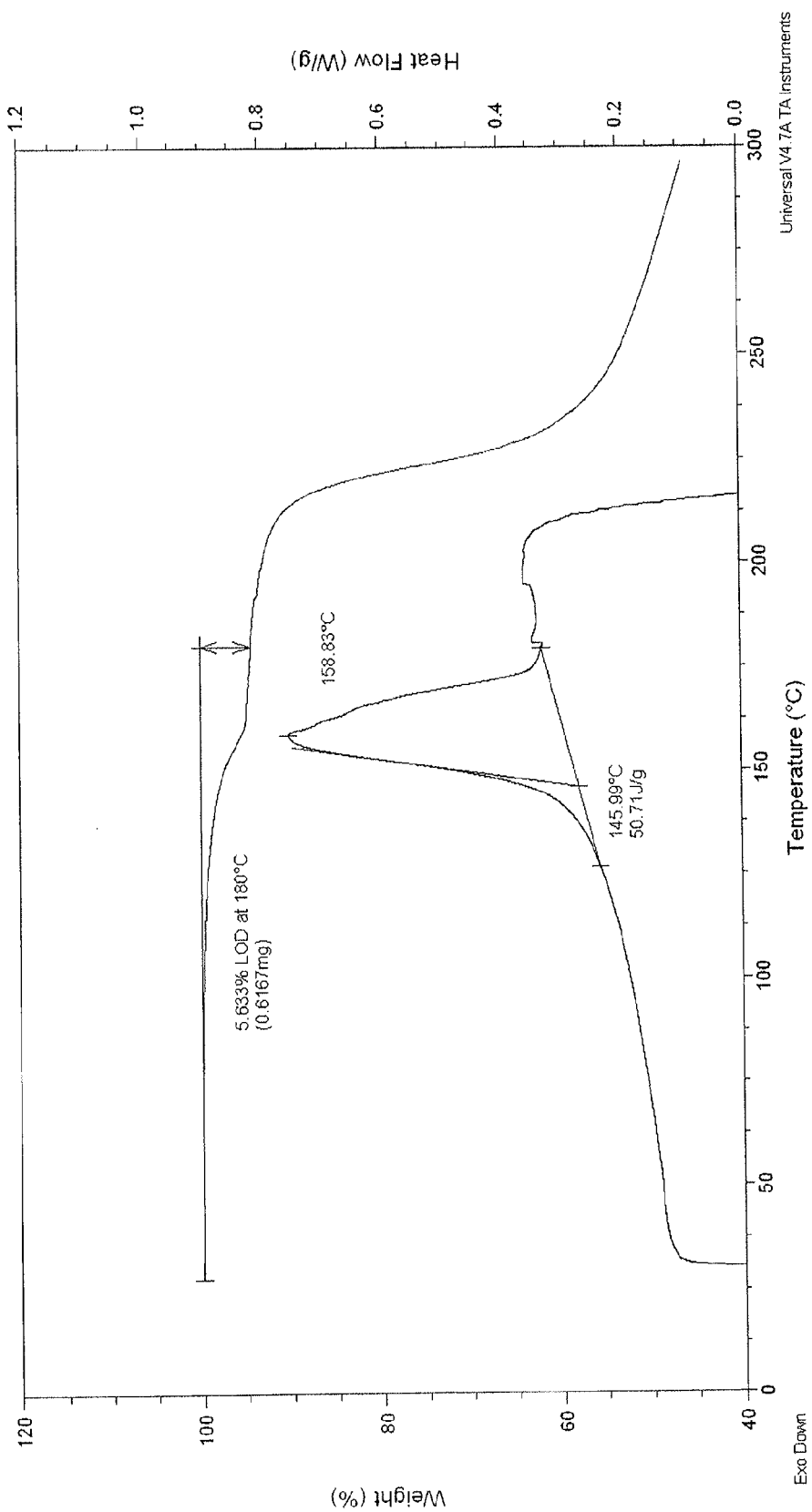
Figure 4c. DSC/TGA trace of cabazitaxel crystalline Form C3

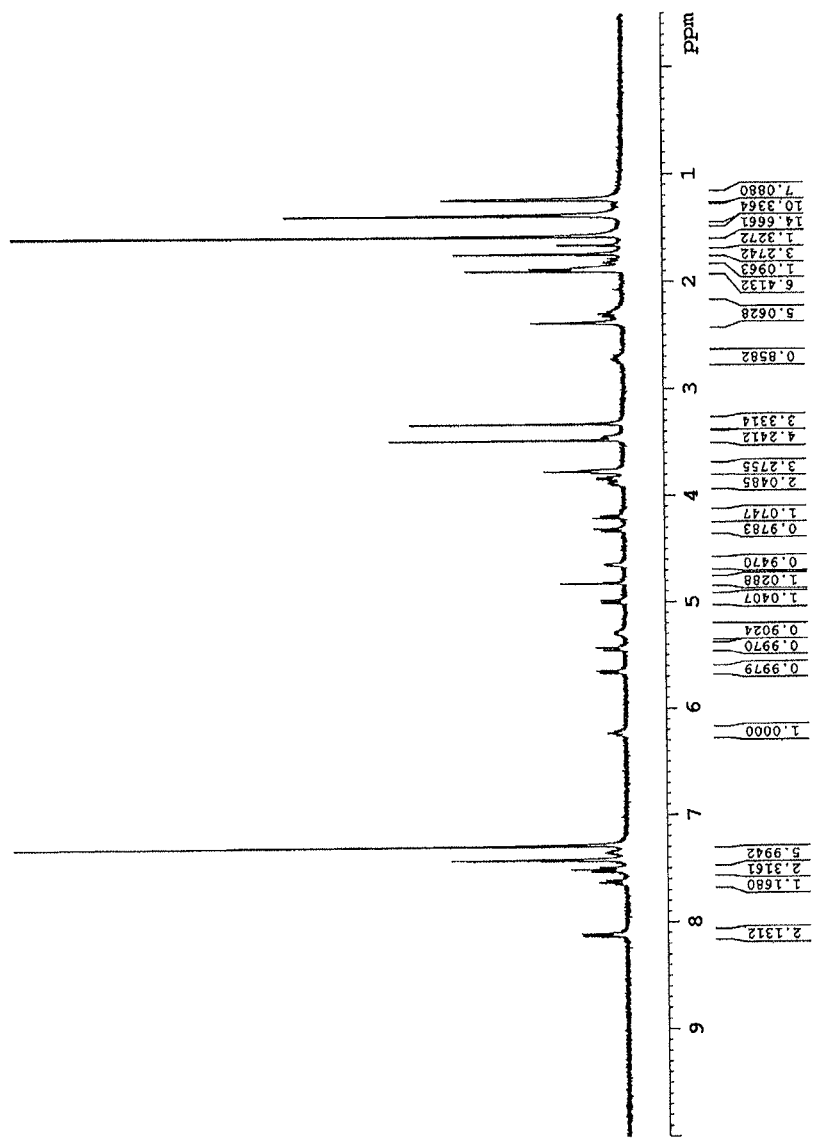
Figure 4d. ¹H NMR spectrum of cabazitaxel crystalline Form C3

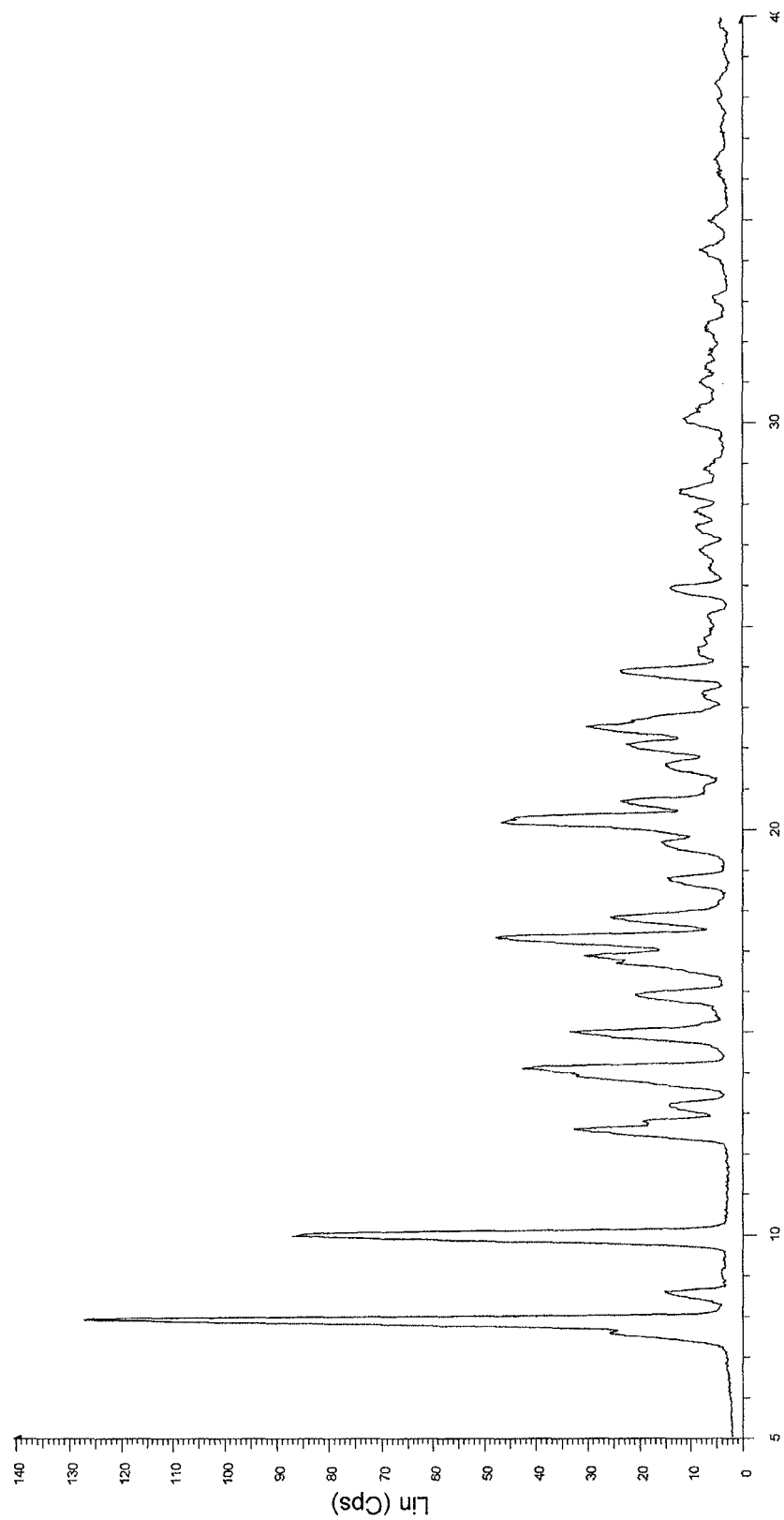
Figure 5a. XRPD pattern of cabazitaxel crystalline Form C4

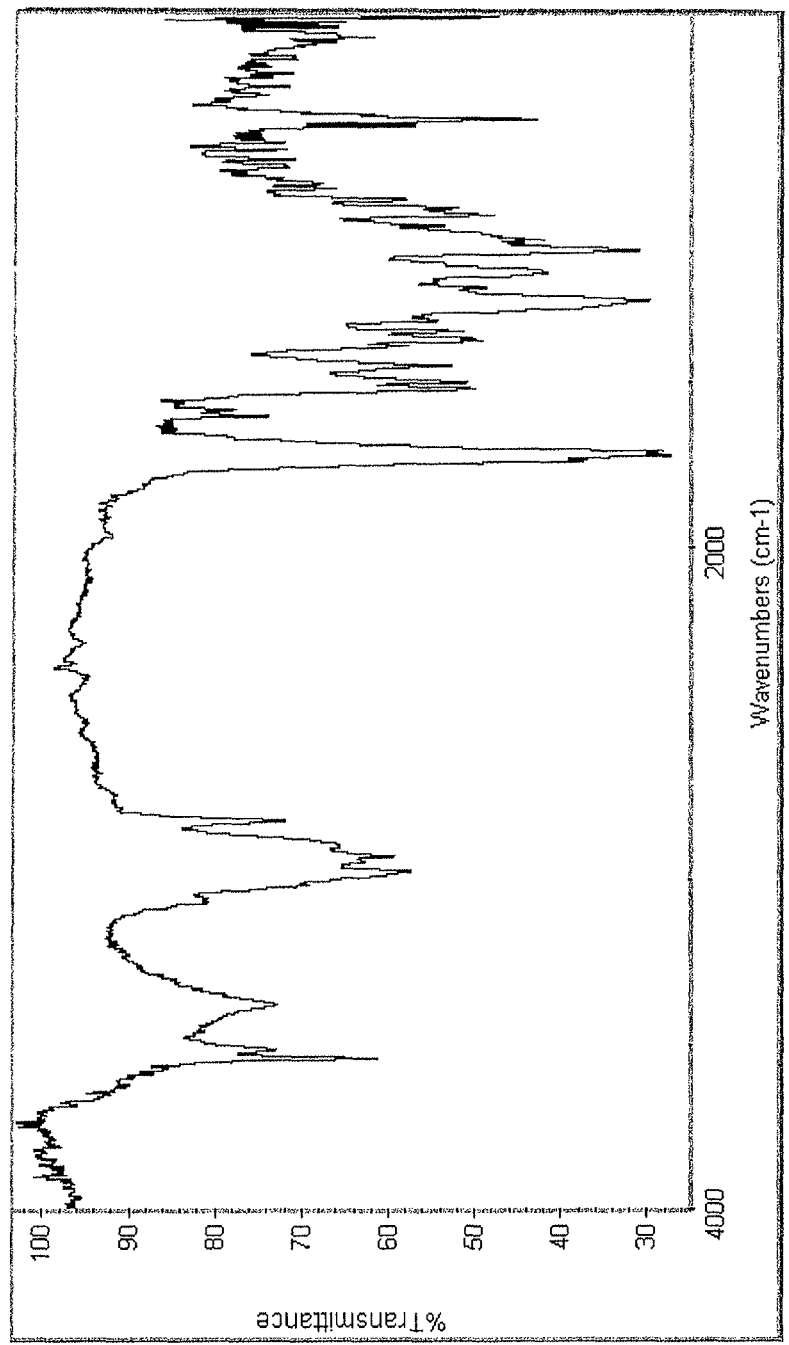
Figure 5b. IR spectrum of cabazitaxel crystalline Form C4

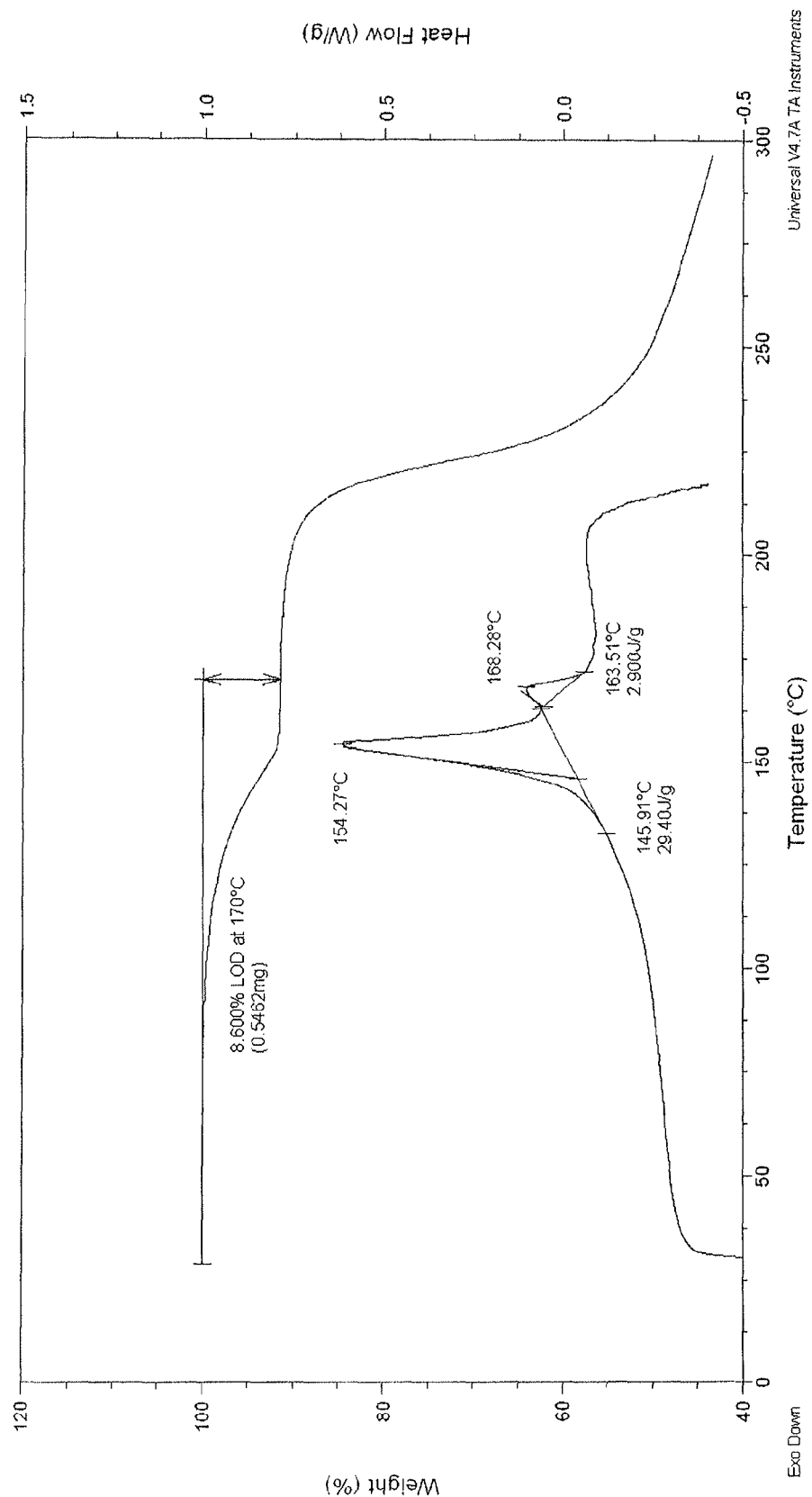
Figure 5c. DSC/TGA trace of cabazitaxel crystalline Form C4

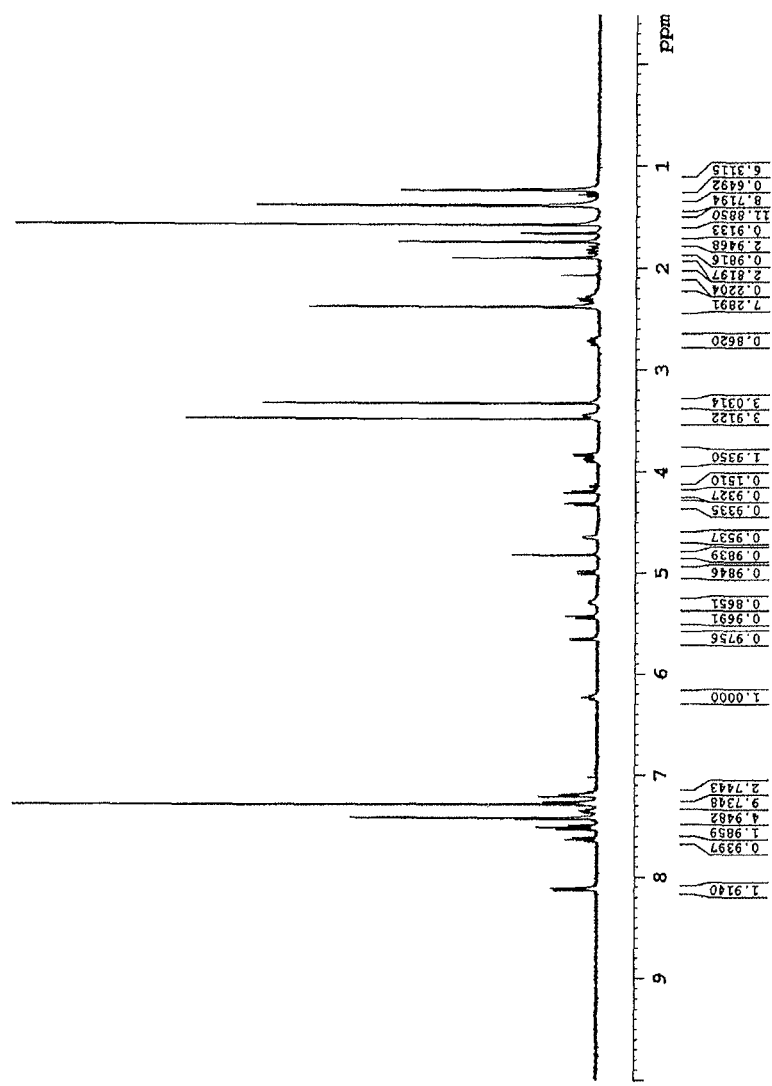
Figure 5d. ¹H NMR spectrum of cabazitaxel crystalline Form C4

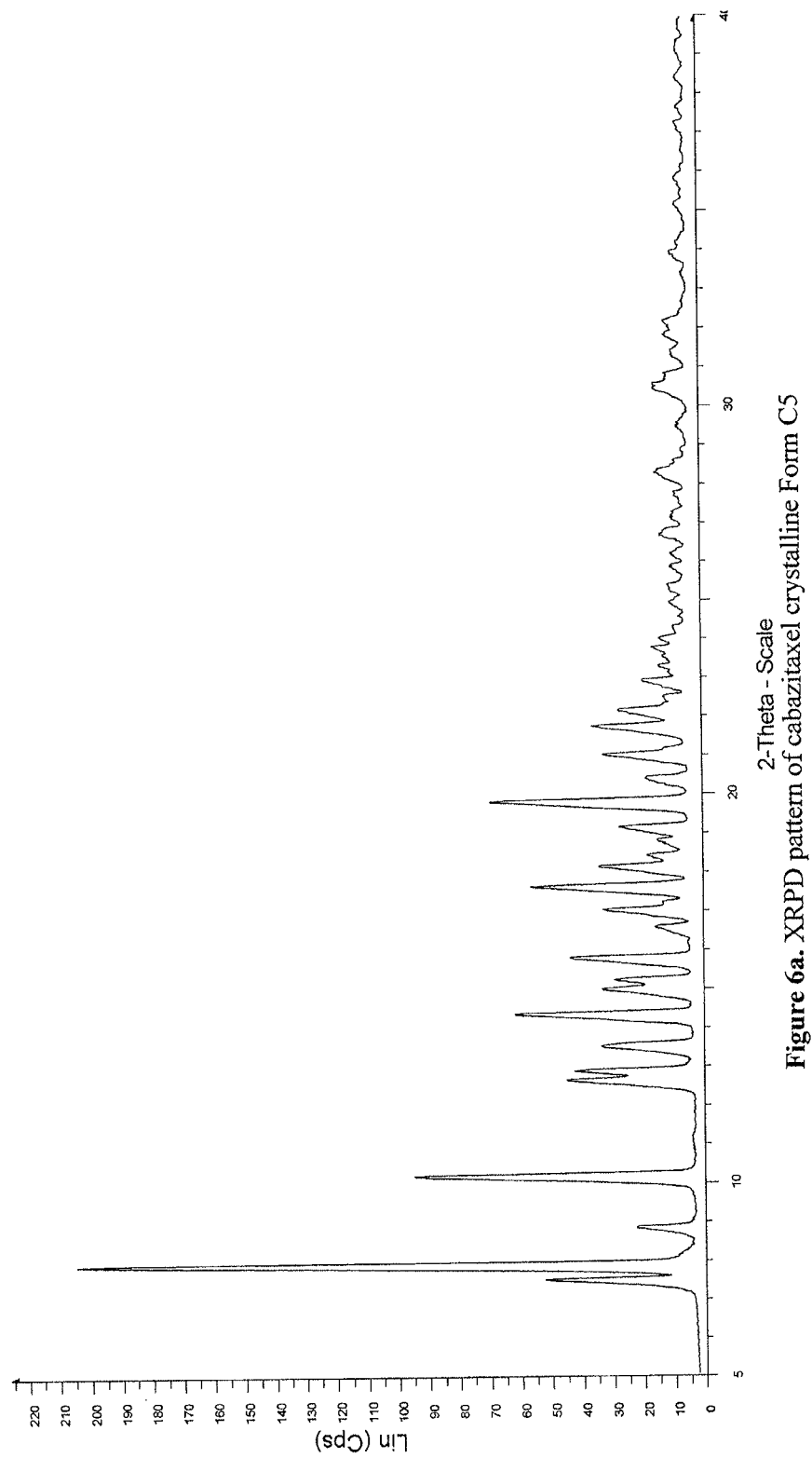
Figure 6a. XRPD pattern of cabazitaxel crystalline Form C5

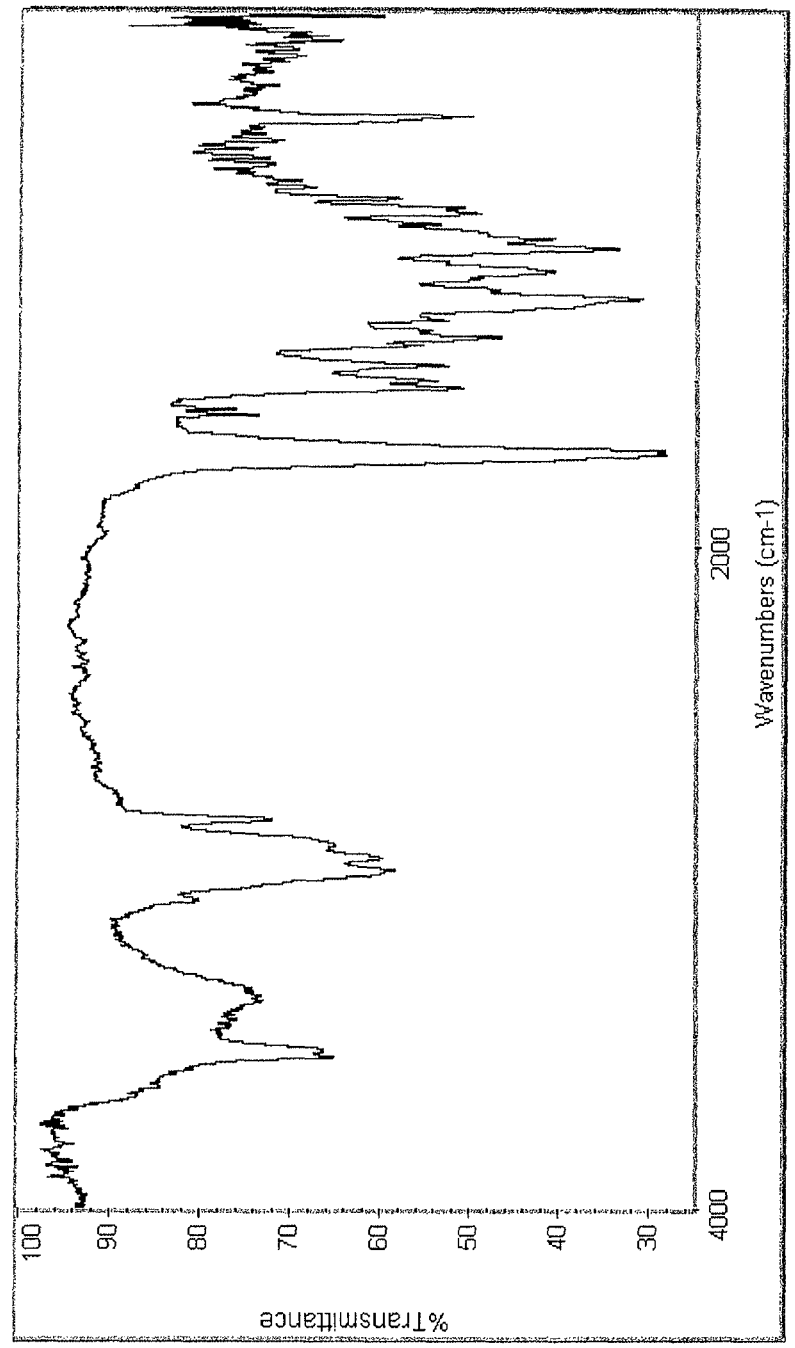
Figure 6b. IR spectrum of cabazitaxel crystalline Form C5

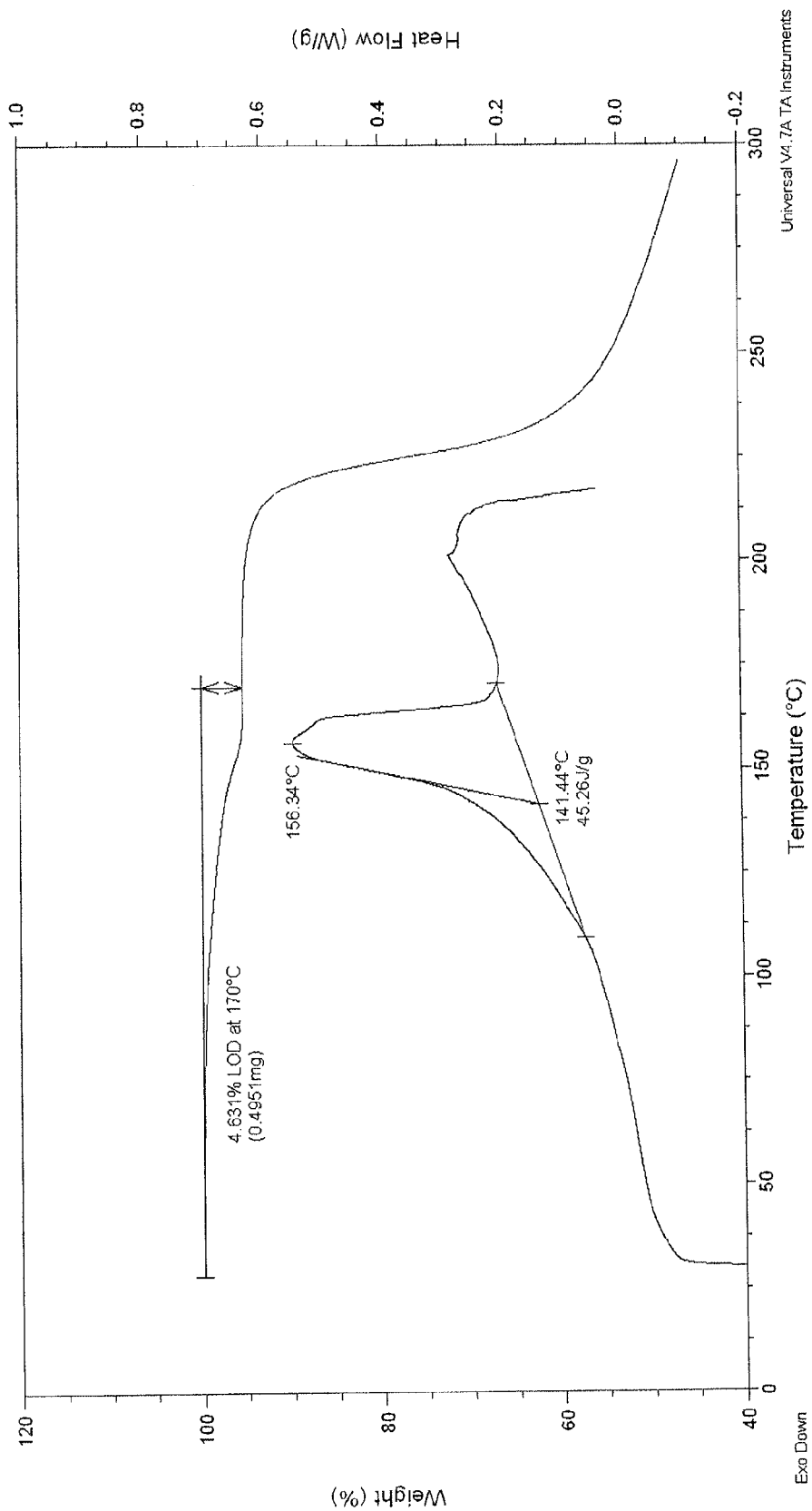
Figure 6c. DSC/TGA trace of cabazitaxel crystalline Form C5

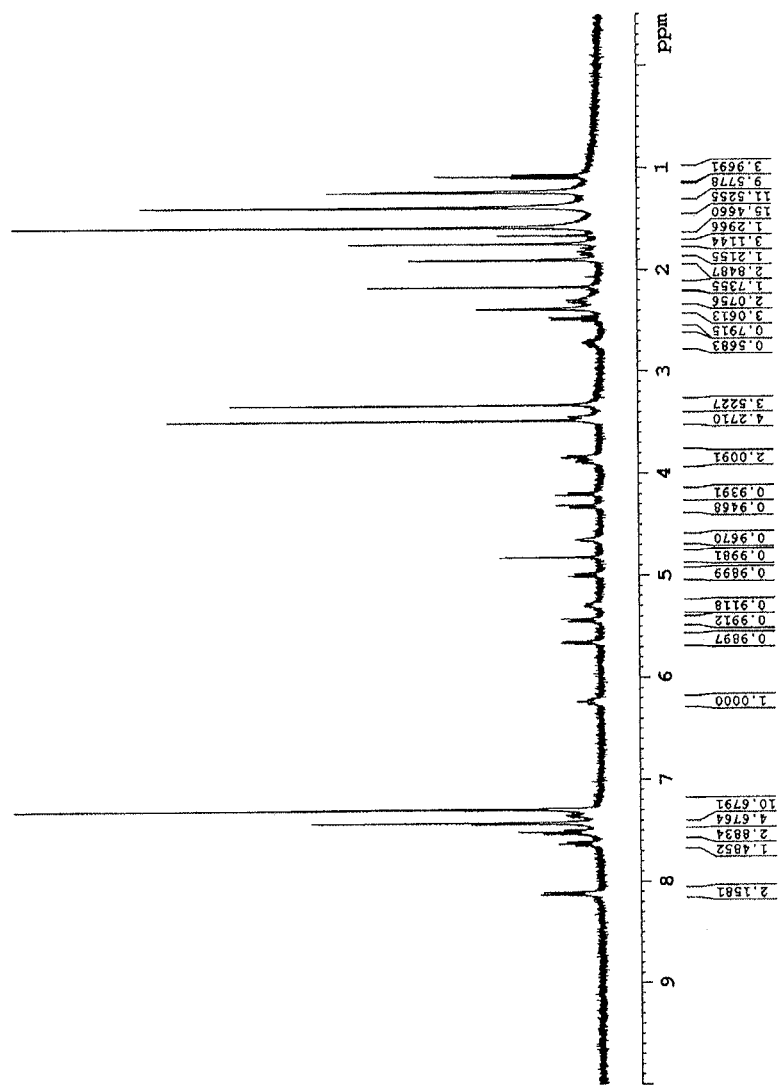
Figure 6d. $^1$H NMR spectrum of cabazitaxel crystalline Form C5

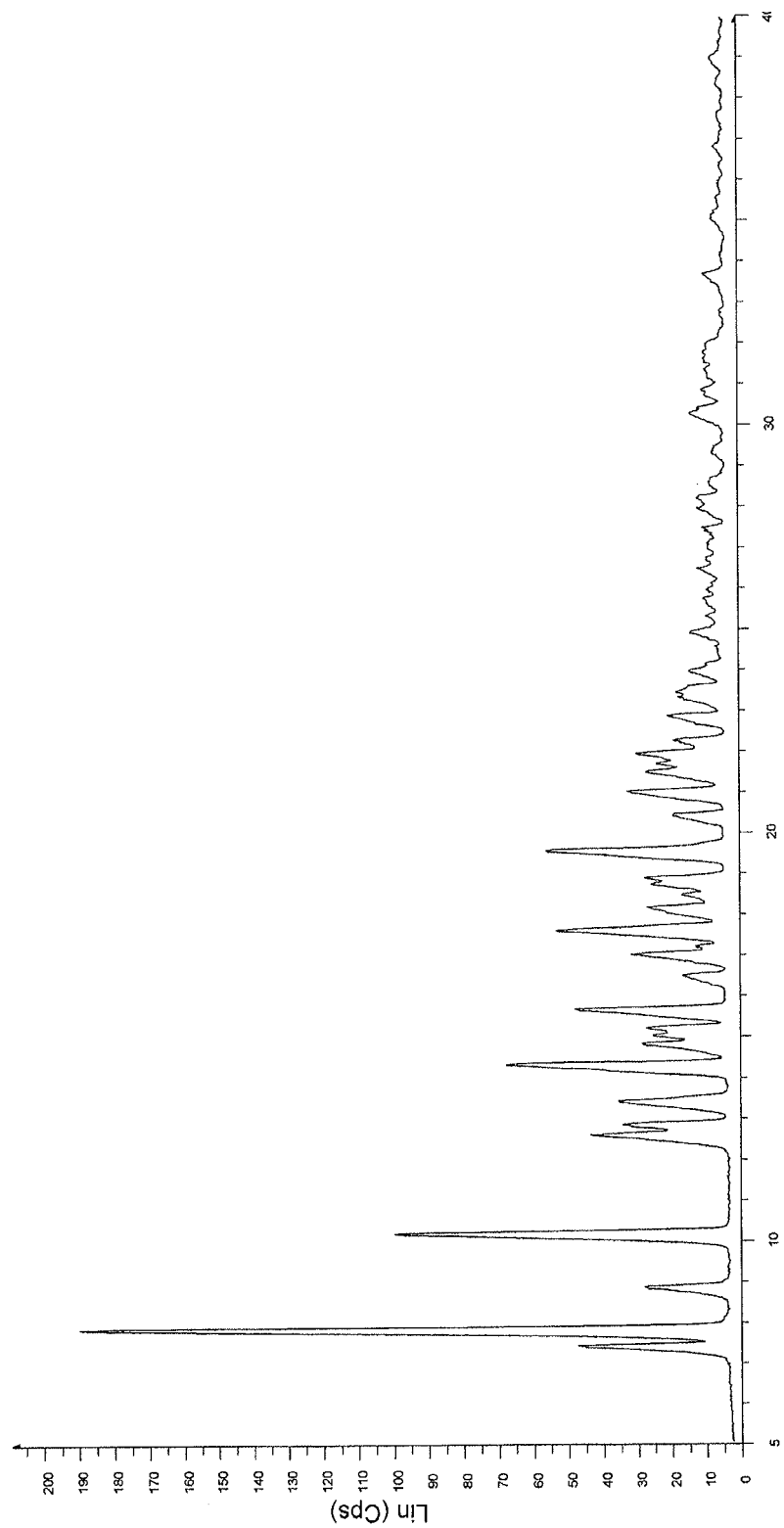
Figure 7a. XRPD pattern of cabazitaxel crystalline Form C6

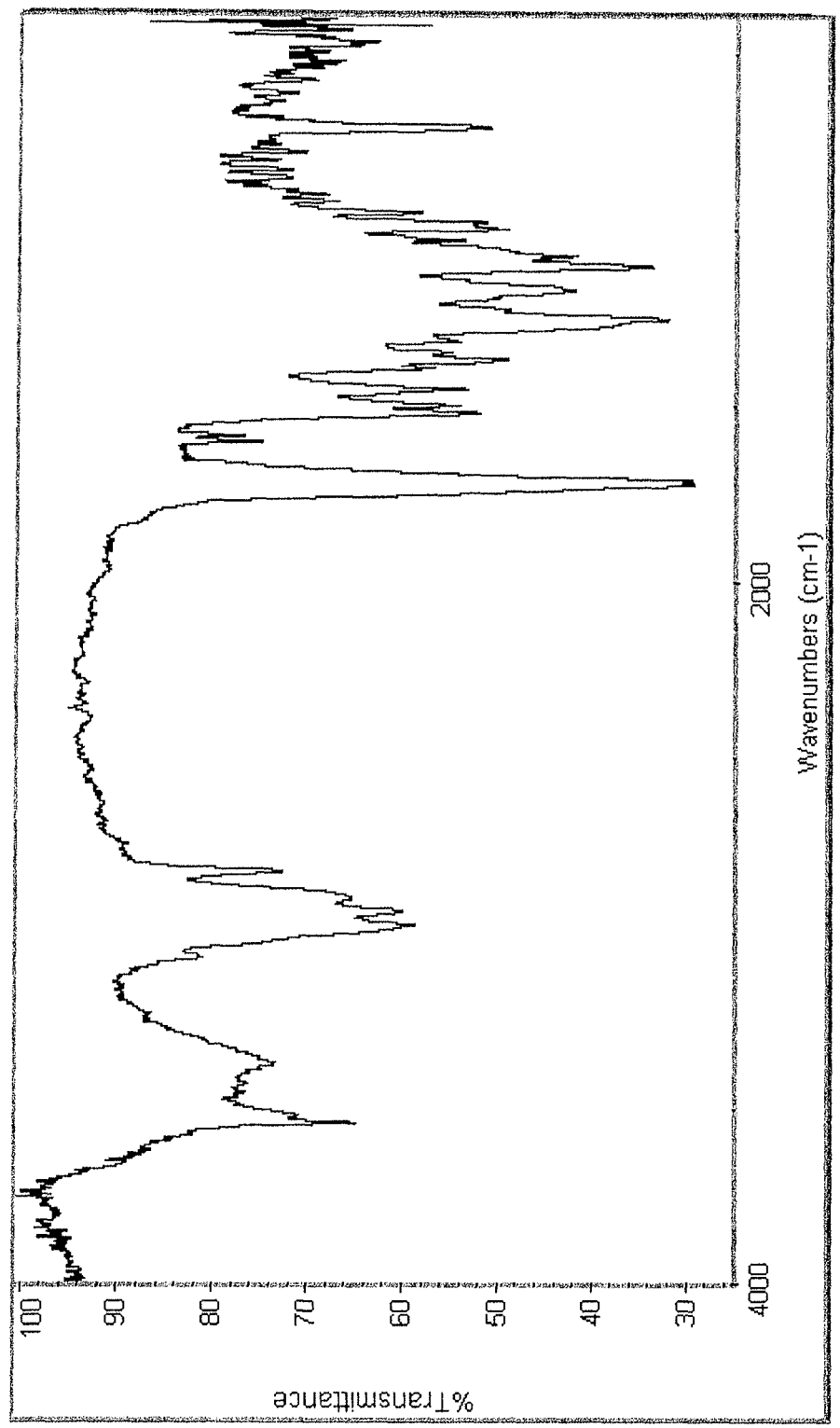
Figure 7b. IR spectrum of cabazitaxel crystalline Form C6

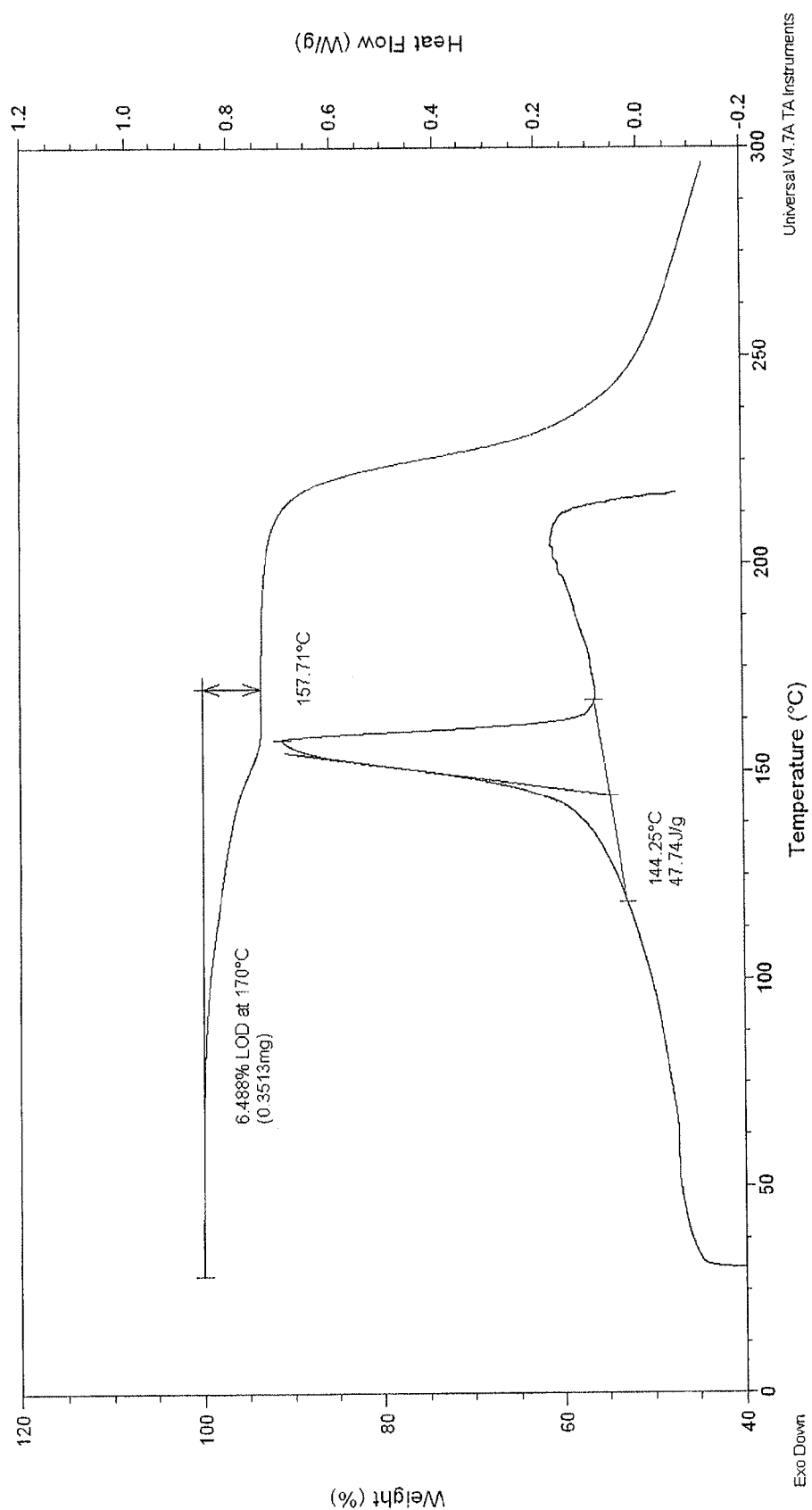
Figure 7c. DSC/TGA trace of cabazitaxel crystalline Form C6

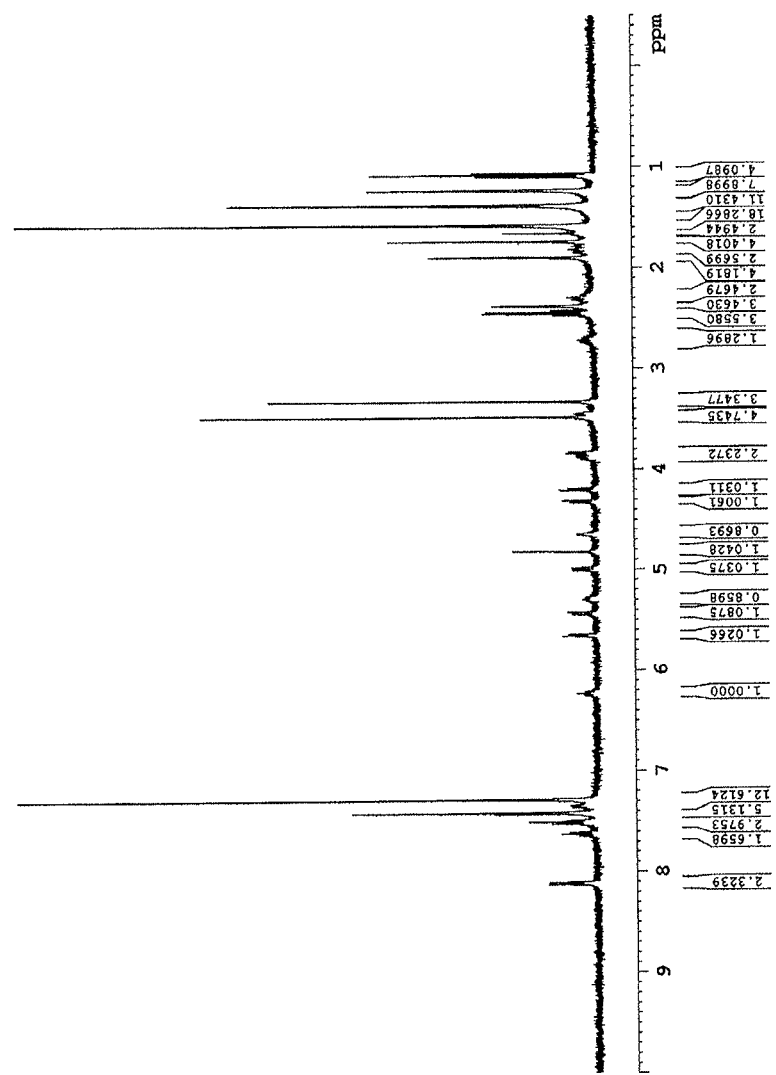
Figure 7d. ¹H NMR spectrum of cabazitaxel crystalline Form C6

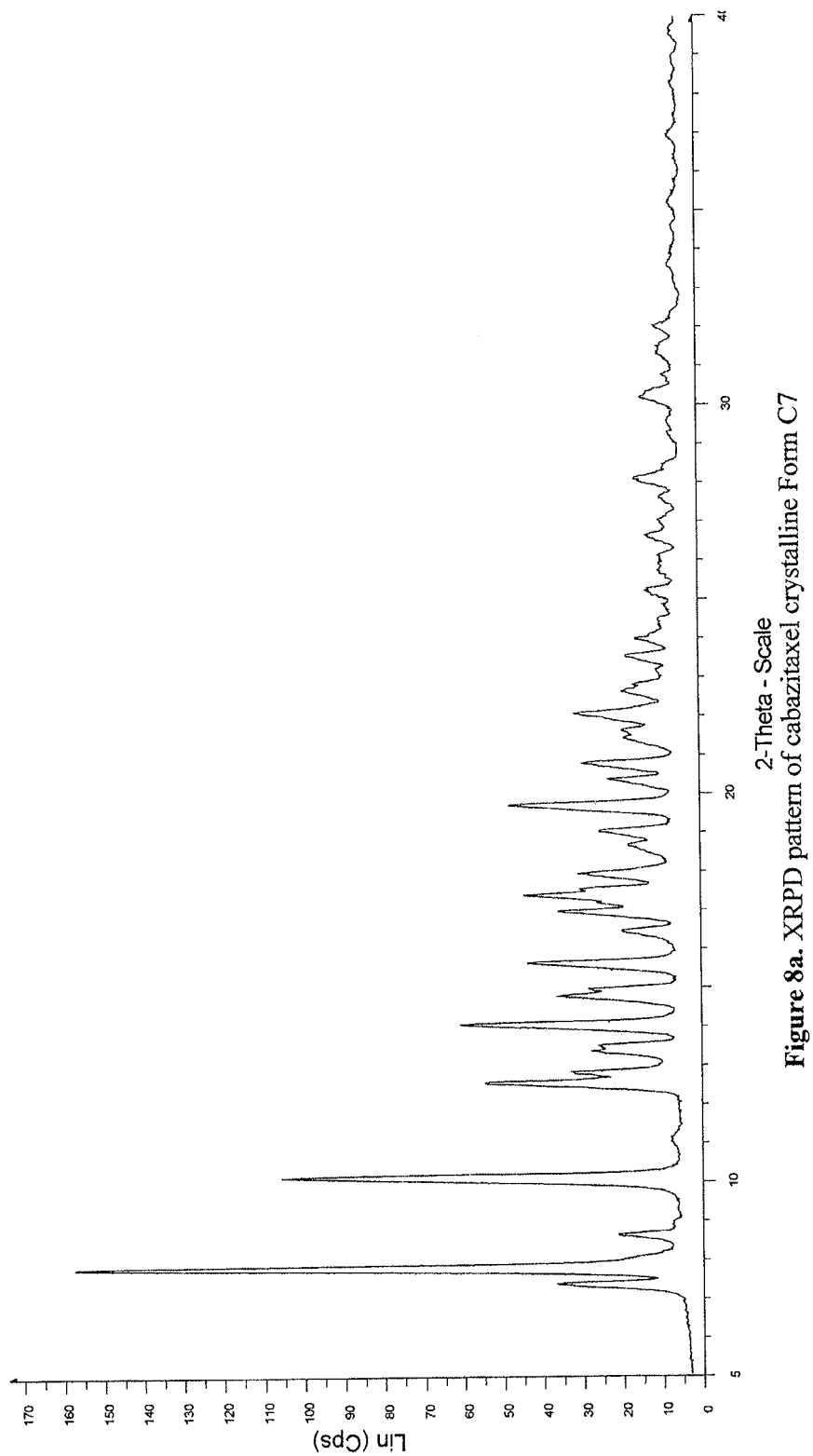
Figure 8a. XRPD pattern of cabazitaxel crystalline Form C7

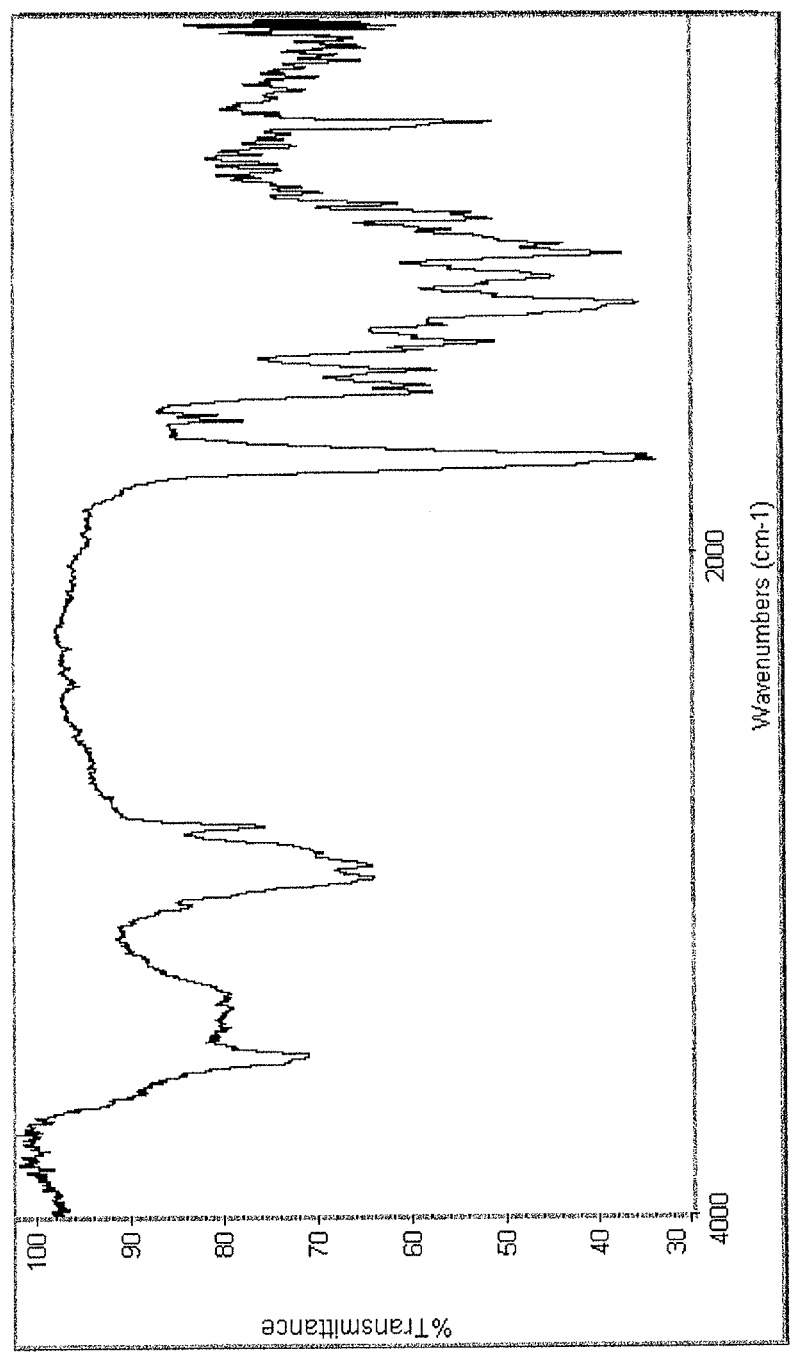
Figure 8b. IR spectrum of cabazitaxel crystalline Form C7

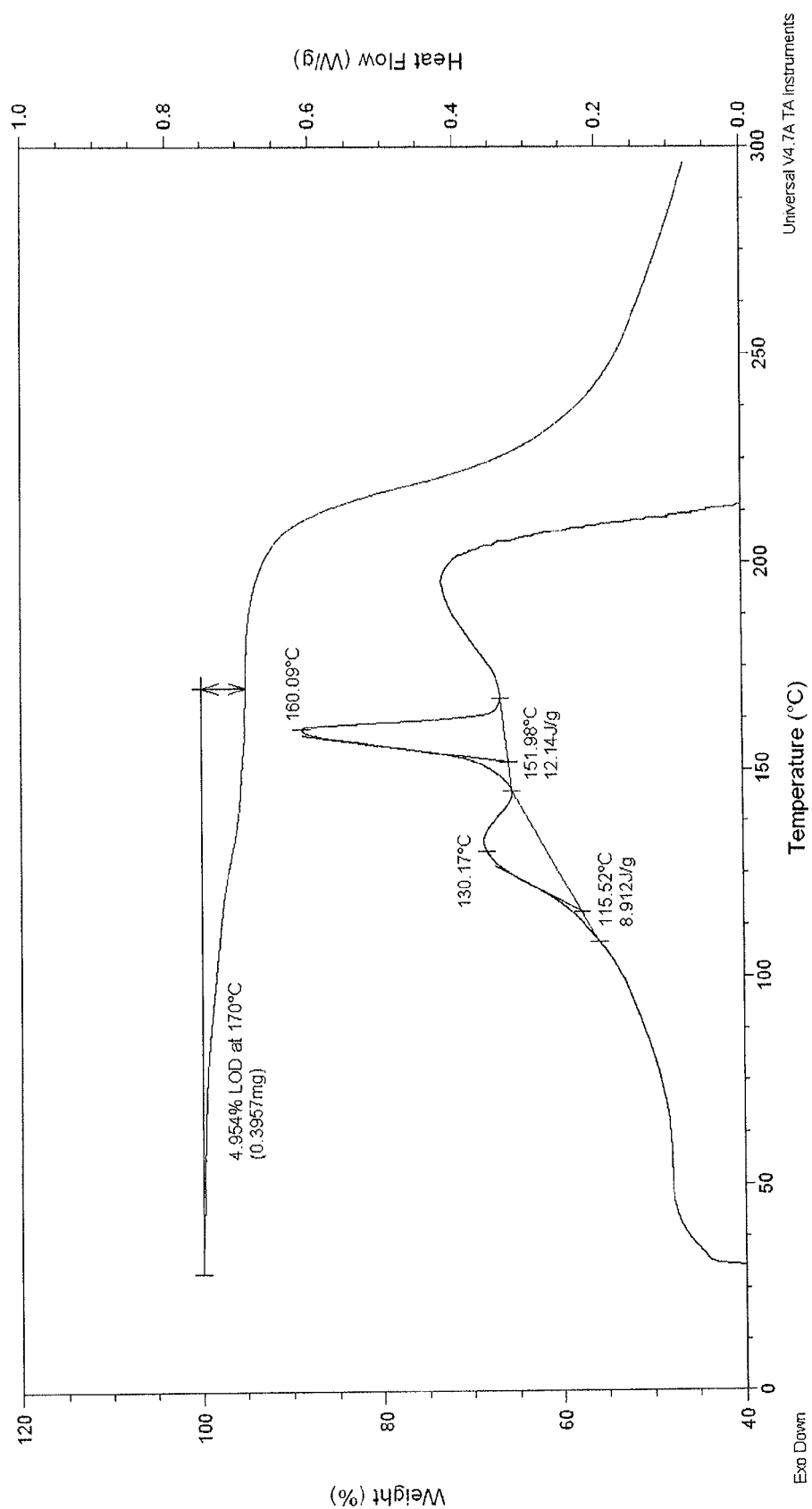
Figure 8c. DSC/TGA trace of cabazitaxel crystalline Form C7

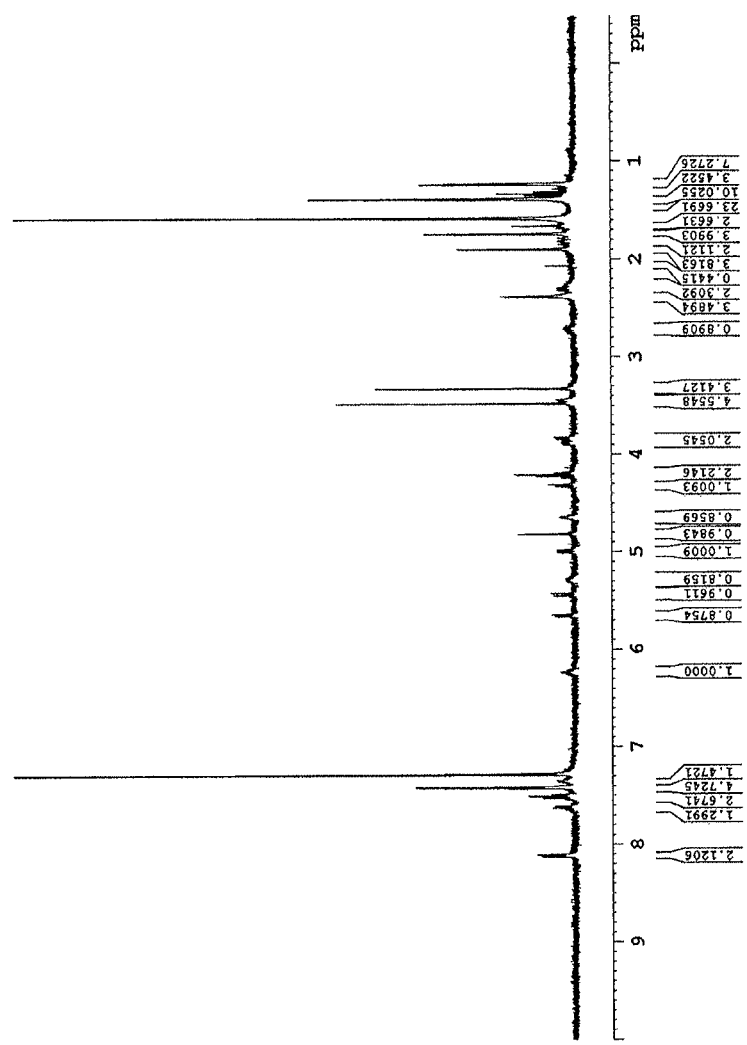
Figure 8d. ¹H NMR spectrum of cabazitaxel crystalline Form C7

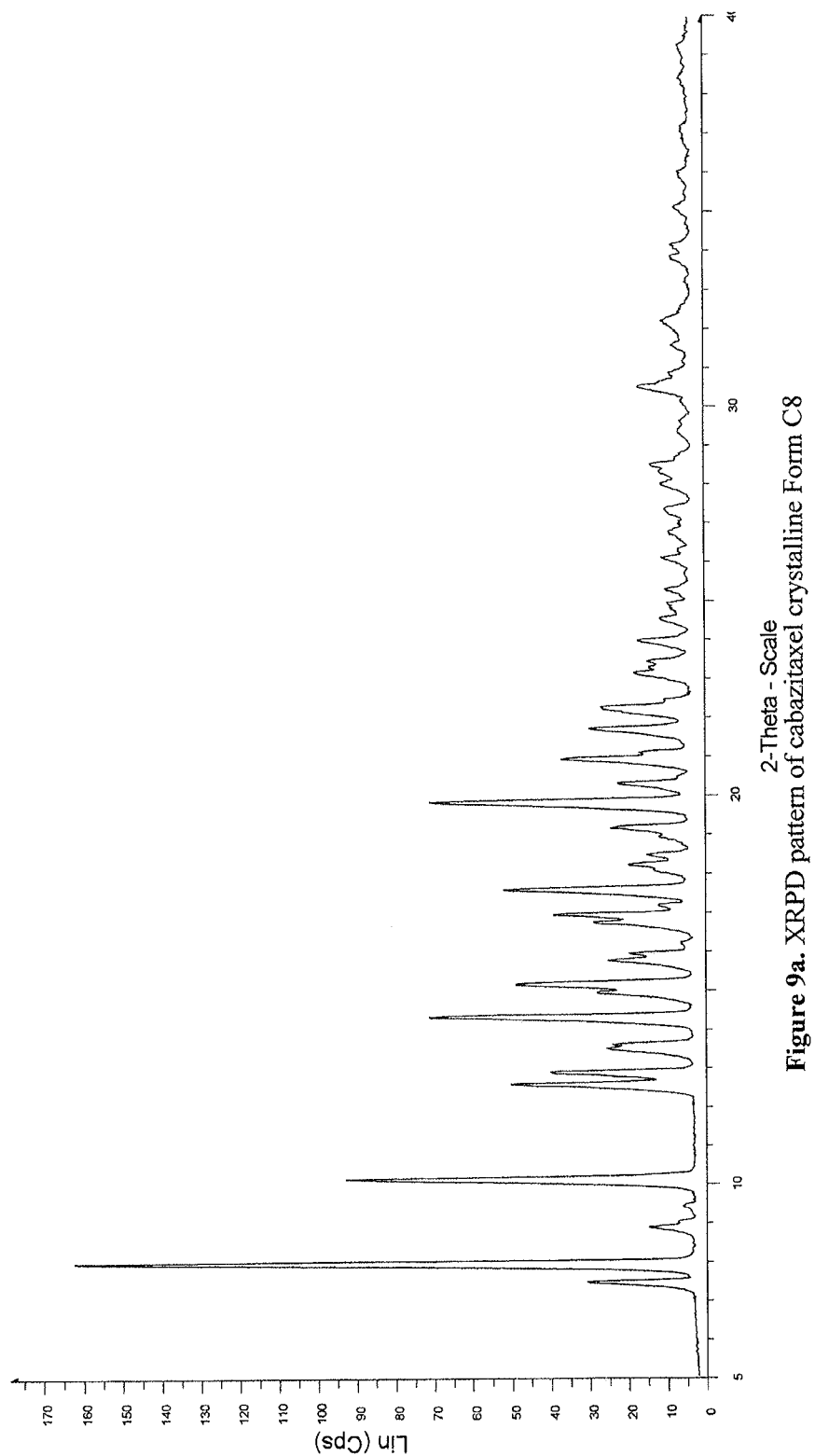
Figure 9a. XRPD pattern of cabazitaxel crystalline Form C8

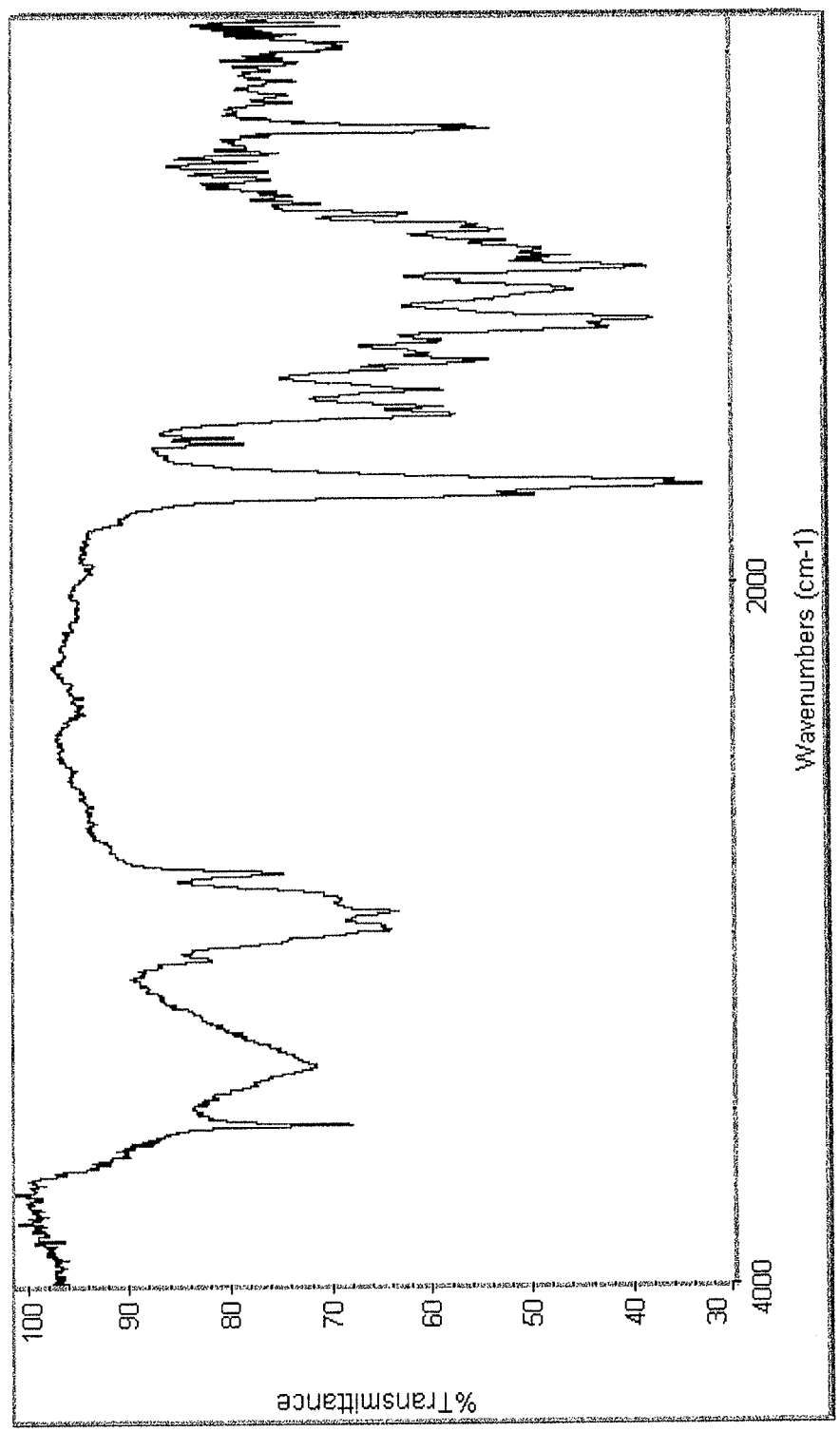
Figure 9b. IR spectrum of cabazitaxel crystalline Form C8

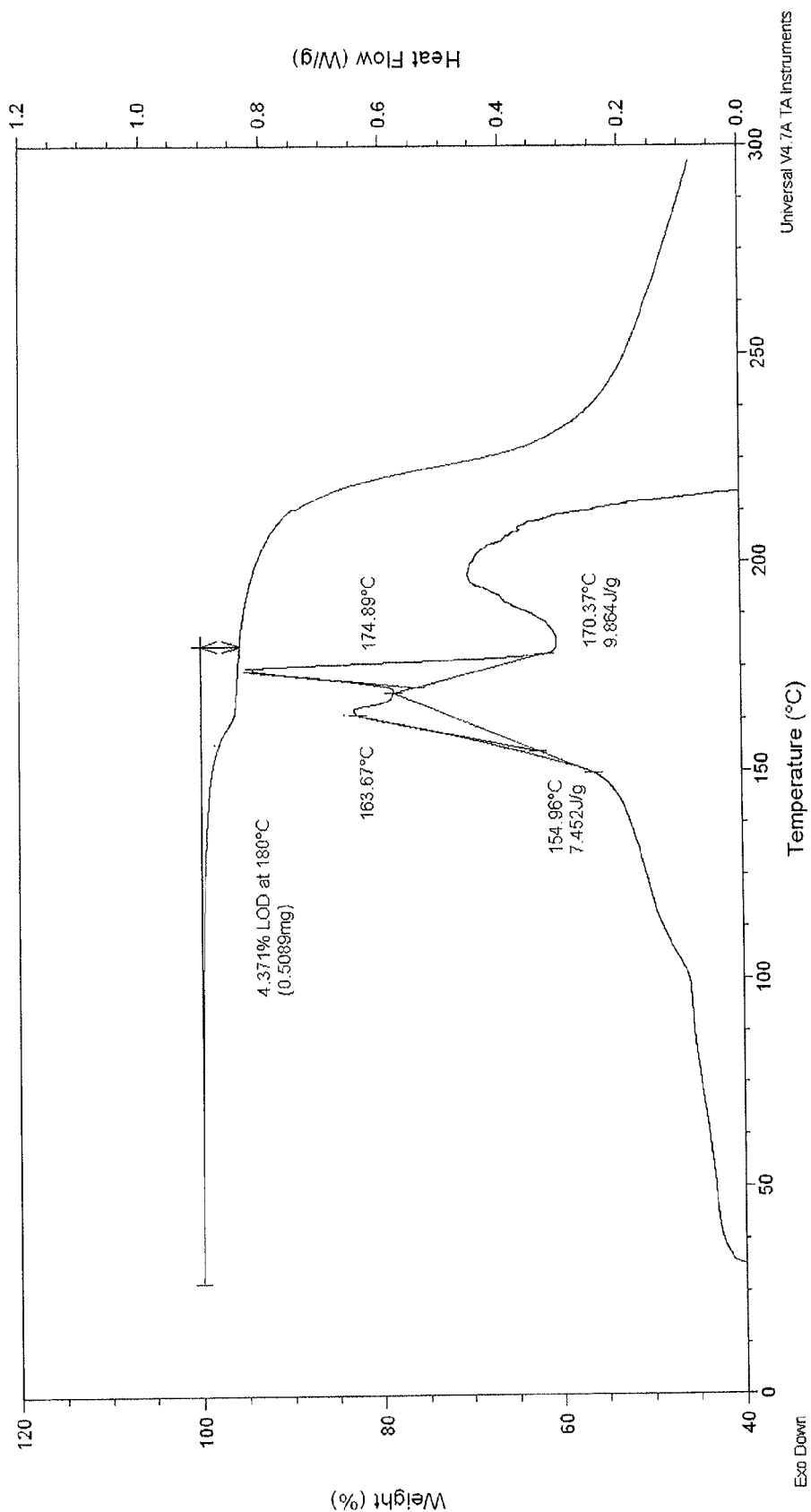
Figure 9c. DSC/TGA trace of cabazitaxel crystalline Form C8

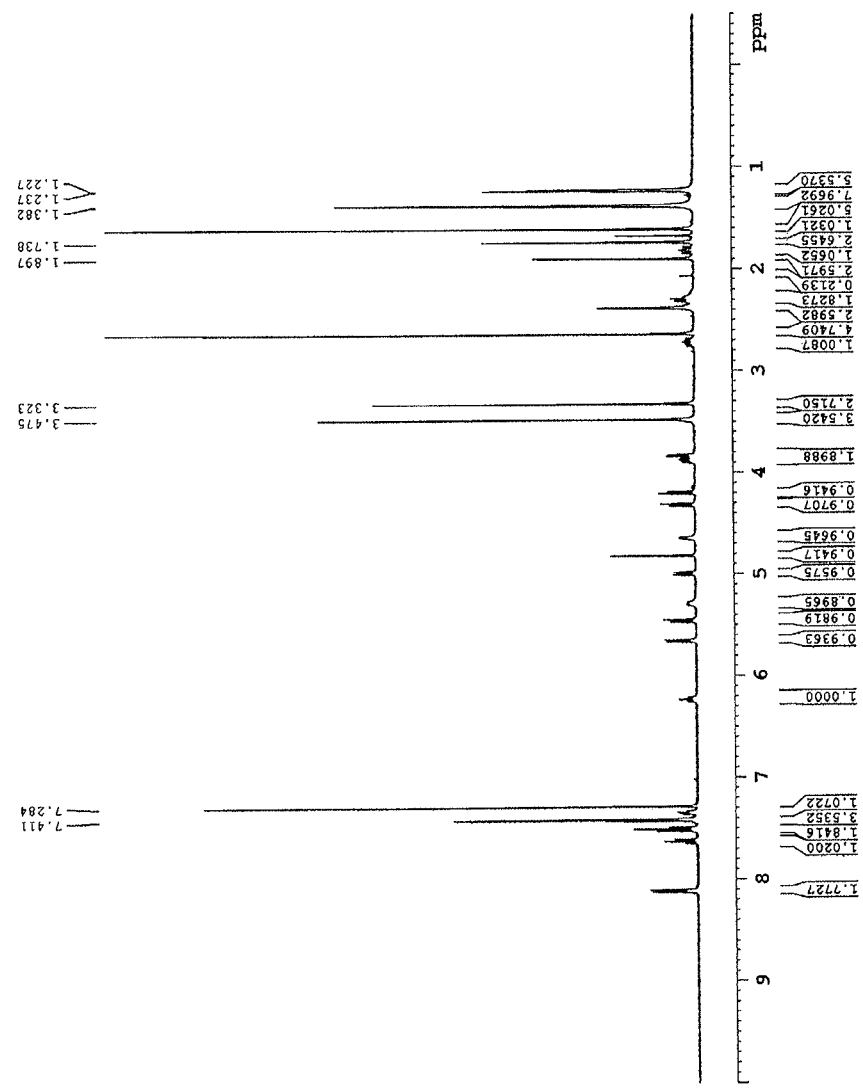
Figure 9d. $^1$H NMR spectrum of cabazitaxel crystalline Form C8

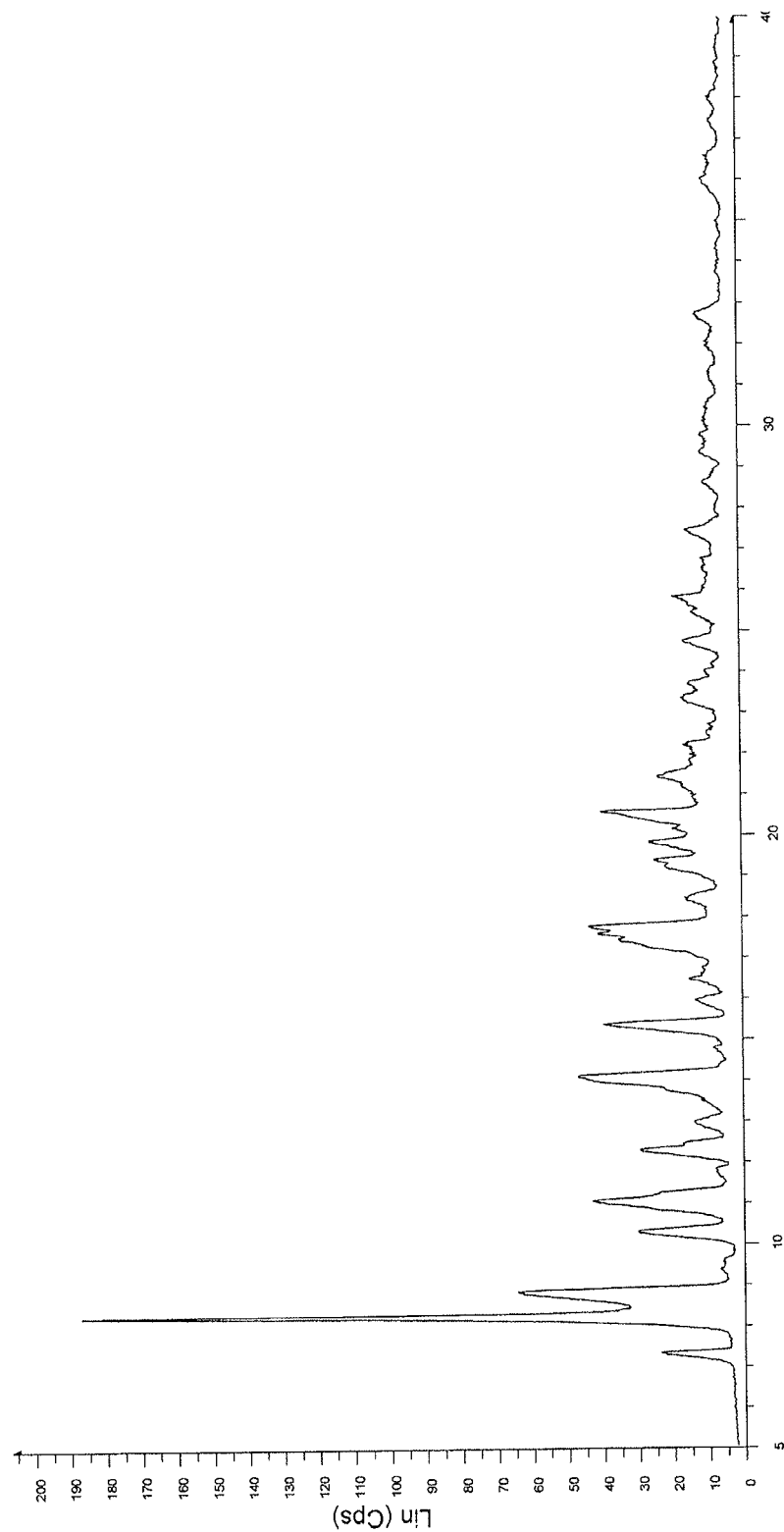
Figure 10a. XRPD pattern of cabazitaxel crystalline Form C9

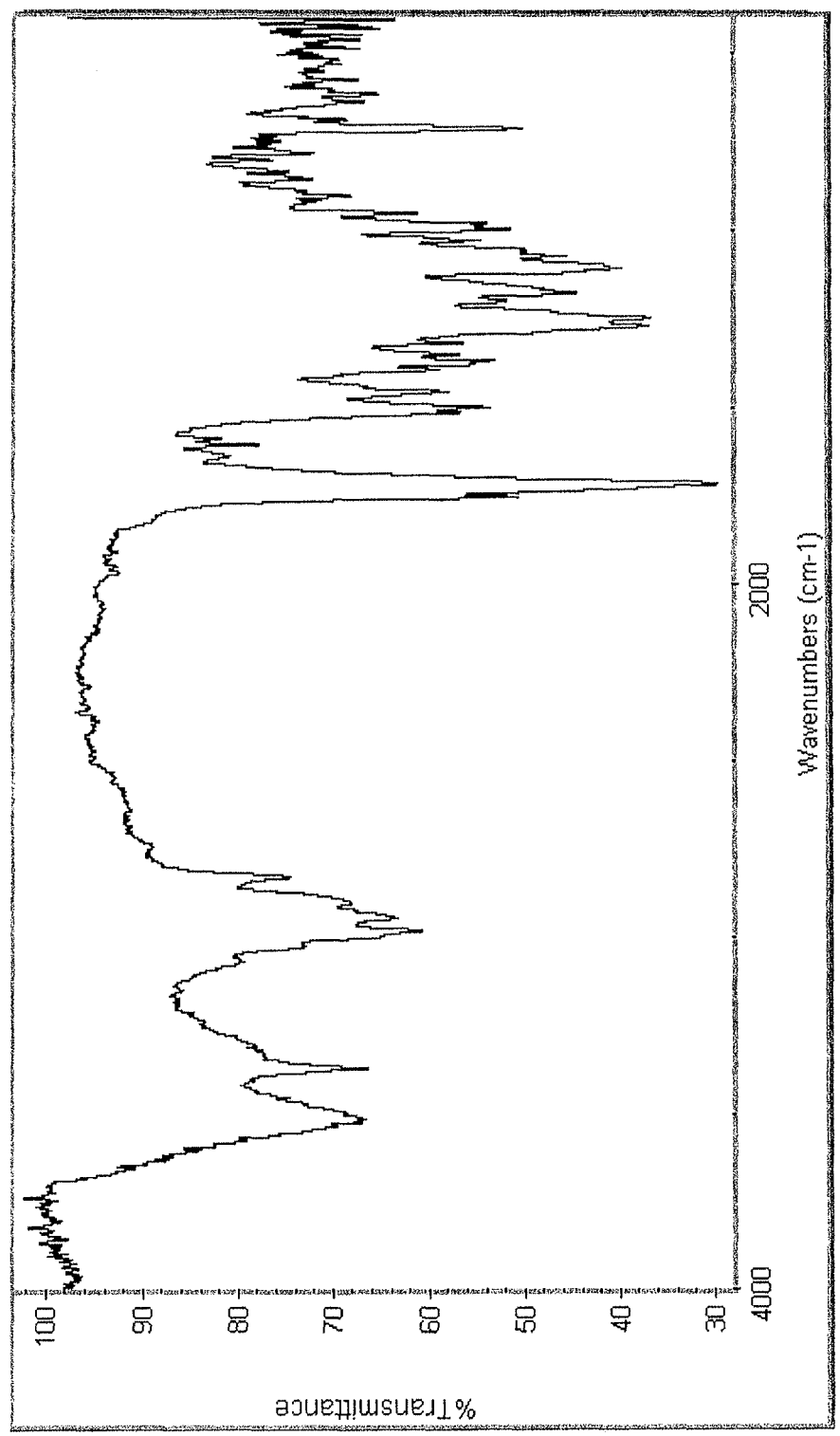
Figure 10b. IR spectrum of cabazitaxel crystalline Form C9

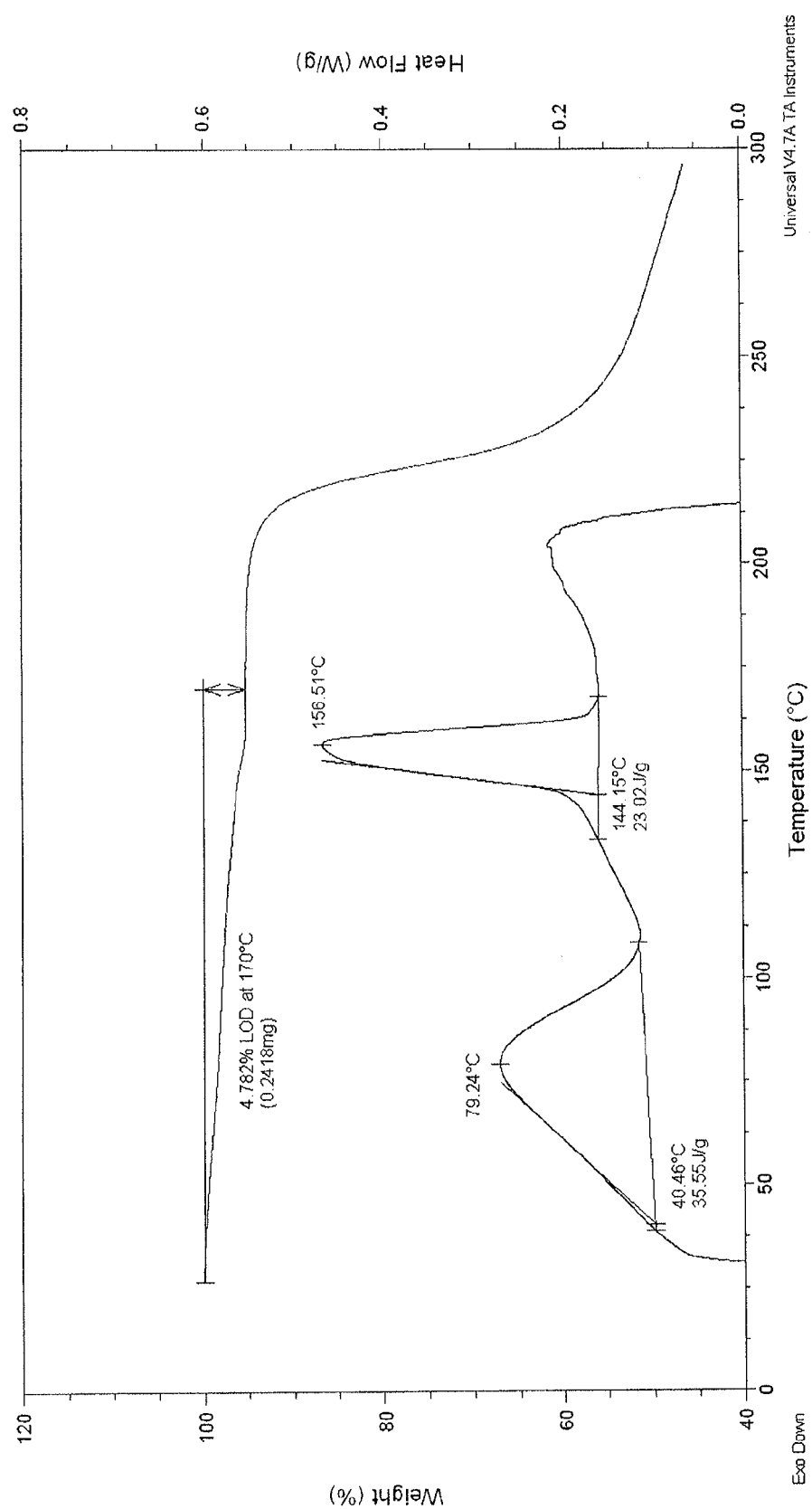
Figure 10c. DSC/TGA trace spectrum of cabazitaxel crystalline Form C9

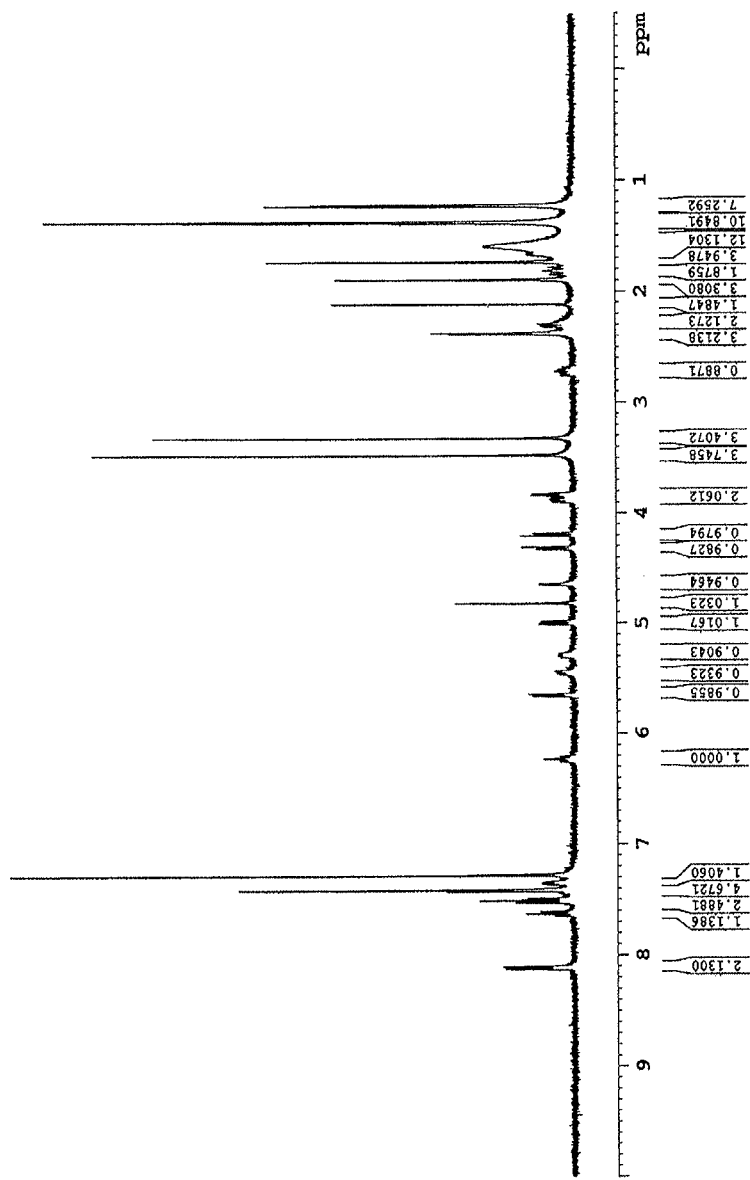
Figure 10d. $^1$H NMR spectrum of cabazitaxel crystalline Form C9

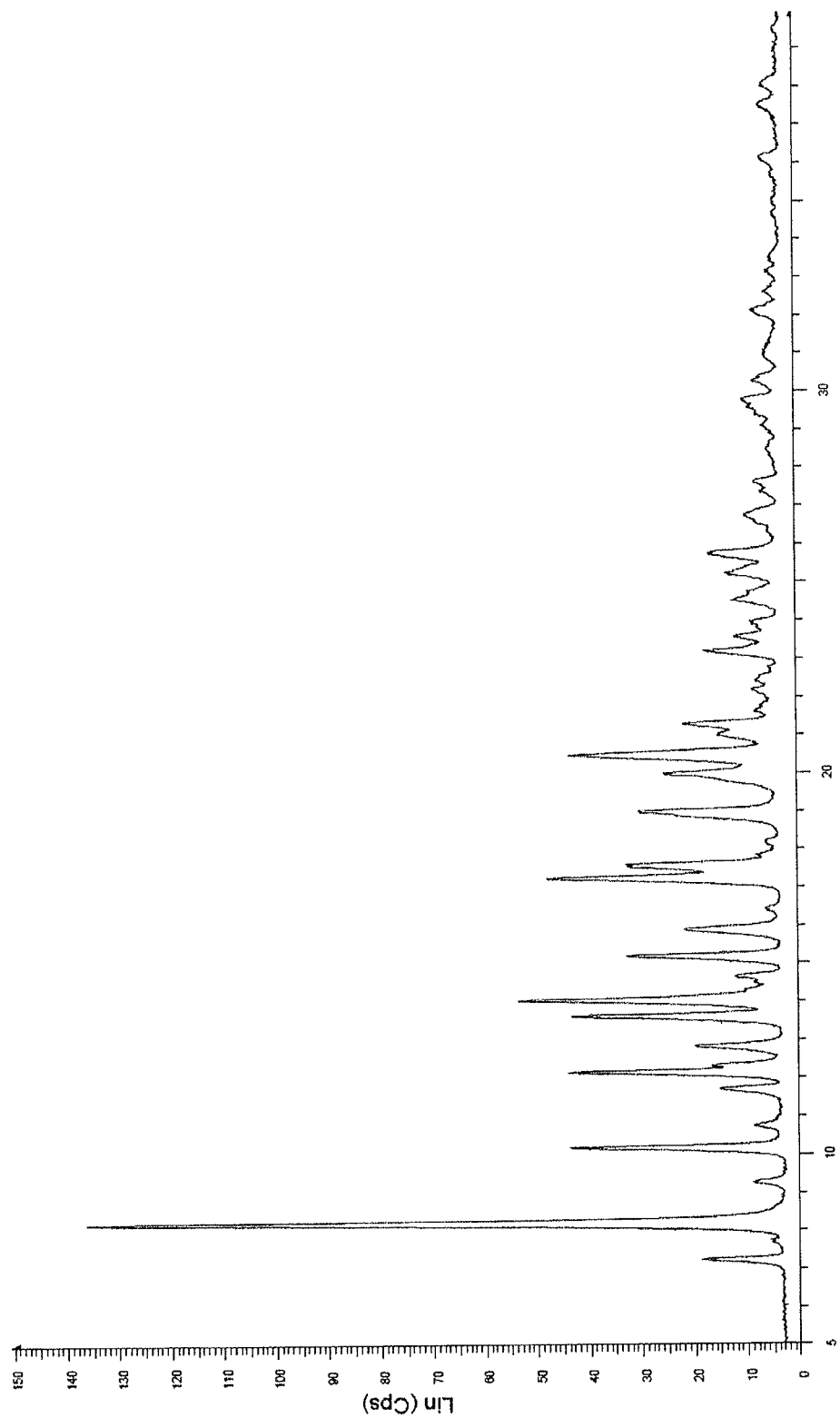
Figure 11a. XRPD pattern of cabazitaxel crystalline Form C8b

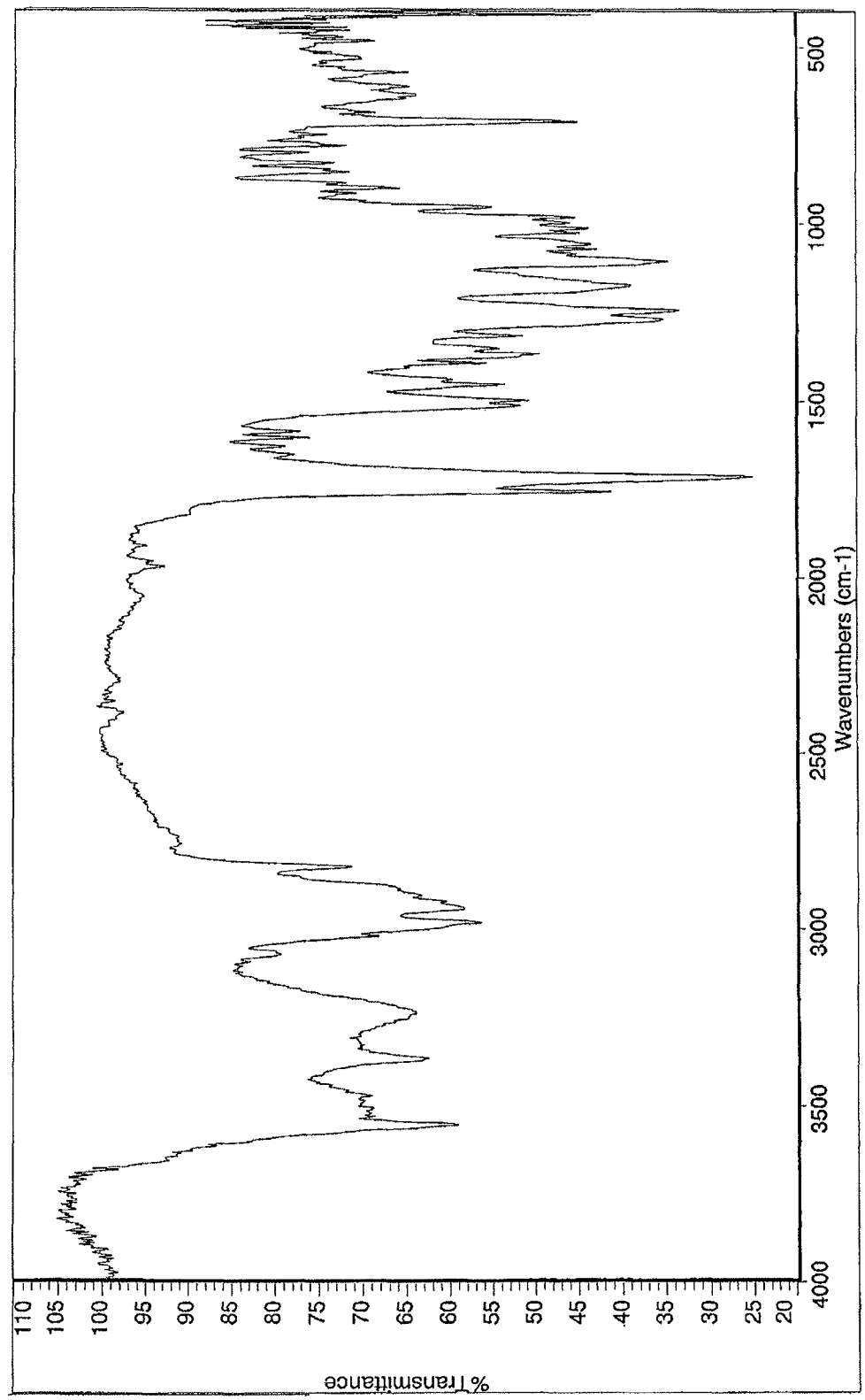
Figure 11b. IR spectrum of cabazitaxel crystalline Form C8b

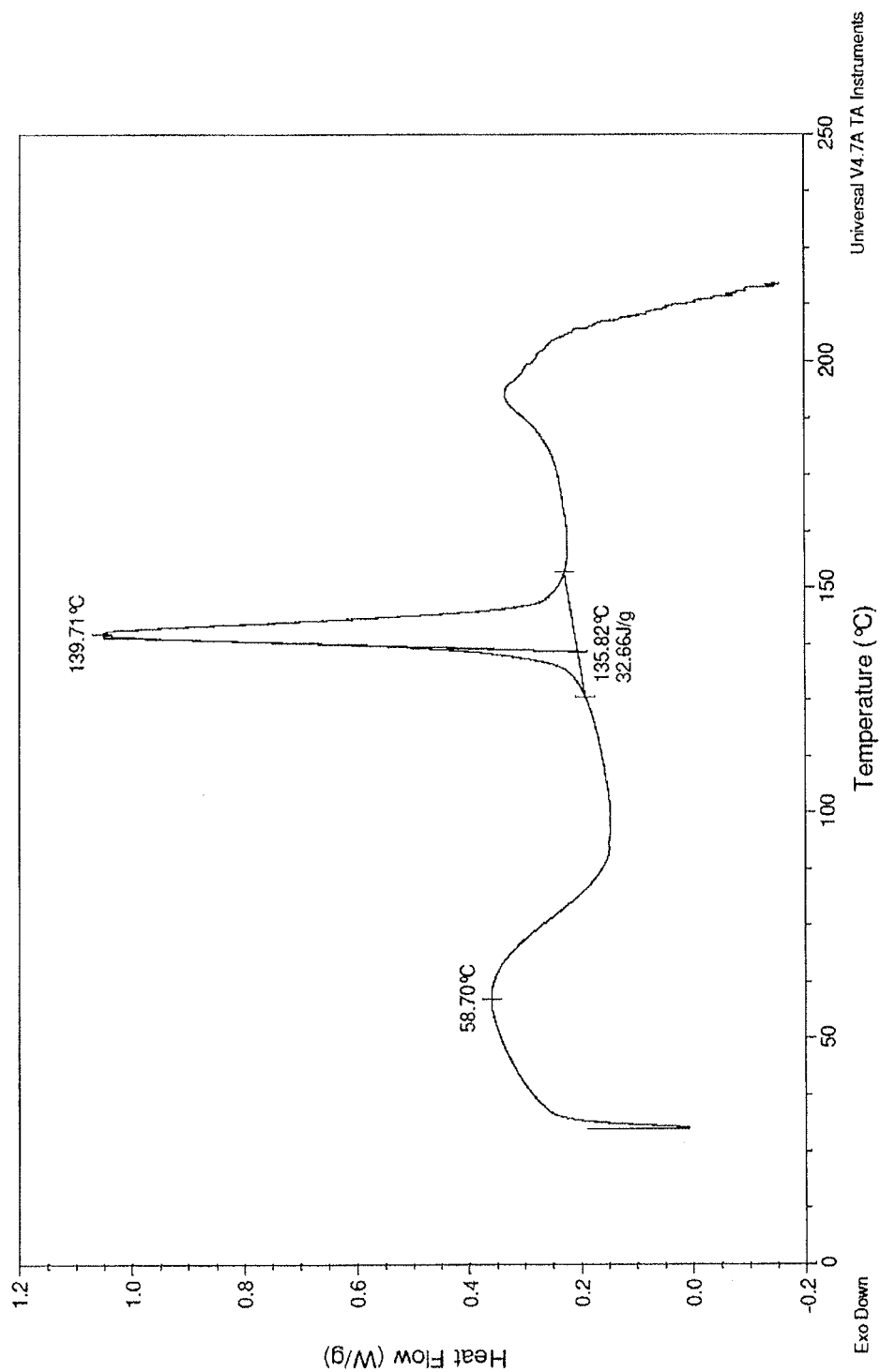
Figure 11c. DSC trace of cabazitaxel crystalline Form C8b

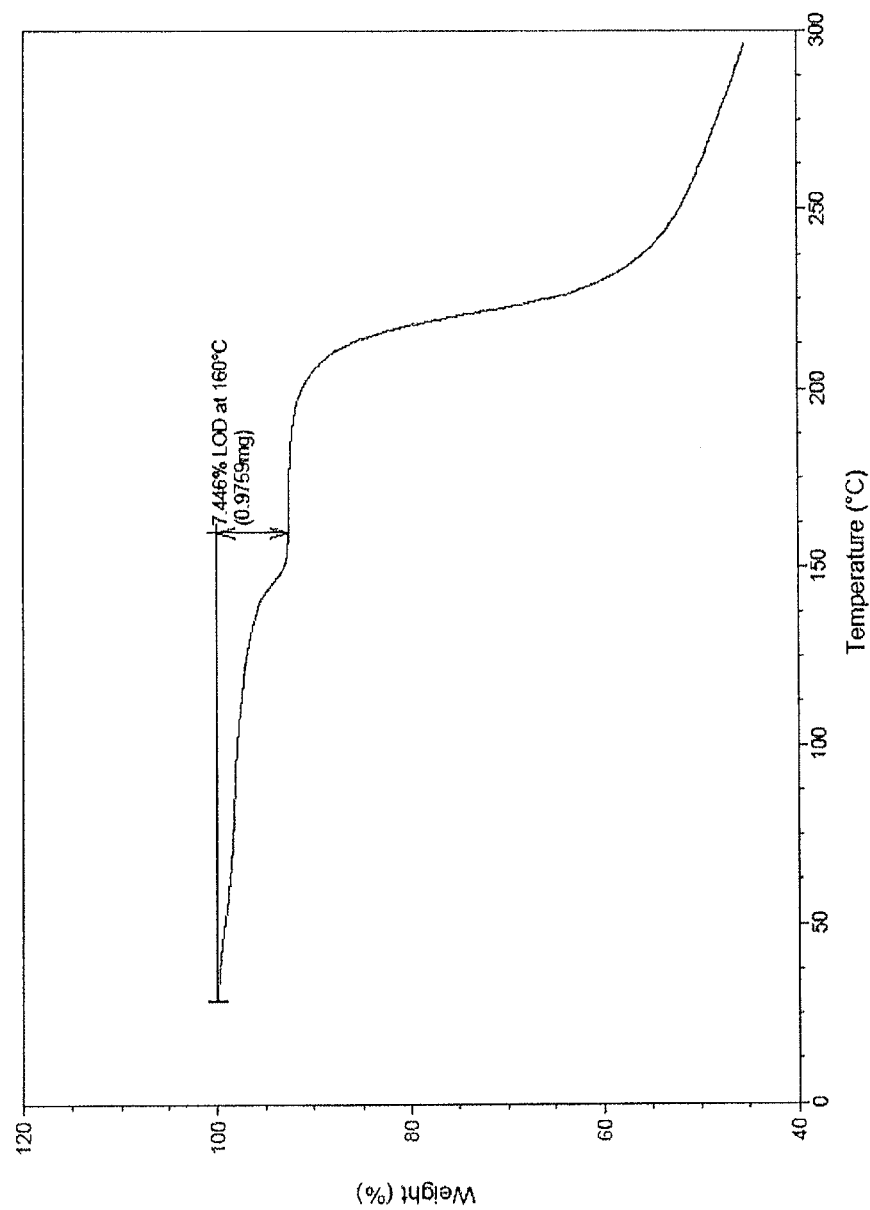
Figure 11d. TGA trace of cabazitaxel crystalline Form C8b

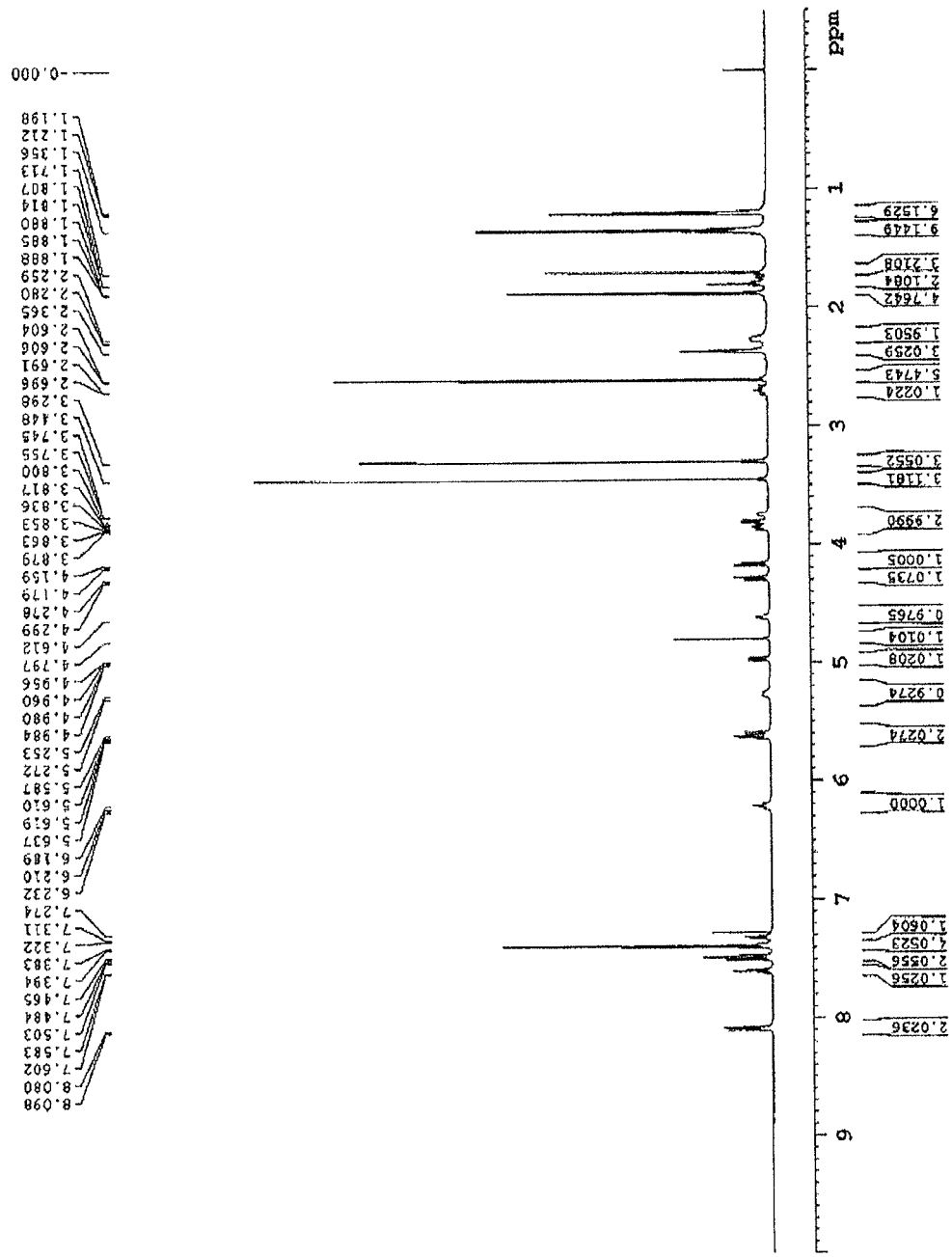
Figure 11e. ¹H NMR trace of cabazitaxel crystalline Form C8b

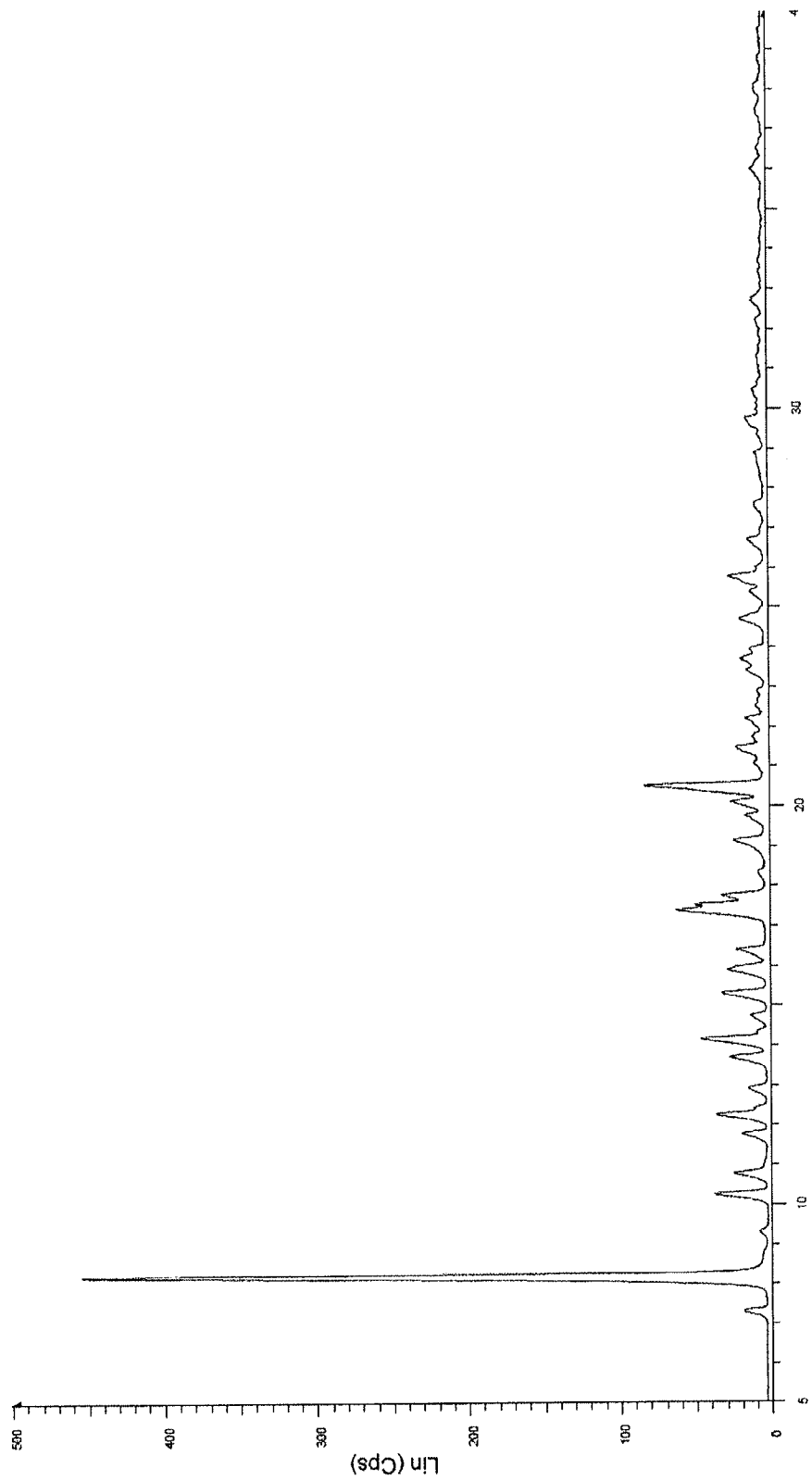
Figure 12a. XRPD pattern of cabazitaxel crystalline Form C9p

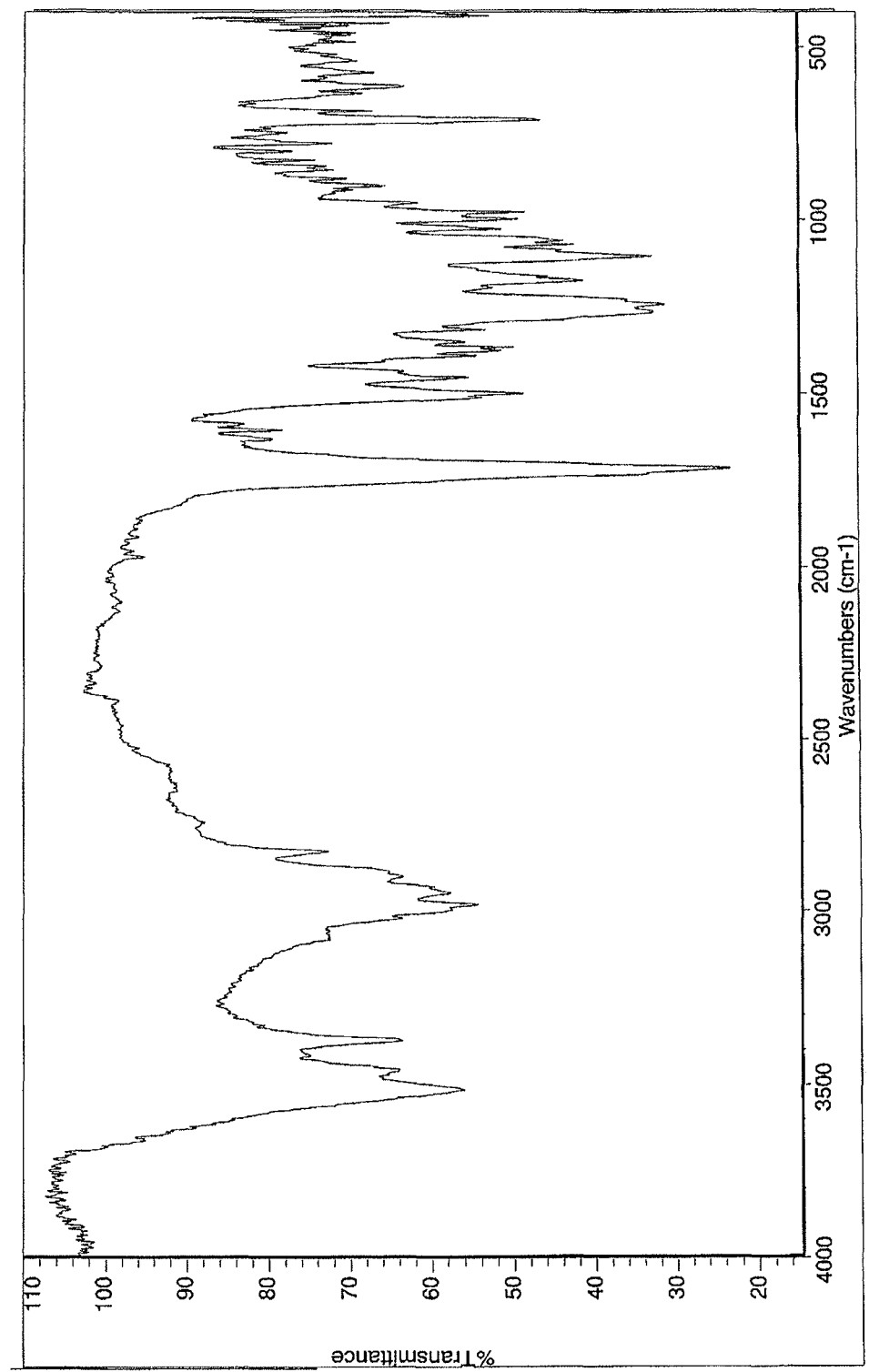
Figure 12b. IR spectrum of cabazitaxel crystalline Form C9p

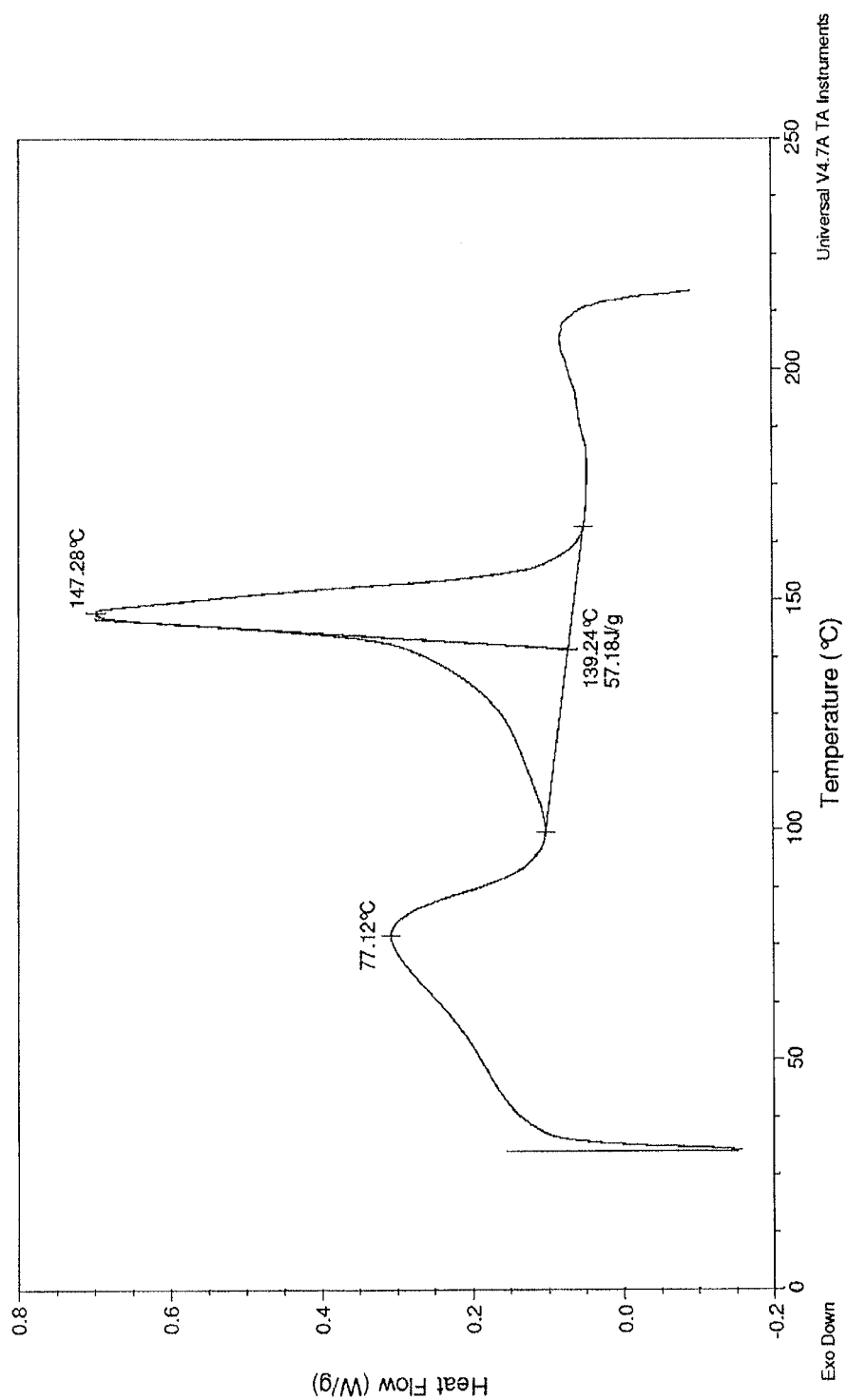
Figure 12c. DSC trace of cabazitaxel crystalline Form C9p

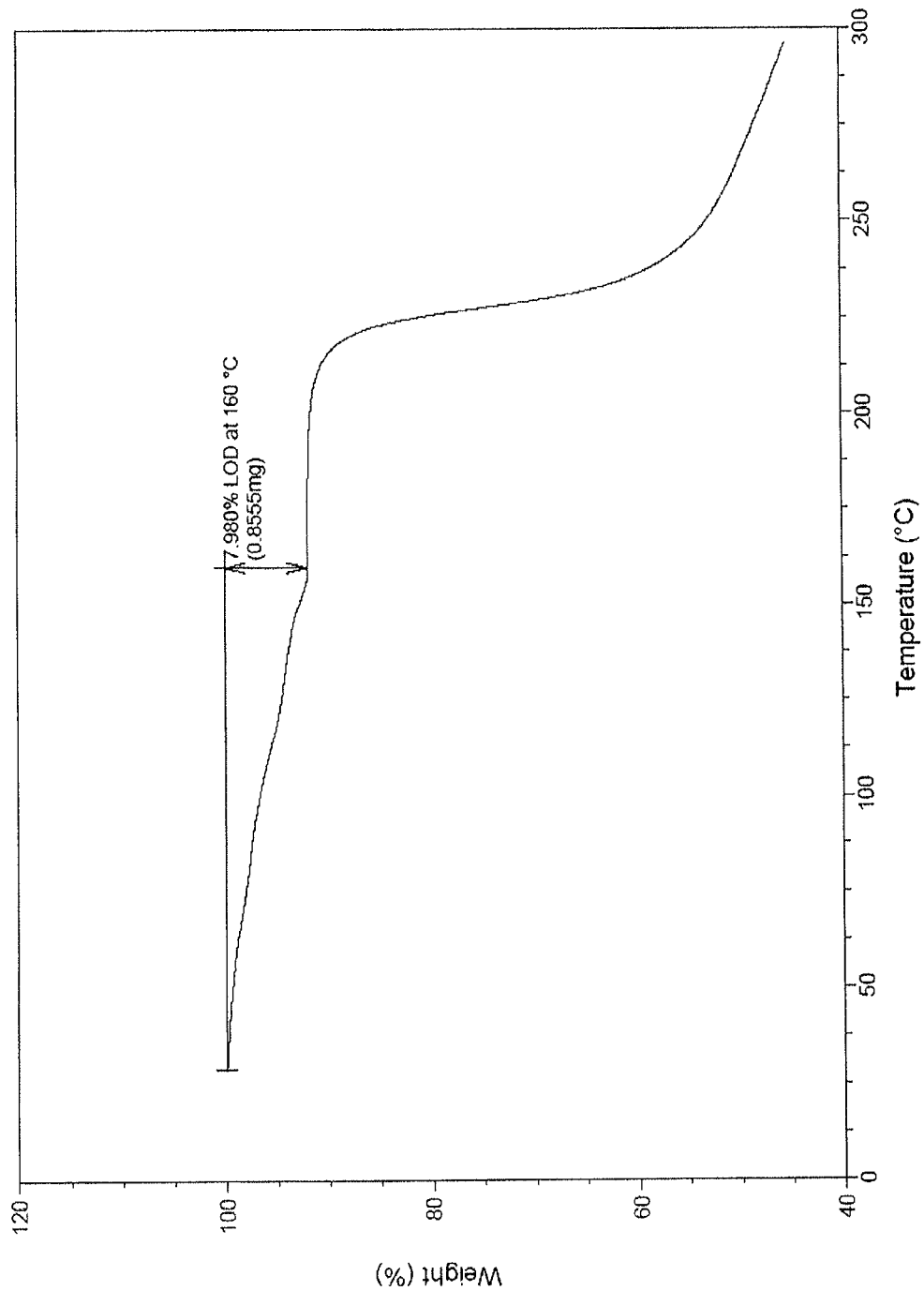
Figure 12d. TGA trace of cabazitaxel crystalline Form C9p

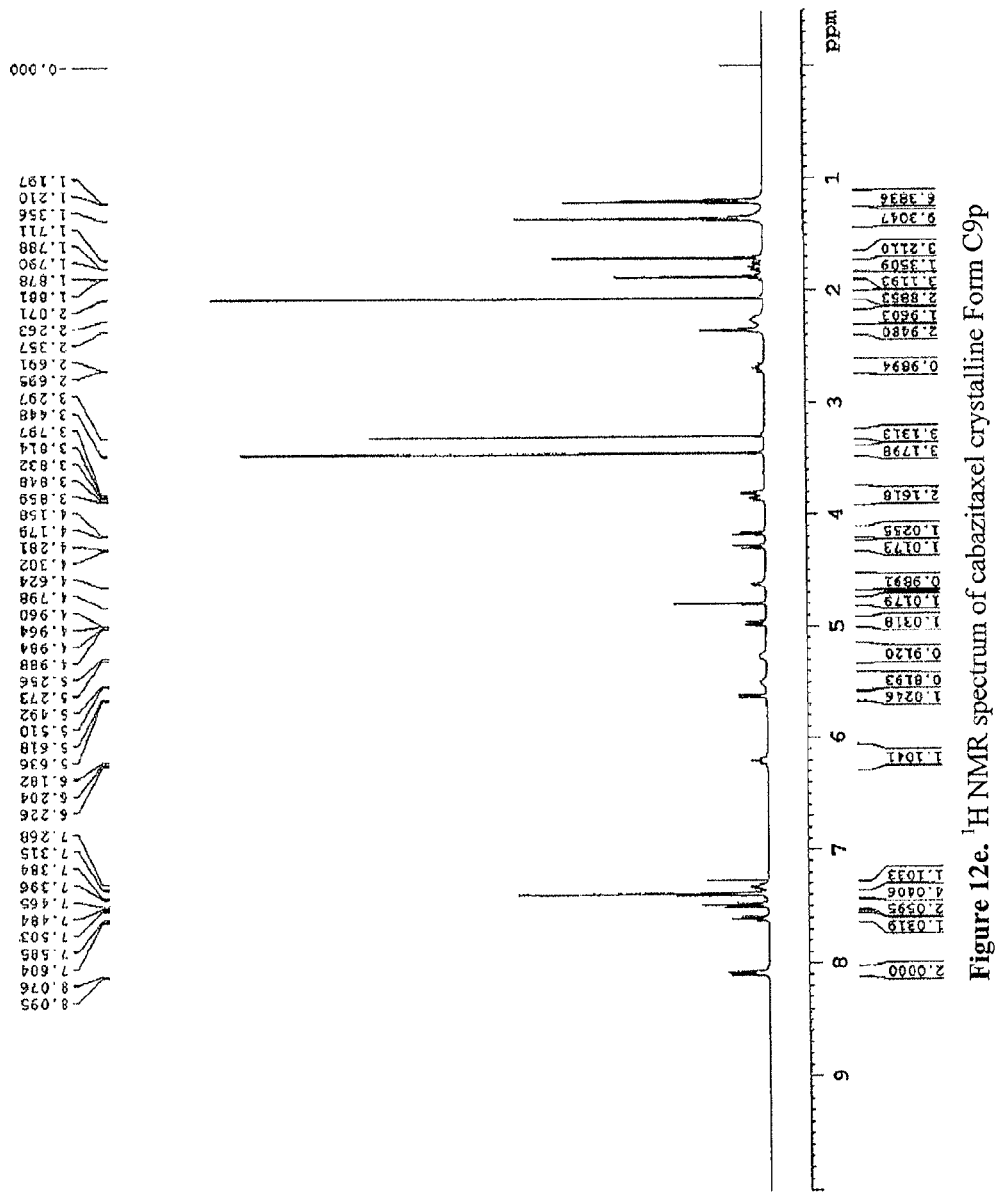
Figure 12e. ¹H NMR spectrum of cabazitaxel crystalline Form C9p

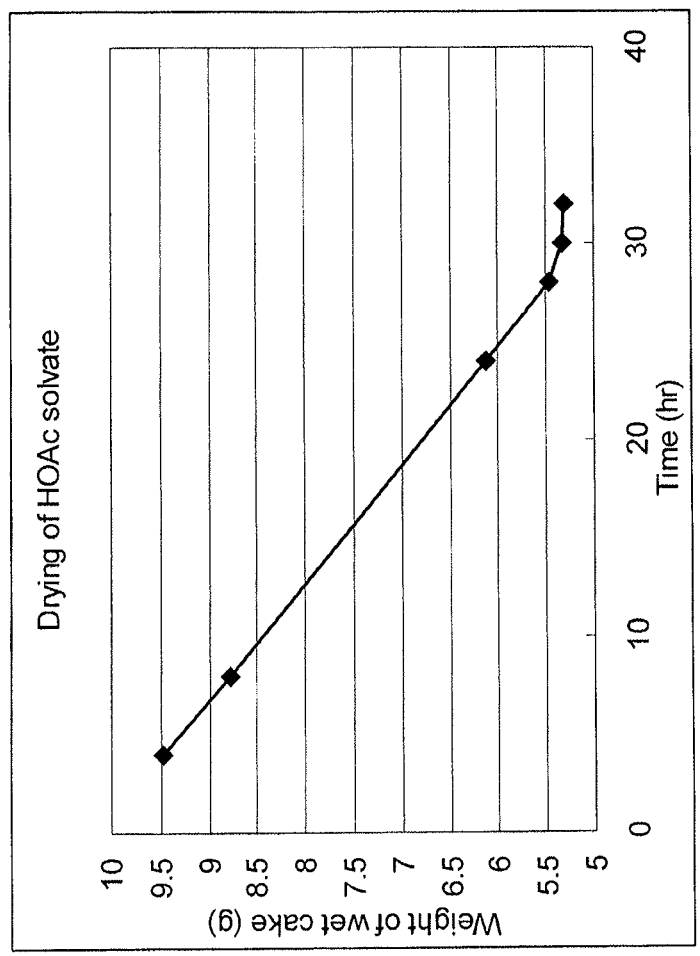
Figure 13. The weight change of cabazitaxel form C9p during drying process

CRYSTALLINE FORMS OF CABAZITAXEL

CROSS-REFERENCES TO RELATED APPLICATIONS

This application is a Divisional Application of U.S. Non-provisional patent application Ser. No. 13/605,908, which was filed Sep. 6, 2012, and claims priority from U.S. Provisional Patent Application Ser. No. 61/533,111, which was filed on Sep. 9, 2011, and U.S. Provisional Patent Application Ser. No. 61/606,288, which was filed on Mar. 2, 2012. The entire content of these applications is incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Jevtana® is an injectable antineoplastic medicine whose active pharmaceutical ingredient (API), cabazitaxel, belongs to the taxane class, and is closely related in both chemical structure and mode of action to the anticancer drugs paclitaxel and docetaxel. Cabazitaxel is prepared by semi-synthesis from 10-deacetylbaccatin III (10-DAB) that is extracted from yew tree needles. The chemical name of cabazitaxel is (2α,5β,7β,10β,13α)-4-acetoxy-13-({(2R,3S)-3-[(tert-butoxycarbonyl)amino]-2-hydroxy-3-phenylpropanoyl}oxy)-1-hydroxy-7,10-dimethoxy-9-oxo-5,20-epoxy-tax-11-en-2-yl benzoate, and the compound is marketed as a 1:1 acetone solvate (Compound A, below).

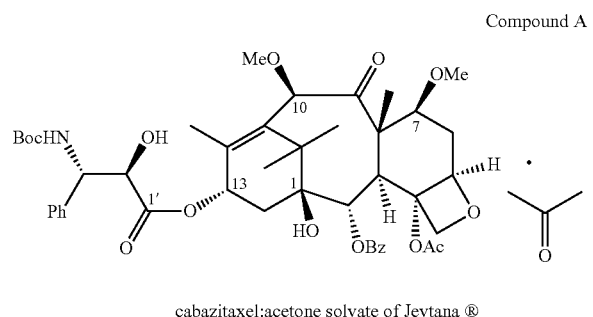

cabazitaxel:acetone solvate of Jevtana ®

The acetone solvate of cabazitaxel is a white to off-white powder with a molecular formula of $C_{45}H_{57}NO_{14} \cdot C_3H_6O$ and a molecular weight of 894.01 grams per mole. The molecular weight of the solvent free form is 835.93 grams per mole.

Cabazitaxel is a dimethyl derivative (also called dimethoxy docetaxel) of docetaxel, which itself is semi-synthetic, and was originally developed by Rhone-Poulenc Rorer and was approved by the U.S. Food and Drug Administration (FDA) for the treatment of hormone-refractory prostate cancer. Cabazitaxel is a microtubule inhibitor.

The acetone solvate crystalline form of cabazitaxel and a process for its preparation is disclosed in U.S. Pat. No. 7,241,907; the XRPD (X-ray powder diffraction) pattern for this solvate type is shown in FIG. 1a.

Other crystalline Rums of cabazitaxel, including anhydrous forms, hydrates, ethanolates, and ethanol/water heterosolvates, are claimed in WO 2009/115655. Certain non-ethanolic solvates have been suggested in WO 2009/115655 and U.S. 2011/0144362, but have not been chemically characterized.

BRIEF SUMMARY OF THE INVENTION

In one aspect, the present invention provides a crystalline form of cabazitaxel selected from the group consisting of Form C1, C2, C3, C4, C5, C6, C7, C8, C9, C8b and C9p. The novel forms have been chemically characterized by $^1$H NMR (nuclear magnetic resonance) spectroscopy, XRPD, FTIR (Fourier transform infrared) spectroscopy (also abbreviated to IR spectroscopy), TGA (thermogravimetric analysis) and DSC (differential scanning calorimetry).

In a second aspect, the present invention provides preparations comprising one or more novel crystalline forms of cabazitaxel and one or more pharmaceutically acceptable excipients.

In a third aspect, the present invention provides processes for the preparation of the crystalline Form C9p of cabazitaxel. In some embodiments, the inventive process includes:
a) slowly cooling a solution comprising cabazitaxel, acetic acid, and $H_2O$ to form a mixture comprising a solid material;
b) filtering the mixture resulting from step a) and washing the isolated solid; and
c) drying the isolated and washed solid resulting from step b) under vacuum with a nitrogen gas purge.

In some embodiments, the inventive process for the preparation of the crystalline Form C9p of cabazitaxel includes:
a) subjecting cabazitaxel to acetic acid vapour; and
b) purging the resulting AcOH solvate with a stream of nitrogen gas.

BRIEF DESCRIPTION OF THE DRAWINGS

FIG. 1 shows the XRPD pattern for a previously known 1:1 cabazitaxel:acetone solvate.
FIG. 2a shows the XRPD pattern of cabazitaxel Form C1.
FIG. 2b shows the IR spectrum of cabazitaxel Form C1.
FIG. 2c shows the DSC trace of cabazitaxel Form C1.
FIG. 2d shows the TGA trace of cabazitaxel Form C1.
FIG. 2e shows the $^1$H NMR spectrum of cabazitaxel Form C1.
FIGS. 3a to 10a show XRPD patterns of cabazitaxel Forms C2 to C9.
FIGS. 3b to 10b show IR spectra of cabazitaxel Forms C2 to C9.
FIGS. 3c to 10c show DSC/TGA traces of cabazitaxel Forms C2 to C9.
FIGS. 3d to 10d show $^1$H NMR spectra of cabazitaxel Forms C2 to C9.
FIGS. 11a and 12a show XRPD patterns of cabazitaxel Forms C8b and C9p.
FIGS. 11b and 12b show IR spectra of cabazitaxel Forms C8b and C9p.
FIGS. 11c and 12c show DSC traces of cabazitaxel Forms C8b and C9p.
FIGS. 11d and 12d show TGA traces of cabazitaxel Forms C8b and C9p.

FIGS. 11e and 12e show $^1$H NMR spectra of cabazitaxel Forms C8b and C9p.

FIG. 13 shows the weight change of cabazitaxel Form C9p during drying.

DETAILED DESCRIPTION OF THE INVENTION

The present invention provides novel crystalline forms of cabazitaxel. The crystalline forms can be produced by the methods described herein and are substantially free of other crystalline forms. The term "substantially free" refers to an amount of 10% or less of another form, preferably 8%, 5%, 4%, 3%, 2%, 1%, 0.5%, or less of another form.

In one aspect, the present invention provides a crystalline form of (2α,5β,7β,10β,13α)-4-acetoxy-13-({(2R,3S)-3-[(tert-butoxycarbonyl)amino]-2-hydroxy-3-phenylpropanoyl}oxy)-1-hydroxy-7,10-dimethoxy-9-oxo-5,20-epoxy-tax-11-en-2-yl benzoate.

The crystalline compound of the present invention can be characterized by a number of techniques including X-ray powder diffraction (XRPD), infrared spectroscopy (IR), differential scanning calorimetry (DSC), thermal gravimetric analysis (TGA), and crystallography.

In some embodiments, the present invention provides the crystalline form of the compound characterized by an XRPD pattern substantially in accordance with that of FIG. 2a, 3a, 4a, 5a, 6a, 7a, 8a, 9a, 10a, 11a, or 12a.

In other embodiments, the crystalline form of the compound is Form C1, characterized by an XRPD pattern that includes one or more peaks at 7.83, 8.91, 9.33, 10.21, 12.55, 12.85, 13.32, 13.56, 14.37, 14.7, 15.17, 15.6, 15.98, 16.54, 17.0, 17.25, 17.69, 18.28, 18.72, 19.42, 19.74, 20.0, 20.46, 21.06, 21.37, 21.74, 21.94, 22.17, 23.09, 23.49, 23.71, 23.97, 24.27, 24.78, 25.12, 25.82, 26.27, 26.91, 27.49, 27.74, 28.32, and 28.78 degrees 2θ (±0.1 degrees 2θ (also referred to as 2-Theta)), wherein said XRPD pattern is made using CuK$_{α1}$ radiation. In another embodiment, the crystalline form of the compound is characterized by an XRPD pattern that includes two or more, three or more, four or more, or five or more peaks at 7.83, 8.91, 9.33, 10.21, 12.55, 12.85, 13.32, 13.56, 14.37, 14.7, 15.17, 15.6, 15.98, 16.54, 17.0, 17.25, 17.69, 18.28, 18.72, 19.42, 19.74, 20.0, 20.46, 21.06, 21.37, 21.74, 21.94, 22.17, 23.09, 23.49, 23.71, 23.97, 24.27, 24.78, 25.12, 25.82, 26.27, 26.91, 27.49, 27.74, 28.32, and 28.78 degrees 2θ (±0.1 degrees 2θ). In some other embodiments, the crystalline form of the compound is characterized by an XRPD pattern that includes peaks (in degrees 2θ (±0.1 degrees 2θ)) as provided in FIG. 2a with intensities greater than 50 cps (counts per second). In other embodiments, the crystalline form of the compound is characterized by an XRPD pattern substantially in accordance with FIG. 2a.

Crystalline Form C1 is an anhydrous isopropanol solvate of cabazitaxel, as evidenced by Karl Fischer (KF) titration data and $^1$H NMR spectroscopy. The IPA content of Form 1 was calculated by integrating a representative peak (—CH, δ 4.01 ppm) in the $^1$H NMR spectrum, indicating a cabazitaxel: IPA molar ratio of 1:0.9 (FIG. 2e). Form C1 contains approximately 0.1% water by weight as determined by KF titration. The thermal analysis of Form C1 was conducted by TGA and DSC. The DSC endotherm for Form C1 exhibits a broad endothermic transition with a maximum temperature at about 176° C. (FIG. 2c). This transition is attributed to desolvation and melting of the sample at temperatures over a range from about 158° C. to about 178.5° C. TGA and hot stage microscopy (HSM) reflect the thermal behavior observed by DSC analysis. TGA, for example, shows a 6.7% weight loss at 125° C.-200° C., followed by a sharp weight loss upon decomposition at about 220° C. (FIG. 2d).

In other embodiments, the crystalline form of the compound is Form C2, characterized by an XRPD pattern that includes one or more peaks at 7.89, 8.59, 10.1, 12.6, 12.84, 13.29, 13.77, 14.03, 14.93, 15.81, 16.67, 16.99, 17.37, 17.97, 18.85, 19.42, 20.08, 20.38, 20.8, 21.49, 21.96, 22.45, 22.76, 23.13, 23.93, 24.45, 24.84, 25.33, 26.01, 26.67, 27.09, 27.72, 28.2, 28.53, 29.33, 30.33, 30.81, 31.66, 32.08, 32.7, 33.27 and 34.03 degrees 2θ (±0.1 degrees 2θ), wherein said XRPD pattern is made using CuK$_{α1}$ radiation. In some embodiments, the crystalline form of the compound is characterized by an XRPD pattern that includes two or more, three or more, four or more, or five or more peaks at 7.89, 8.59, 10.1, 12.6, 12.84, 13.29, 13.77, 14.03, 14.93, 15.81, 16.67, 16.99, 17.37, 17.97, 18.85, 19.42, 20.08, 20.38, 20.8, 21.49, 21.96, 22.45, 22.76, 23.13, 23.93, 24.45, 24.84, 25.33, 26.01, 26.67, 27.09, 27.72, 28.2, 28.53, 29.33, 30.33, 30.81, 31.66, 32.08, 32.7, 33.27 and 34.03 degrees 2θ (+0.1 degrees 2θ). In some embodiments, the crystalline form of the compound is characterized by an XRPD pattern that includes peaks (in degrees 2θ (±0.1 degrees 2θ)) as provided in FIG. 3a with intensities greater than 40 cps. In other embodiments, the crystalline form of the compound is characterized by an XRPD pattern substantially in accordance with FIG. 3a.

Crystalline Form C2 is also characterized by an IR spectrum substantially in accordance with FIG. 3b, DSC/TGA traces substantially in accordance with FIG. 3c, or a $^1$H NMR spectrum substantially in accordance with FIG. 3d.

In other embodiments, the crystalline form of the compound is Form C3, characterized by an XRPD pattern that includes one or more peaks at 7.8, 8.86, 10.16, 11.1, 12.62, 13.43, 14.41, 14.96, 15.28, 15.74, 16.45, 16.99, 17.66, 18.1, 18.52, 19.0, 19.68, 20.4, 21.07, 21.64, 21.9, 22.32, 22.84, 23.49, 23.98, 24.5, 25.07, 25.41, 25.69, 26.2, 26.69, 27.08, 27.53, 28.14, 29.49, 30.4, 30.86, 31.38, 31.96, 33.97, 34.34 and 35.32 degrees 2θ (±0.1 degrees 2θ), wherein said XRPD pattern is made using CuK$_{α1}$ radiation. In some embodiments, crystalline Form C3 is characterized by an XRPD pattern that includes two or more, three or more, four or more, or five or more peaks at 7.8, 8.86, 10.16, 11.1, 12.62, 13.43, 14.41, 14.96, 15.28, 15.74, 16.45, 16.99, 17.66, 18.1, 18.52, 19.0, 19.68, 20.4, 21.07, 21.64, 21.9, 22.32, 22.84, 23.49, 23.98, 24.5, 25.07, 25.41, 25.69, 26.2, 26.69, 27.08, 27.53, 28.14, 29.49, 30.4, 30.86, 31.38, 31.96, 33.97, 34.34 and 35.32 degrees 2θ (±0.1 degrees 2θ). In some embodiments, the crystalline Form C3 is characterized by an XRPD pattern that includes peaks (in degrees 2θ (±0.1 degrees 2θ)) as provided in FIG. 4a with intensities greater than 30 cps. In some embodiments, the crystalline Form C3 is characterized by an XRPD pattern substantially in accordance with FIG. 4a.

Crystalline Form C3 of the present invention is also characterized by an IR spectrum substantially in accordance with FIG. 4b, DSC/TGA traces substantially in accordance with FIG. 4c, or a $^1$H NMR spectrum substantially in accordance with FIG. 4d.

In other embodiments, the crystalline form of the compound is Form C4, characterized by an XRPD diffraction pattern that includes one or more peaks at 8.5, 9.02, 9.94, 12.53, 13.12, 14.03, 14.93, 15.87, 16.81, 17.29, 17.79, 18.74, 19.62, 20.21, 20.65, 21.55, 22.03, 22.5, 23.3, 23.85, 24.36, 25.23, 25.91, 26.44, 26.86, 27.4, 27.82, 28.29, 28.87, 30.09, 31.0, 32.37, 33.06, 34.24, 34.99, 36.21, 36.52, 37.26, 37.92, 38.35 and 39.2 degrees 2θ (±0.1 degrees 2θ), wherein said XRPD pattern is made using CuK$_{α1}$ radiation. In some embodiments, the crystalline Form C4 is characterized by an XRPD pattern that includes two or more, three or more, four or more, or five or more peaks at 8.5, 9.02, 9.94, 12.53, 13.12, 14.03, 14.93, 15.87, 16.81, 17.29, 17.79, 18.74, 19.62, 20.21, 20.65, 21.55, 22.03, 22.5, 23.3, 23.85, 24.36, 25.23, 25.91, 26.44, 26.86, 27.4, 27.82, 28.29, 28.87, 30.09, 31.0, 32.37, 33.06, 34.24, 34.99, 36.21, 36.52, 37.26, 37.92, 38.35 and 39.2 degrees 2θ (±0.1 degrees 2θ). In some embodiments, the Form C4 is characterized by an XRPD pattern that includes peaks (in degrees 2θ (±0.1 degrees 2θ)) as provided in FIG. 5a with intensities greater than 30 cps. In some embodiments, the crystalline Form C4 is characterized by an XRPD pattern substantially in accordance with FIG. 5a.

Crystalline Form C4 of the present invention is also characterized by an IR spectrum substantially in accordance with FIG. 5b, DSC/TGA traces substantially in accordance with FIG. 5c, or a $^1$H NMR spectrum substantially in accordance with FIG. 5d.

In other embodiments, the crystalline form of the compound is Form C5, characterized by an XRPD pattern that includes one or more peaks at 7.83, 8.78, 10.12, 11.11, 12.59, 12.83, 13.48, 14.29, 14.94, 15.19, 15.74, 16.53, 16.99, 17.58, 18.1, 18.39, 18.75, 19.1, 19.78, 20.36, 20.98, 21.7, 22.12, 22.46, 22.88, 23.26, 23.73, 23.99, 24.25, 24.92, 25.33, 25.85, 26.18, 26.7, 27.14, 27.73, 28.3, 28.59, 28.86, 29.49, 30.5 and 30.79 degrees 2θ (±0.1 degrees 2θ), wherein said XRPD pattern is made using CuK$_{\alpha 1}$ radiation. In some embodiments, the crystalline Form C5 is characterized by an XRPD pattern that includes two or more, three or more, four or more, or five or more peaks at 7.83, 8.78, 10.12, 11.11, 12.59, 12.83, 13.48, 14.29, 14.94, 15.19, 15.74, 16.53, 16.99, 17.58, 18.1, 18.39, 18.75, 19.1, 19.78, 20.36, 20.98, 21.7, 22.12, 22.46, 22.88, 23.26, 23.73, 23.99, 24.25, 24.92, 25.33, 25.85, 26.18, 26.7, 27.14, 27.73, 28.3, 28.59, 28.86, 29.49, 30.5 and 30.79 degrees 2θ (±0.1 degrees 2θ). In some embodiments, the Form C5 is characterized by an XRPD pattern that includes peaks (in degrees 2θ (±0.1 degrees 2θ)) as provided in FIG. 6a with intensities greater than 40 cps. In other embodiments, crystalline Form C5 is characterized by an XRPD pattern substantially in accordance with FIG. 6a.

Crystalline Form C5 of the present invention is also characterized by an IR spectrum substantially in accordance with FIG. 6b, DSC/TGA traces substantially in accordance with FIG. 6c, or a $^1$H NMR spectrum substantially in accordance with FIG. 6d.

In other embodiments, the crystalline form of the compound is Form C6, characterized by an XRPD pattern that includes one or more peaks at 7.77, 8.81, 10.13, 12.55, 12.78, 13.37, 14.26, 14.78, 15.14, 15.6, 16.43, 16.97, 17.57, 18.09, 18.42, 18.81, 19.52, 20.38, 20.96, 21.46, 21.91, 22.23, 22.82, 23.42, 23, 94, 24.91, 25.31, 25.68, 25.95, 26.45, 26.69, 27.04, 27.42, 27.97, 28.19, 28.59, 29.36, 30.27, 30.82, 31.33, 31.68 and 32.75 degrees 2θ (±0.1 degrees 2θ), wherein said XRPD pattern is made using CuK$_{\alpha 1}$ radiation. In some embodiments, crystalline Form C6 is characterized by an XRPD pattern that includes two or more, three or more, four or more, or five or more peaks at 7.77, 8.81, 10.13, 12.55, 12.78, 13.37, 14.26, 14.78, 15.14, 15.6, 16.43, 16.97, 17.57, 18.09, 18.42, 18.81, 19.52, 20.38, 20.96, 21.46, 21.91, 22.23, 22.82, 23.42, 23.94, 24.91, 25.31, 25.68, 25.95, 26.45, 26.69, 27.04, 27.42, 27.97, 28.19, 28.59, 29.36, 30.27, 30.82, 31.33, 31.68 and 32.75 degrees 2θ (±0.1 degrees 2θ). In some embodiments, Form C6 is characterized by an XRPD pattern that includes peaks (in degrees 2θ (±0.1 degrees 2θ)) as provided in FIG. 7a with intensities greater than 40 cps. In other embodiments, the crystalline Form C6 is characterized by an XRPD pattern substantially in accordance with FIG. 7a.

Crystalline Form C6 of the present invention is also characterized by an IR spectrum substantially in accordance with FIG. 7b, DSC/TGA traces substantially in accordance with FIG. 7c, or a $^1$H NMR spectrum substantially in accordance with FIG. 7d.

In other embodiments, the crystalline form of the compound is Form C7, characterized by an XRPD pattern that includes one or more peaks at 7.75, 8.57, 10.08, 11.03, 12.51, 12.8, 13.39, 14.01, 14.78, 15.58, 16.4, 16.93, 17.37, 17.9, 18.62, 19.0, 19.67, 20.31, 20.75, 21.55, 22.04, 22.64, 23.51, 23.97, 24.4, 25.19, 25.78, 26.05, 26.61, 26.98, 27.61, 28.09, 28.47, 29.26, 29.58, 30.25, 30.76, 31.4, 32.01, 32.36, 33.27 and 33.64 degrees 2θ (±0.1 degrees 2θ), wherein said XRPD pattern is made using CuK$_{\alpha 1}$ radiation. In another embodiments, crystalline Form C7 is characterized by an XRPD pattern that includes two or more, three or more, four or more, or five or more peaks at 7.75, 8.57, 10.08, 11.03, 12.51, 12.8, 13.39, 14.01, 14.78, 15.58, 16.4, 16.93, 17.37, 17.9, 18.62, 19.0, 19.67, 20.31, 20.75, 21.55, 22.04, 22.64, 23.51, 23.97, 24.4, 25.19, 25.78, 26.05, 26.61, 26.98, 27.61, 28.09, 28.47, 29.26, 29.58, 30.25, 30.76, 31.4, 32.01, 32.36, 33.27 and 33.64 degrees 2θ (±0.1 degrees 2θ). In some embodiments, crystalline Form C7 is characterized by an XRPD pattern that includes peaks (in degrees 2θ (±0.1 degrees 2θ)) as provided in FIG. 8a with intensities greater than 40 cps. In other embodiments, crystalline Form C67 is characterized by the XRPD peaks substantially in accordance with FIG. 8a.

Crystalline Form C7 of the present invention is also characterized by an IR spectrum substantially in accordance with FIG. 8b, DSC/TGA traces substantially in accordance with FIG. 8c, or a $^1$H NMR spectrum substantially in accordance with FIG. 8d.

In other embodiments, the crystalline form of the compound is Form C8, characterized by an XRPD pattern that includes one or more peaks at 7.92, 8.84, 9.4, 10.09, 12.54, 12.84, 13.47, 14.29, 14.9, 15.13, 15.75, 15.91, 16.16, 16.72, 16.91, 17.13, 17.56, 18.02, 18.2, 18.44, 18.93, 19.15, 19.8, 20.28, 20.9, 21.12, 21.68, 22.24, 22.46, 23.12, 23.41, 23.95, 24.52, 24.9, 25.27, 25.69, 26.09, 26.31, 26.76, 27.34, 28.0 and 28.32 degrees 2θ (±0.1 degrees 2θ), wherein said XRPD pattern is made using CuK$_{\alpha 1}$ radiation. In some embodiments, crystalline Form C8 is characterized by an XRPD pattern that includes two or more, three or more, four or more, or five or more peaks at 7.92, 8.84, 9.4, 10.09, 12.54, 12.84, 13.47, 14, 29, 14.9, 15.13, 15.75, 15.91, 16.16, 16.72, 16.91, 17.13, 17.56, 18.02, 18.2, 18.44, 18.93, 19.15, 19.8, 20.28, 20.9, 21.12, 21.68, 22.24, 22.46, 23.12, 23.41, 23.95, 24.52, 24.9, 25.27, 25.69, 26.09, 26.31, 26.76, 27.34, 28.0 and 28.32 degrees 2θ (±0.1 degrees 2θ). In some embodiments, crystalline Form C8 is characterized by an XRPD pattern that includes peaks (in degrees 2θ (±0.1 degrees 2θ)) as provided in FIG. 9a with intensities greater than 40 cps. In some embodiments, the crystalline Form C8 is characterized by an XRPD pattern substantially in accordance with FIG. 9a.

Crystalline Form C8 of the present invention is also characterized by an IR spectrum substantially in accordance with FIG. 9b, DSC/TGA traces substantially in accordance with FIG. 9c, or a NMR spectrum substantially in accordance with FIG. 9d.

In other embodiments, crystalline Form C8b is formed by recrystallization from an aqueous DMSO solution. The XRPD pattern of Form C8b is shown in FIG. 11a which is distinct from the XRPD pattern of Form C8. In some embodiments, the crystalline form of cabazitaxel is Form C8b, characterized by an XRPD pattern that includes one or more peaks at 7.19, 7.63, 8.16, 9.22, 10.14, 10.73, 11.66, 12.12, 12.78, 13.58, 14.00, 14.59, 15.14, 15.86, 16.40, 17.22, 17.54, 18.14, 18.94, 19.95, 20.45, 21.00, 21.24, 21.65, 22.13, 22.45, 23.17, 23.56, 23.90, 24.55, 25.25, 25.74, 26.74, 27.61, 28.49, 29.09, 29.74, 30.3, 31.00, 32.11, 32.63 and 33.14 degrees 2θ (±0.1 degrees 2θ), wherein said XRPD pattern is made using CuK$_{\alpha 1}$ radiation. In some embodiments, crystalline Form C8b is characterized by an XRPD pattern that includes two or more, three or more, four or more, or five or more peaks at 7.19, 7.63, 8.16, 9.22, 10.14, 10, 73, 11.66, 12.12, 12.78, 13.58, 14.00, 14.59, 15.14, 15.86, 16.40, 17.22, 17.54, 18.14, 18.94, 19.95, 20.45, 21.00, 21.24, 21.65, 22.13, 22.45, 23.17, 23.56, 23.90, 24.55, 25.25, 25.74, 26.74, 27.61, 28.49, 29.09, 29.74, 30.3, 31.00, 32.11, 32.63 and 33.14 degrees 2θ (+0.1 degrees 2θ). In some embodiments, Form C8b is characterized by an XRPD pattern that includes peaks (in degrees 2θ (±0.1 degrees 2θ)) as provided in FIG. 11a with intensities greater than 30 cps. In some embodiments, crystalline Form C8b is characterized by an XRPD pattern substantially in accordance with FIG. 11a.

The differences between the XRPD patterns for Forms C8 and C8b indicate that the two crystalline forms are different, which is confirmed by the differences in the DSC and TGA data for the two forms. The DSC trace for Form C8b exhibits an endothermic transition with a maximum temperature at 66° C., corresponding to dehydration and desolvation, and an endothermic transition with a maximum temperature at 140° C., corresponding to sample melting (FIG. 11c). TGA and hot stage microscopy of crystalline Form C8b confirm the thermal behavior observed by DSC. The TGA trace, for example, shows a 7.4% weight loss at 30° C.-160° C. followed by a sharp weight loss upon decomposition at about 220° C. (FIG. 11d).

Form C8b is a monohydrate DMSO solvate, as shown by $^1$H NMR spectroscopy and KF titration. The DMSO content of Form C8b is calculated by integrating a representative DMSO peak (—S—CH$_3$, δ 2.61 ppm) in the $^1$H NMR spectrum, indicating a cabazitaxel:DMSO molar ratio of 1:0.7-0.9 (FIG. 11e).

In other embodiments, the crystalline form of cabazitaxel is Form C9, characterized by an XRPD pattern that includes one or more peaks at 8.2, 8.76, 9.33, 10.25, 10.99, 11.73, 12.24, 12.92, 14.04, 14.72, 15.33, 15.92, 16.46, 17.69, 18.42, 19.31, 19.79, 20.5, 21.42, 22.18, 22.54, 23.34, 23.69, 24.02, 24.73, 25.47, 25.78, 26.69, 27.44, 27.98, 28.62, 29.38, 29.76, 30.16, 30.44, 31.29, 32.02, 32.73, 33.78, 34.37, 34.98 and 36.01 degrees 2θ (±0.1 degrees 2θ), wherein said XRPD pattern is made using CuK$_{\alpha 1}$ radiation. In some embodiments, crystalline Form C9 is characterized by an XRPD pattern that includes two or more, three or more, four or more, or five or more peaks at 8.2, 8.76, 9.33, 10.25, 10.99, 11.73, 12.24, 12.92, 14.04, 14.72, 15.33, 15.92, 16.46, 17.69, 18.42, 19.31, 19.79, 20.5, 21.42, 22.18, 22.54, 23.34, 23.69, 24.02, 24.73, 25.47, 25.78, 26.69, 27.44, 27.98, 28.62, 29.38, 29.76, 30.16, 30.44, 31.29, 32.02, 32.73, 33.78, 34.37, 34.98 and 36.01 degrees 2θ (+0.1 degrees 2θ). In some embodiments, Form C9 is characterized by an XRPD pattern that includes peaks (in degrees 2θ (±0.1 degrees 2θ)) as provided in FIG. 10a with intensities greater than 30 cps. In some embodiments, crystalline Form C9 is characterized by an XRPD pattern substantially in accordance with FIG. 10a.

Crystalline Form C9 of the present invention is also characterized by an infrared spectrum substantially in accordance with FIG. 10b, DSC/TGA traces substantially in accordance with FIG. 10c, or a $^1$H NMR spectrum substantially in accordance with FIG. 10d.

XRPD analysis confirmed that Form C9 is crystalline. Form C9 shows a 5% weight loss at 170° C. by TGA analysis, while an endothermic transition at 157° C. in the DSC trace corresponds to a melting point between 153 and 159° C. (FIG. 10c). Decomposition occurs at about 220° C., as indicated by the large weight loss observed by TGA around this temperature. Dynamic vapor sorption (DVS) analysis shows a non-perfectly reversible weight loss and gain upon changing humidity (over 2 cycles tested), consistent with loss of AcOH upon dehumidification. This was confirmed by $^1$H NMR spectroscopy after DVS analysis. KF titration of Form C9 indicated the presence of about 2.3% water.

In other embodiments, the crystalline form of the compound is Form C9p. The inventors discovered that Form C9 is, in fact, a mixture of a crystalline form and a novel acetic acid solvate. Form C9p, the acetic acid solvate, has now been prepared in pure form, substantially free of Form C9. The XRPD pattern of Form C9p is shown in FIG. 12a. The XRPD pattern of Form C9p is clearly different from that of Form C9.

In some embodiments, the crystalline Form C9p is characterized by an XRPD pattern that includes one or more peaks at 7.24, 8.16, 8.69, 9.25, 10.21, 10.74, 11.73, 12.22, 12.87, 13.66, 14.12, 14.70, 15.25, 15.88, 16.34, 17.40, 17.72, 18.29, 19.10, 19.69, 20.07, 20.47, 21.04, 21.42, 21.71, 22.16, 22.53, 22.86, 23.40, 23.69, 23.91, 24.71, 25.37, 25.75, 26.68, 27.01, 27.57, 28.31, 28.67, 28.85, 29.32, 29.71, 30.43, 31.27, 32.19, 32.72, 33.42, 33.73, 34.25, 35.06, 36.02, 36.52, 37.48, 38.04, 38.77 and 39.48 degrees 2θ (±0.1 degrees 2θ), wherein said XRPD pattern is made using CuK$_{\alpha 1}$ radiation. In some embodiments, the crystalline Form C9p is characterized by an XRPD pattern that includes two or more, three or more, four or more, or five or more peaks at 7.24, 8.16, 8.69, 9.25, 10.21, 10.74, 11.73, 12.22, 12.87, 13.66, 14.12, 14.70, 15.25, 15.88, 16.34, 17.40, 17.72, 18.29, 19.10, 19.69, 20.07, 20.47, 21.04, 21.42, 21.71, 22.16, 22.53, 22.86, 23.40, 23.69, 23.91, 24.71, 25.37, 25.75, 26.68, 27.01, 27.57, 28.31, 28.67, 28.85, 29.32, 29.71, 30.43, 31.27, 32.19, 32.72, 33.42, 33.73, 34.25, 35.06, 36.02, 36.52, 37.48, 38.04, 38.77 and 39.48 degrees 2θ (±0.1 degrees 2θ). In some embodiments, Form C9p is characterized by an XRPD pattern that includes peaks (in degrees 2θ (±0.1 degrees 2θ)) as provided in FIG. 12a with intensities greater than 30 cps. In some embodiments, crystalline Form. C9p is characterized by an XRPD pattern substantially in accordance with FIG. 12a.

The crystalline Form C9p of the present invention is also characterized by an IR spectrum substantially in accordance with FIG. 12b, DSC and TGA traces substantially in accordance with FIG. 12c and FIG. 12d, respectively, or a $^1$H NMR spectrum substantially in accordance with FIG. 12e.

The crystalline compound of Form C9p is a monohydrate acetic acid solvate, as shown by $^1$H NMR spectroscopy and KF titration. The acetic acid content was calculated by integrating a representative peak (—CH$_3$, δ 2.11 ppm) in the $^1$H NMR spectrum (FIG. 12e), indicating a cabazitaxel:AcOH molar ratio of about 1:1-0.9. The water content of Form C9p, as determined by KF titration, is about 2% by weight. The thermal analysis of Form C9p was conducted using TGA and DSC. The DSC trace shows that Form C9p exhibits two endothermic transitions with maximum temperatures at 77° C. and 147° C. (FIG. 12c). Dehydration and desolvation occurs before 150° C. prior to melting at 150° C.-165° C. TGA and HSM reflected the thermal behavior observed in DSC analysis. The TGA trace, for example, shows about 8.0% weight loss at 30° C.-160° C., followed by a sharp weight loss upon decomposition at about 220° C. (FIG. 12d).

In a related aspect, the present invention provides a process for preparing crystalline Form C9p of cabazitaxel including:
    a) slowly cooling a solution comprising cabazitaxel, acetic acid, and H$_2$O to form a mixture comprising a solid material;
    b) filtering the mixture resulting from step a) and washing the isolated solid (also known as a filter cake); and c) drying the isolated and washed solid resulting from step b) under vacuum with a nitrogen gas purge until the weight of the solid becomes constant.

The solution of step a) is cooled to a temperature such that a substantial amount of the crystalline form crystallizes from the solution with acceptable purity. In some embodiments, the solution of step a) may be cooled from any temperature at or above 50° C. to any temperature at or below 40° C. The solution can be cooled, for example, from a temperature at or above 50° C. to a temperature from 0° C. to 40° C., or from 5° C. to 30° C., or from 20° C. to 25° C. In some embodiments, the solution of step a) may be cooled from any temperature at or above 20° C. to any temperature at or below 10° C. The solution can be cooled, for example, from a temperature from 20° C. to 25° C. to a temperature from −80° C. to 10° C., or from 0° C. to 10° C., or from 0° C. to 5° C. In some embodiments, washing in step b) is conducted using water. Drying in step c) is controlled so as to avoid partial or complete desolvation of the solvate, which can occur when the drying time is too long, the temperature is too high, or the pressure is too low. In some embodiments, the drying step is conducted until the molar ratio of cabazitaxel and AcOH is about 1:1. The drying step can be controlled in several ways including: i) by monitoring the weight of the solids being dried and terminating the drying when the weight change becomes small or the weight becomes constant; and/or ii) by monitoring the AcOH level of the solid being dried and terminating the drying when the molar ratio of AcOH to cabazitaxel is about 1 to 1. The level of AcOH in the solids being dried can be determined using analytical techniques known to one skilled in the art, including gas chromatography (GC) and $^1$H NMR spectroscopy. FIG. 13 shows the weight change of cabazitaxel Form C9p during the drying of the solvate crystallised from aqueous AcOH as described in Example 13 below. In some embodiments, the drying in step c) is conducted at 60-200 torr. In some embodiments, the drying in step c) is conducted at 60-200 torr and 20-25° C. In some embodiments, the drying in step c) is conducted at 60-200 torr at ambient temperature, at about 22° C. The pressure is moderated with a nitrogen gas purge.

In another aspect, the invention provides a process for preparing crystalline Form C9p of cabazitaxel including:
a) contacting solid cabazitaxel with acetic acid vapor under conditions sufficient to form an acetic acid solvate; and
b) purging the resulting acetic acid solvate with a stream of nitrogen gas.

The solid cabazitaxel used in the process can be an anhydrous crystalline form or a solvate (such as an EtOAc solvate, for example). The contacting step a) can be achieved by placing cabazitaxel in a sintered glass Buchner funnel and passing a stream of acetic acid vapor through the narrow end of the Buchner funnel such that it passes through the cabazitaxel. This step can be conducted at ambient temperature. In some embodiments, contacting cabazitaxel with acetic acid vapor involves flowing the vapor in an atmosphere of nitrogen gas. The acetic acid vapor can be produced by passing a stream of nitrogen gas through a reservoir of acetic acid at ambient temperature. The level of acetic acid vapour in the nitrogen stream can be adjusted by changing the temperature of the reservoir of acetic acid and/or changing the flow rate of the nitrogen gas stream. The solid can then be purged with nitrogen gas to remove excess acetic acid that is not associated with the cabazitaxel solvate. The acetic acid content of the solvate can optionally be monitored during the nitrogen purging step to ensure that the molar ratio of cabazitaxel to acetic acid is about 1:1. The level of acetic acid in the solid material being purged with nitrogen can be determined using analytical techniques known to one skilled in the art, including GC and $^1$H NMR spectroscopy. The process yields solvate Form C9p as a monohydrate because it is exposed to the atmosphere during the contacting and purging steps.

Table 1 below outlines the conditions used for preparation of crystalline Forms C1-C9p and Table 2 shows the positions of XPRD peaks for the novel forms.

TABLE 1

Crystalline forms of cabazitaxel

| Form | Recrystallisation solvent | Residual solvent[1] |
|------|---------------------------|---------------------|
| C1 | DCM/IPA or IPA/H$_2$O or IPA slurry | IPA |
| C2 | EtOAc/n-heptane or EtOAc slurry | EtOAc |
| C3 | THF/n-heptane | THF |
| C4 | THF/PhMe or PhMe slurry | PhMe |
| C5 | Methyl ethyl ketone/n-heptane | MEK |
| C6 | Diethyl ketone/n-heptane | DEK |
| C7 | Diethyl carbonate/n-heptane | Diethyl carbonate |
| C8 | DMSO/H$_2$O | DMSO |
| C8b | DMSO/H$_2$O | DMSO |
| C9 | AcOH/H$_2$O | AcOH |
| C9p | AcOH/H$_2$O | AcOH |

[1]Solvent key: DCM = dichloromethane; IPA = isopropanol (2-propanol; propan-2-ol); THF = tetrahydrofuran; PhMe = toluene; MEK = methyl ethyl ketone (EtCOMe); DEK = diethyl ketone (Et$_2$CO); EtOAc = ethyl acetate; DMSO = dimethyl sulfoxide; AcOH = acetic acid

TABLE 2

XRPD pattern data of crystalline forms of cabazitaxel

| Form | Degrees 2θ (+/−0.1 Degrees 2θ) | | | | | | | | | | | | | |
|------|---|---|---|---|---|---|---|---|---|---|---|---|---|---|
| C1 | 7.83 | 8.91 | 9.33 | 10.21 | 12.55 | 12.85 | 13.32 | 13.56 | 14.37 | 14.7 | 15.17 | 15.6 | 15.98 | 16.54 |
| | 17 | 17.25 | 17.69 | 18.28 | 18.72 | 19.42 | 19.74 | 20 | 20.46 | 21.06 | 21.37 | 21.74 | 21.94 | 22.17 |
| | 23.09 | 23.49 | 23.71 | 23.97 | 24.27 | 24.78 | 25.12 | 25.82 | 26.27 | 26.91 | 27.49 | 27.74 | 28.32 | 28.78 |
| C2 | 7.89 | 8.59 | 10.1 | 12.6 | 12.84 | 13.29 | 13.77 | 14.03 | 14.93 | 15.81 | 16.67 | 16.99 | 17.37 | 17.97 |
| | 18.85 | 19.42 | 20.08 | 20.38 | 20.8 | 21.49 | 21.96 | 22.45 | 22.76 | 23.13 | 23.93 | 24.45 | 24.84 | 25.33 |
| | 26.01 | 26.67 | 27.09 | 27.72 | 28.2 | 28.53 | 29.33 | 30.33 | 30.81 | 31.66 | 32.08 | 32.7 | 33.27 | 34.03 |
| C3 | 7.8 | 8.86 | 10.16 | 11.1 | 12.62 | 13.43 | 14.41 | 14.96 | 15.28 | 15.74 | 16.45 | 16.99 | 17.66 | 18.1 |
| | 18.52 | 19 | 19.68 | 20.4 | 21.07 | 21.64 | 21.9 | 22.32 | 22.84 | 23.49 | 23.98 | 24.5 | 25.07 | 25.41 |
| | 25.69 | 26.2 | 26.69 | 27.08 | 27.53 | 28.14 | 29.49 | 30.4 | 30.86 | 31.38 | 31.96 | 33.97 | 34.34 | 35.32 |
| C4 | 8.5 | 9.02 | 9.94 | 12.53 | 13.12 | 14.03 | 14.93 | 15.87 | 16.81 | 17.29 | 17.79 | 18.74 | 19.62 | 20.21 |
| | 20.65 | 21.55 | 22.03 | 22.5 | 23.3 | 23.85 | 24.36 | 25.23 | 25.91 | 26.44 | 26.86 | 27.4 | 27.82 | 28.29 |
| | 28.87 | 30.09 | 31 | 32.37 | 33.06 | 34.24 | 34.99 | 36.21 | 36.52 | 37.26 | 37.92 | 38.35 | 39.2 | |
| C5 | 7.83 | 8.78 | 10.12 | 11.11 | 12.59 | 12.83 | 13.48 | 14.29 | 14.94 | 15.19 | 15.74 | 16.53 | 16.99 | 17.58 |
| | 18.1 | 18.39 | 18.75 | 19.1 | 19.78 | 20.36 | 20.98 | 21.7 | 22.12 | 22.46 | 22.88 | 23.26 | 23.73 | 23.99 |
| | 24.25 | 24.92 | 25.33 | 25.85 | 26.18 | 26.7 | 27.14 | 27.73 | 28.3 | 28.59 | 28.86 | 29.49 | 30.5 | 30.79 |
| C6 | 7.77 | 8.81 | 10.13 | 12.55 | 12.78 | 13.37 | 14.26 | 14.78 | 15.14 | 15.6 | 16.43 | 16.97 | 17.57 | 18.09 |
| | 18.42 | 18.81 | 19.52 | 20.38 | 20.96 | 21.46 | 21.91 | 22.23 | 22.82 | 23.42 | 23.94 | 24.91 | 25.31 | 25.68 |

TABLE 2-continued

XRPD pattern data of crystalline forms of cabazitaxel

| Form | Degrees 2θ (+/−0.1 Degrees 2θ) | | | | | | | | | | | | | |
|---|---|---|---|---|---|---|---|---|---|---|---|---|---|---|
|  | 25.95 | 26.45 | 26.69 | 27.04 | 27.42 | 27.97 | 28.19 | 28.59 | 29.36 | 30.27 | 30.82 | 31.33 | 31.68 | 32.75 |
| C7 | 7.75 | 8.57 | 10.08 | 11.03 | 12.51 | 12.8 | 13.39 | 14.01 | 14.78 | 15.58 | 16.4 | 16.93 | 17.37 | 17.9 |
|  | 18.62 | 19 | 19.67 | 20.31 | 20.75 | 21.55 | 22.04 | 22.64 | 23.51 | 23.97 | 24.4 | 25.19 | 25.78 | 26.05 |
|  | 26.61 | 26.98 | 27.61 | 28.09 | 28.47 | 29.26 | 29.58 | 30.25 | 30.76 | 31.4 | 32.01 | 32.36 | 33.27 | 33.64 |
| C8 | 7.92 | 8.84 | 9.4 | 10.09 | 12.54 | 12.84 | 13.47 | 14.29 | 14.9 | 15.13 | 15.75 | 15.91 | 16.16 | 16.72 |
|  | 16.91 | 17.13 | 17.56 | 18.02 | 18.2 | 18.44 | 18.93 | 19.15 | 19.8 | 20.28 | 20.9 | 21.12 | 21.68 | 22.24 |
|  | 22.46 | 23.12 | 23.41 | 23.95 | 24.52 | 24.9 | 25.27 | 25.69 | 26.09 | 26.31 | 26.76 | 27.34 | 28 | 28.32 |
| C8b | 7.19 | 7.63 | 8.16 | 9.22 | 10.14 | 10.73 | 11.66 | 12.12 | 12.78 | 13.58 | 14.00 | 14.59 | 15.14 | 15.86 |
|  | 16.40 | 17.22 | 17.54 | 18.14 | 18.94 | 19.95 | 20.45 | 21.00 | 21.24 | 21.65 | 22.13 | 22.45 | 23.17 | 23.56 |
|  | 23.90 | 24.55 | 25.25 | 25.74 | 26.74 | 27.61 | 28.49 | 29.09 | 29.74 | 30.30 | 31.00 | 32.11 | 32.63 | 33.14 |
| C9 | 8.2 | 8.76 | 9.33 | 10.25 | 10.99 | 11.73 | 12.24 | 12.92 | 14.04 | 14.72 | 15.33 | 15.92 | 16.46 | 17.69 |
|  | 18.42 | 19.31 | 19.79 | 20.5 | 21.42 | 22.18 | 22.54 | 23.34 | 23.69 | 24.02 | 24.73 | 25.47 | 25.78 | 26.69 |
|  | 27.44 | 27.98 | 28.62 | 29.38 | 29.76 | 30.16 | 30.44 | 31.29 | 32.02 | 32.73 | 33.78 | 34.37 | 34.98 | 36.01 |
| C9p | 7.24 | 8.16 | 8.69 | 9.25 | 10.21 | 10.74 | 11.73 | 12.22 | 12.87 | 13.66 | 14.12 | 14.70 | 15.25 | 15.88 |
|  | 16.34 | 17.40 | 17.72 | 18.29 | 19.10 | 19.69 | 20.07 | 20.47 | 21.04 | 21.42 | 21.71 | 22.16 | 22.53 | 22.86 |
|  | 23.40 | 23.69 | 23.91 | 24.71 | 25.37 | 25.75 | 26.68 | 27.01 | 27.57 | 28.31 | 28.67 | 28.85 | 29.32 | 29.71 |
|  | 30.43 | 31.27 | 32.19 | 32.72 | 33.42 | 33.73 | 34.25 | 35.06 | 36.02 | 36.52 | 37.48 | 38.04 | 38.77 | 39.48 |

In another aspect, the present invention provides pharmaceutical compositions including one or more of the novel crystalline forms of cabazitaxel as well as one or more pharmaceutically acceptable excipients. Pharmaceutically acceptable excipients aid the administration of the solid forms to a subject and can promote absorption of the active agent by a subject. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention.

EXAMPLES

The following examples are provided to further illustrate, but not to limit this invention.

Example 1

Preparation of Cabazitaxel Crystalline Form C1

Cabazitaxel (0.1 g) was dissolved in 0.6 mL of IPA, and an additional 0.4 mL of water were added with heating. The solution was cooled slowly to room temperature. The mixture was filtered and the collected solids were dried in vacuo at 20 to 30° C. for 3-4 days to give cabazitaxel Form C1 as a white solid (melting point: 153.8-161.9° C.).

Example 2

Preparation of Cabazitaxel Crystalline Form C2

A slurry of cabazitaxel (0.1 g) and 1 mL of EtOAc was heated at 70 to 80° C. for about 2 hours. The mixture was cooled to room temperature and stirred for 2 days. The mixture was filtered and the collected solids were dried in a vacuum oven to give cabazitaxel Form C2 (melting point: 156.5-160.0° C.).

Example 3

Preparation of Cabazitaxel Crystalline Form C2

Cabazitaxel Form C2 was also prepared by recrystallisation from EtOAc and n-heptane at room temperature. A solution of cabazitaxel (0.1 g), in EtOAc (3 mL) was prepared with heating. n-Heptane (6 mL) was added to precipitate the product. The mixture was filtered and the resulting solids were dried under vacuum oven to give a white solid of cabazitaxel Form C2.

Example 4

Preparation of Cabazitaxel Crystalline Form C3

A hot solution of cabazitaxel (0.1 g) in 0.4 mL of THF and 0.6 mL of n-heptane was slowly cooled to room temperature. The mixture was filtered and the resulting solids were dried in a vacuum oven to give cabazitaxel Form C3 as a white solid (melting point: 158.9-165.4° C.).

Example 5

Preparation of Cabazitaxel Crystalline Form C4

A slurry of cabazitaxel (0.1 g) and 1 mL of toluene was heated at 70 to 80° C. for about 2 hours and then cooled to room temperature and stirred for 2 days. The mixture was filtered and the resulting solids were dried in a vacuum oven to give cabazitaxel Form C4 as a white solid (melting point: 152.7-168.9° C.). The cabazitaxel Form C4 was also prepared by recrystallisation of cabazitaxel (0.1 g) from 0.4 mL of THF and 1.2 mL of toluene at room temperature.

Example 6

Preparation of Cabazitaxel Crystalline Form C5

A hot solution of cabazitaxel (0.1 g) in 0.8 mL of methyl ethyl ketone and 0.8 mL of n-heptane was slowly cooled to room temperature. The mixture was filtered and the resulting solids were dried in a vacuum oven to give cabazitaxel Form C5 as a white solid (melting point: 159.0-173.5° C.).

Example 7

Preparation of Cabazitaxel Crystalline Form C6

A hot solution of cabazitaxel (0.1 g) in 1 mL of diethyl ketone and 0.7 mL of n-heptane was slowly cooled to room temperature. The mixture was filtered and the resulting solids were dried in a vacuum oven to give cabazitaxel Form C6 as a white solid (melting point: 153.2-164.2° C.).

Example 8

Preparation of Cabazitaxel Crystalline Form C7

A hot solution of cabazitaxel (0.1 g) in 0.8 mL of diethyl carbonate and 0.5 mL of n-heptane was slowly cooled to room temperature. The mixture was filtered and the resulting solids were dried in a vacuum oven to give cabazitaxel Form C7 as a white solid (melting point: 161.2-180° C.).

Example 9

Preparation of Cabazitaxel Crystalline Form C8

A hot solution of cabazitaxel (0.1 g) in 1.5 mL of DMSO and 0.5 mL of $H_2O$ was slowly cooled to room temperature. The mixture was filtered and the resulting solids were dried in a vacuum oven to give cabazitaxel Form C8 as a white solid (melting point: 168.5-174.2° C.).

Example 10

Preparation of Cabazitaxel Crystalline Form C9

A hot solution of cabazitaxel (0.1 g) in 1 mL of AcOH and 0.5 mL of $H_2O$ was slowly cooled to room temperature. The mixture was filtered and the resulting solids were dried in a vacuum oven to give cabazitaxel Form C9 as a white solid (melting point: 152.5-159.3° C.). Form C9 showed a 5% weight loss at 170° C. by TGA analysis and an endotherm at 157° C. was seen in the DSC trace, corresponding with the melting point of between 153 and 159° C. DVS analysis showed a non-perfectly reversible (over 2 cycles tested) weight loss and gain upon changing humidity. This was consistent with a loss of AcOH upon dehumification, which was confirmed by $^1$H NMR spectroscopic analysis after the DVS test. KF analysis of Form C9 showed about 2.3% water.

Example 11

Preparation of Cabazitaxel Crystalline Form C8b

A hot solution of cabazitaxel (5.5 g, 6.6 mmol) in 45 mL of DMSO and 18 mL of $H_2O$ was slowly cooled to between 20 to 25° C. The mixture was filtered and washed with $H_2O$. The resulting solids were dried under vacuum (60-200 torr) at 20 to 25° C. with a nitrogen gas purge to give cabazitaxel Form C8b as a white solid (5.3 g, 6.3 mmol; melting point: 125.2-144.8° C.).

Example 12

Preparation of Cabazitaxel Crystalline Form C9p

A hot solution of cabazitaxel (6.2 g, 7.4 mmol) in 50 mL of AcOH and 42 mL of $H_2O$ was slowly cooled to between 20 and 25° C. The mixture was filtered and washed with $H_2O$. The resulting solids were dried under vacuum (60 to 200 torr) at 20-25° C. with a nitrogen gas purge until the weight of filter cake became constant. The level of AcOH was about 1 molar equivalent with respect to cabazitaxel. Cabazitaxel Form C9p was obtained as a white solid (5.3 g, 6.3 mmol; melting point: 144-154.8° C.).

Example 13

Preparation of Cabazitaxel Crystalline Form C9p

Anhydrous cabazitaxel (76.5 mg, 0.09 mmol) was placed in a sintered glass Buchner funnel. Acetic acid vapor was produced by streaming nitrogen gas through a reservoir of acetic acid, and the vapor was passed through the narrow end of the Buchner funnel so that it flowed though the cabazitaxel sample. The solid cabazitaxel was exposed to the acetic acid vapor at about 25° C. for 17 hours. The material was then purged with nitrogen gas for about 30 minutes at about 25° C., providing Form C9p as a white solid (49 g, 0.06 mmol).

Example 14

Preparation of Cabazitaxel Crystalline Form C9p

Cabazitaxel Form C2 (200 mg, 0.24 mmol) was exposed to acetic acid vapour as described in Example 14 for 22 hours. The solid material was then purged with nitrogen gas for about 30 minutes at about 25° C., providing Form C9p as a white solid (162 mg, 0.2 mmol).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A crystalline form of cabazitaxel selected from the ethyl acetate solvate, the tetrahydrofuran solvate, the methyl ethyl ketone solvate, the diethyl ketone solvate, the diethyl carbonate solvate, or the dimethyl sulfoxide solvate, wherein said crystalline form is substantially free of other crystalline forms; and the ethyl acetate solvate is characterized by an XRPD pattern that comprises peaks at 7.9, 8.6, and 10.1 (+0.1 degrees 2θ);

the tetrahydrofuran solvate is characterized by an XRPD pattern that comprises peaks at 7.8, 8.9, and 10.2 (±0.1 degrees 2θ);

the methyl ethyl ketone solvate is characterized by an XRPD pattern that comprises peaks at 7.8, 8.8, and 10.1 (±0.1 degrees 2θ);

the diethyl ketone solvate is characterized by an XRPD pattern that comprises peaks at 7.8, 8.8, and 10.1 (±0.1 degrees 2θ);

the diethyl carbonate solvate is characterized by an XRPD pattern that comprises peaks at 7.8, 8.6, and 10.1 (±0.1 degrees 2θ); and the dimethyl sulfoxide solvate is characterized by an XRPD pattern that comprises peaks at 7.2, 7.6, and 8.2 (±0.1 degrees 2θ).

2. A crystalline form of cabazitaxel according to claim 1, selected from the ethyl acetate solvate.

3. A crystalline form of cabazitaxel according to claim 1, selected from the tetrahydrofuran solvate.

4. A crystalline form of cabazitaxel according to claim 1, selected from the methyl ethyl ketone solvate.

5. A crystalline form of cabazitaxel according to claim 1, selected from the diethyl ketone solvate.

6. A crystalline form of cabazitaxel according to claim 1, selected from the diethyl carbonate solvate.

7. A crystalline form of cabazitaxel according to claim 1, selected from the dimethyl sulfoxide solvate.

8. A composition comprising a pharmaceutically acceptable excipient and a crystalline form of cabazitaxel according to claim 1.

* * * * *